(12) United States Patent
Ostanin et al.

(10) Patent No.: US 10,849,901 B2
(45) Date of Patent: Dec. 1, 2020

(54) ARF6 INHIBITORS AND METHODS OF SYNTHESIS AND USE THEREOF

(71) Applicants: Navigen, Inc., Salt Lake City, UT (US); The University of Utah Research Founcation, Salt Lake City, UT (US)

(72) Inventors: Kirill Ostanin, Salt Lake City, UT (US); Mark Shenderovich, Salt Lake City, UT (US); Ashok Bajji, Salt Lake City, UT (US); Christopher L. Cioffi, Salt Lake City, UT (US); Neil Moss, Salt Lake City, UT (US); Hariprasad Vankayalapati, Salt Lake City, UT (US); Dean Li, Salt Lake City, UT (US)

(73) Assignees: Navigen, Inc., Salt Lake City, UT (US); The University of Utah Research Foundation, Salt Lake City, UT (US)

( * ) Notice: Subject to any disclaimer, the term of this patent is extended or adjusted under 35 U.S.C. 154(b) by 0 days.

(21) Appl. No.: 15/313,884

(22) PCT Filed: May 27, 2015

(86) PCT No.: PCT/US2015/032720
§ 371 (c)(1),
(2) Date: Nov. 23, 2016

(87) PCT Pub. No.: WO2015/183989
PCT Pub. Date: Dec. 3, 2015

(65) Prior Publication Data
US 2017/0189405 A1    Jul. 6, 2017

Related U.S. Application Data

(60) Provisional application No. 62/003,355, filed on May 27, 2014.

(51) Int. Cl.
*A61K 31/519* (2006.01)
*A61K 31/5377* (2006.01)

(52) U.S. Cl.
CPC ........ *A61K 31/519* (2013.01); *A61K 31/5377* (2013.01); *Y02A 50/385* (2018.01)

(58) Field of Classification Search
CPC ............ A61K 31/519; A61K 31/5377; Y02A 50/385; A61P 9/00; A61P 7/00;
(Continued)

(56) References Cited

U.S. PATENT DOCUMENTS 10,421,743 B2   9/2019  Bergman et al.
10,428,046 B2  10/2019  Yamamoto et al.
(Continued)

FOREIGN PATENT DOCUMENTS

JP    2011518178 A    6/2011
WO    2004016271 A1   2/2004
(Continued)

OTHER PUBLICATIONS

PCT/US2015/032720, International Search Report and Written Opinion, dated Aug. 14, 2015, 10 pages.
(Continued)

*Primary Examiner* — Taylor V Oh
(74) *Attorney, Agent, or Firm* — Stoel Rives LLP

(57) ABSTRACT

Disclosed herein are compounds and methods for inhibiting Arf6. Pharmaceutical compositions and methods for treating a subject with an inhibitor of Arf6 are also disclosed herein.

12 Claims, 9 Drawing Sheets

(58) Field of Classification Search
CPC ......... A61P 43/00; A61P 35/00; A61P 31/16; A61P 31/04; A61P 31/12; A61P 29/00; A61P 27/02; A61P 19/02; A61P 11/00
USPC .................................................. 514/233.2
See application file for complete search history.

(56) References Cited

U.S. PATENT DOCUMENTS

| | | | |
|---|---|---|---|
| 10,428,070 | B2 | 10/2019 | Yao-Ling et al. |
| 10,435,429 | B2 | 10/2019 | Zhi |
| 10,441,570 | B2 | 10/2019 | Narayanan et al. |
| 2010/0222401 | A1 | 9/2010 | Li et al. |
| 2012/0178915 | A1 | 7/2012 | Xu |
| 2012/0277224 | A1 | 11/2012 | McCall et al. |

FOREIGN PATENT DOCUMENTS

| | | |
|---|---|---|
| WO | 2011028492 A2 | 3/2011 |
| WO | 2012065139 A2 | 5/2012 |

OTHER PUBLICATIONS

Hoshimoto, et al., GEP100-Arf6-AMAP1-Cortactin Pathway Frequently Used in Cancer Invasion is Activated by VEGFR to Promote Angiogenesis, PLoS One, vol. 6, Article No. e23359, Aug. 15, 2011, 11 pages ,Aug. 15, 2011.

Jones, et al., Sht2-Robo4 Signalling Promotes Vascular Stability by Blocking Arf6 Activity, Natural Cell Biology, vol. 11, Oct. 18, 2009, pp. 1325-1331 ,Oct. 18, 2009 ,1325-1331.

Ostanin, et al., Office Action dated Jun. 25, 2019 for Japanese Application No. 2017-515005.

Extended European Search Report (EESR) dated Dec. 8, 2017 for EP application 15799998.8.

Chuvashlev, et al.,5-Amino-3-alkyl-2-arylpyrazoles in synthesis of pyrazolo[1,5-a]pyrimidines, Izvestia Vyssih UceBnyh Zavedenij. Himia/Himiceskaa Technol, vol. 52, No. 11, 2009, pp. 25-30.

Mao, et al., Structure-activity relationships of compounds targeting mycobacterium tuberculosis 1-deoxy-d-xylulose 5-phosphate synthase, Biorganic & Medical Chemistry Letters, vol. 18, No. 19, 2008, pp. 5320-5323.

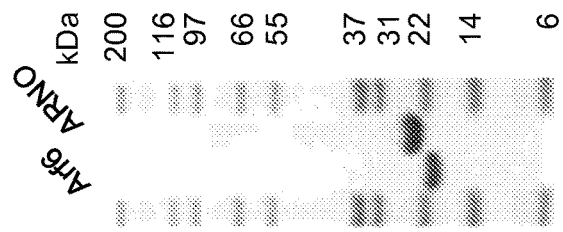
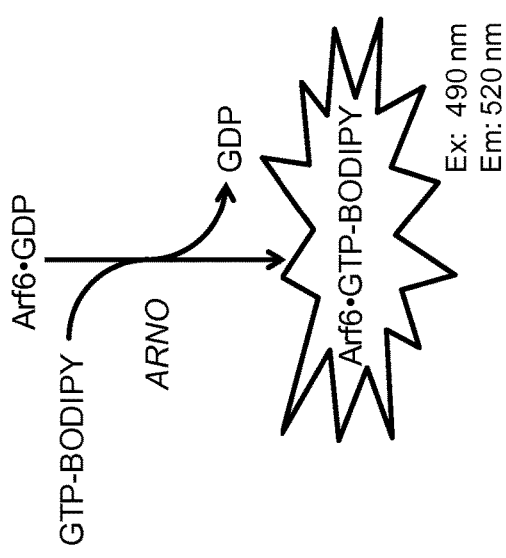
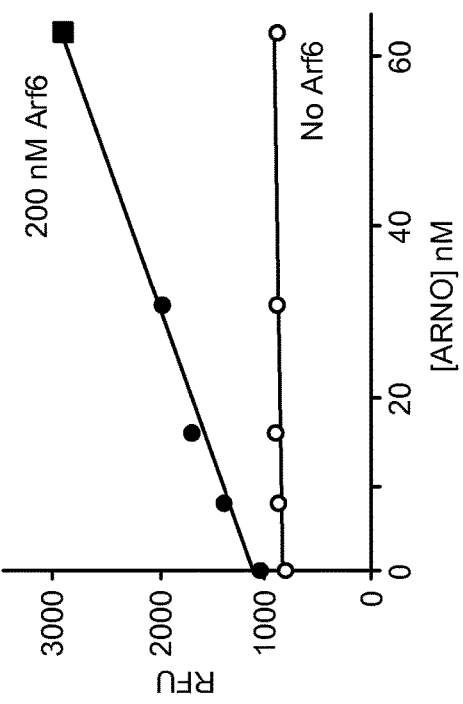
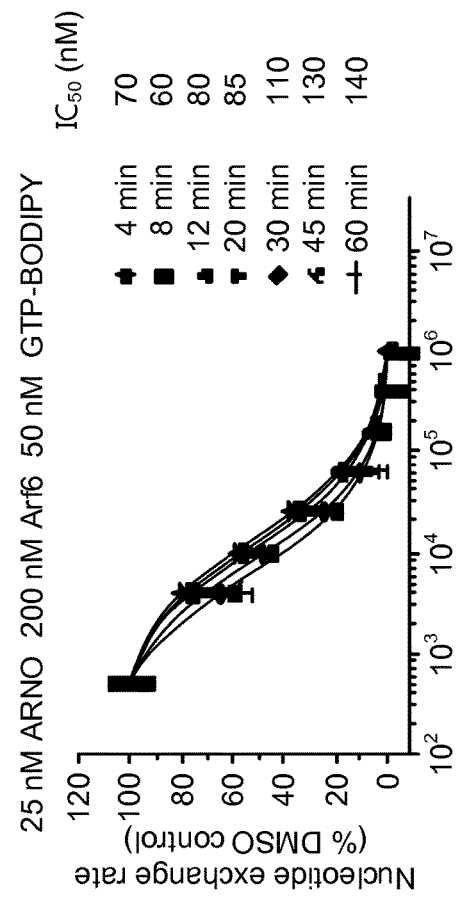
FIG. 1A
FIG. 1B
FIG. 1C
FIG. 1D

Effect of Compound 38 on LOX Cell Proliferation

Effect of Compound 38 on LN-229 Cell Proliferation

ARF6 INHIBITORS AND METHODS OF SYNTHESIS AND USE THEREOF

RELATED APPLICATIONS

This application is a national stage entry of PCT/US2015/032720, filed May 27, 2015, which claims priority to and the benefit of U.S. Provisional Patent Application No. 62/003,355, filed May 27, 2014, each of which is hereby incorporated by reference in its entirety.

TECHNICAL FIELD

The present disclosure relates to inhibitors of Arf6, to methods and processes for synthesizing inhibitors of Arf6, and pharmaceutical compositions comprising inhibitors of Arf6. The present disclosure also relates to the use of inhibitors of Arf6 in the treatment or prevention of diseases relating to vascular leak, vascular inflammation, or angiogenesis including, but not limited to, acute lung injury, acute viral infections, sepsis, age-related macular degeneration, rheumatoid arthritis, and cancer.

BACKGROUND

Arf6 is a member of the Ras superfamily of small GTP-binding proteins. Arf6 has been shown to play a role in endocytic trafficking and can regulate cell functions including adhesion, motility, and cell division. Arf6 can be activated by the exchange of intrinsically bound GDP for GTP that, depending on physiological context, can be catalyzed by a number of guanine nucleotide exchange factors (GEFs) including ARNO. Arf6 may mediate cytokine-induced vascular hyperpermeability by promoting endocytosis of vascular endothelial (VE)-cadherin, a component of interendothelial adherens junctions with roles in the control of vascular integrity.

The vasculature is continually exposed to events, conditions, or pathogens that may cause injury, ischemia, and inflammation, which may result in the release of cytokines and angiogenic factors, which can destabilize the endothelial cell-cell junctions, leading to endothelial permeability. In some cases, this stimulation of endothelial proliferation and migration may result in vascular sprouting and edema, and in other cases it may result in vascular leak. These functions can serve to deconstruct a stable vascular network producing leaky new blood vessels. In some contexts, the release of cytokines and angiogenic factors in response to injury, ischemia, and inflammation may be desirable, in that such a response can initiate a restorative or healing process. However, excessive angiogenesis and vascular leak (e.g., endothelial hyperpermeability) can underscore the pathologies of several disease and pathologic conditions.

Pathologic angiogenesis can be associated with a number of conditions including retinopathies, tumor formation, and tumor growth. A number of diseases and disorders can be characterized by undesirable vascular permeability including, for example, edema associated with brain tumors, ascites associated with malignancies, Meigs' syndrome, lung inflammation, nephritic syndrome, pericardial effusion, pleural effusion, acute lung injury, inflammatory bowel disease, ischemia/reperfusion injury in stroke, myocardial infarction, and infectious and non-infectious diseases that result in cytokine storm.

Cytokine storm can create at least two cascades of events. The first is the perpetuation of the production of cytokine and inflammatory mediators; and the second is the destabilization of the vasculature and subsequent vascular leakage. Enhancing cell surface levels of VE-cadherin using Arf6 antagonists as a treatment strategy can leave immune function predominantly intact and strengthen the vascular endothelium. As such, Arf6 inhibitors can play a role in vascular stabilization in conditions associated with hypercytokinemia including, but not limited to, sepsis, pneumonia, acute viral infections, and acute lung injury. In such cases of hypercytokinemia, directly inhibiting immune function may not be a viable option, as can be demonstrated by the clinical failures of many corticosteroids and anti-inflammatory drugs.

BRIEF DESCRIPTION OF THE FIGURES

The written disclosure herein describes illustrative embodiments that are non-limiting and non-exhaustive. Reference is made to certain of such illustrative embodiments that are depicted in the figures described herein.

FIGS. 1A-1D: Fluorometric high throughput assay for Arf6 nucleotide exchange catalyzed by ARNO Sec7 domain. FIG. 1A: Principle of the assay. FIG. 1B: SDS-PAGE analysis of N-terminally His-tagged Arf6(14-175) and ARNO(50-255) purified from the $E.\ coli$ cultures by immobilized metal affinity chromatography. FIG. 1C: Correlation between signal intensity and ARNO concentration. The assay was performed using 50 mM Tris-HCl, pH 7.5, 1 mM $MgCl_2$, 0.01% TX-100, 1% DMSO, 50 nM GTP-BODIPY FL, supplemented with ARNO-Sec7 at indicated concentrations in the absence or in the presence of 0.2 µM Arf6-GDP. Fluorescence intensities were monitored using a Synergy 4 plate reader (BioTek) at the excitation and emission wavelengths of 490 nm and 520 nm, respectively. FIG. 1D: Time course of apparent inhibitory potency of GDP. The assay was performed in automated mode using a Matrix PlateMate liquid handler.

DETAILED DESCRIPTION

Figure 2:
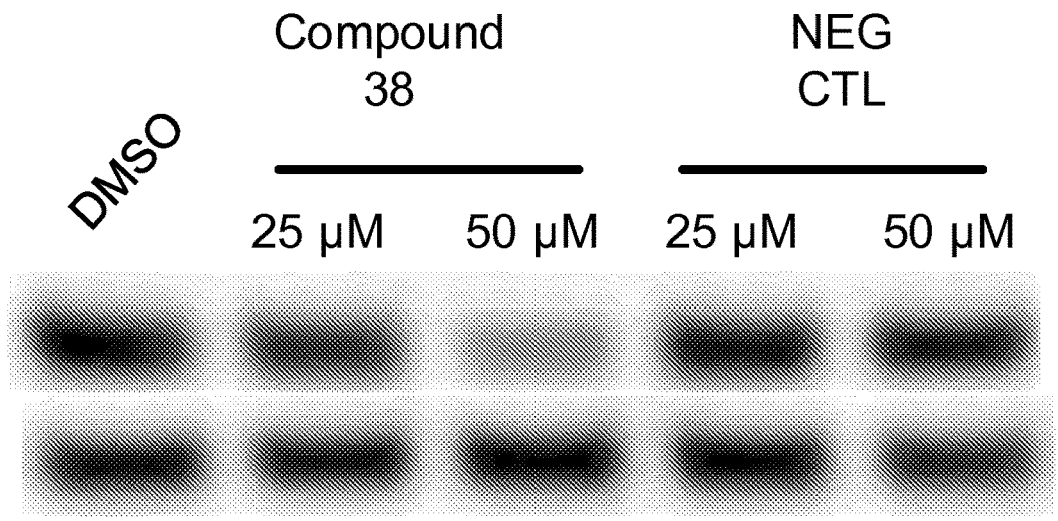
FIG. 2: Inhibition of Arf6 activation in NIH3T3 cells by Compound 38. A biochemically inactive analog "NEG CTL" was used as negative control. The cell cultures were incubated in the presence of test compounds for 4 hours followed by pull-down of GTP-bound Arf6 from cell lysates using recombinant GST-Gga3 immobilized on glutathione agarose and Western blot analysis.

The present disclosure relates to novel inhibitors of Arf6, to processes for synthesizing Arf6 inhibitors, pharmaceutical compositions comprising Arf6 inhibitors, and the use of Arf6 inhibitors in the treatment or prevention of diseases relating to, but not limited to, vascular leak, vascular inflammation, or angiogenesis including, but not limited to, acute lung injury; influenza-induced acute respiratory distress; sepsis; hemorrhagic fever viruses such as Ebola virus, Marburg virus, hantavirus, or dengue virus; age-related macular degeneration; rheumatoid arthritis; or cancer.

The inhibitors of Arf6 may also be used in the treatment or prevention of an ocular disease, a lung injury, a viral infection, and/or an inflammatory disease. In some embodiments, the ocular disease may comprise impaired retinal permeability, impaired ocular vascularization, or macular edema, or may be the result of oxygen-induced retinopathy, retinopathy of prematurity, or diabetic retinopathy. In various embodiments, the lung injury may comprise an acute lung injury. In certain embodiments, the viral infection may comprise an H1N1 infection. In some embodiments, the inflammatory disease may comprise arthritis.

Compounds and pharmaceutical compositions disclosed herein can be used to treat diseases other than those listed herein, which may involve dysfunction in one or more cellular processes related to Arf6 activity.

Compounds

In general, the present disclosure may relate to compounds of Formula I, pharmaceutically acceptable salts thereof, and pharmaceutical compositions comprising the compounds of Formula 1 and the pharmaceutically acceptable salts thereof.

FORMULA I

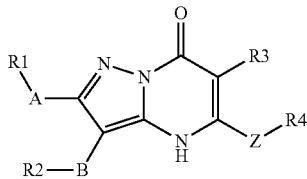

In the compounds of Formula I, the group labeled R1 is independently selected from at least one of hydrogen, hydroxyl, halo, alkyl, alkoxy, haloalkyl, haloalkoxy, cycloalkyl, phenyl, substituted phenyl, pyridyl, morpholino, and pyranyl. When R1 is a substituted phenyl, each position on the phenyl ring may independently be substituted with an alkyl, alkylthio, alkoxy, or halo group.

In the compounds of Formula I, the group labeled R2 is independently selected from at least one of hydrogen, alkyl, optionally substituted aryl, cycloalkyl, and sulfonyl. When R2 is a substituted aryl, each position on the aryl group may independently be substituted with an alkyl, alkoxy, aryloxy, cycloalkyl, halo, haloalkyl, phenyloxy, or sulfonyl group.

In the compounds of Formula I, the group labeled R3 is independently selected from at least one of hydrogen, alkyl, or halo.

In the compounds of Formula I, the group labeled R4 is independently selected from at least one of hydrogen, alkyl, optionally substituted aryl, cycloalkyl, and pyridyl. When R4 is a substituted aryl, each position on the aryl group may independently be substituted with an alkyl, alkoxy, amino, cyano, hydroxyl, halo, carboxy, nitro, pyridyl, alkyl-substituted pyridyl, amino-substituted pyridyl, alkoxy-substituted pyridyl, O-phenyl wherein the phenyl may optionally be substituted with halo, NHC(O)-alkyl, NHC(O)-alkoxy, NHC(O)-A-phenyl, sulfonyl, NHSO$_2$-alkyl, NHSO$_2$-benzyl, NHC(O)NH-alkyl, NHC(O)NH-benzyl, NHC(O)NH-alkyl, C— amido, and N-amido.

In the compounds of Formula I, the groups labeled A, B, and Z are each independently a bond or an optionally substituted methylene, wherein the methylene may optionally be substituted with an alkyl group. In an embodiment, the methylene may be substituted with a methyl group.

In certain embodiments, R1 is independently selected from at least one of hydrogen, hydroxyl, halo, alkyl, alkoxy, haloalkyl, haloalkoxy, cycloalkyl, phenyl, substituted phenyl, pyridyl, morpholino or pyranyl; R2 is independently selected from at least one of hydrogen, alkyl, optionally substituted aryl, cycloalkyl, or sulfonyl; R3 is hydrogen or halo; R4 is independently selected from at least one of hydrogen, alkyl, optionally substituted aryl, cycloalkyl, and pyridyl; and A, B, and Z are each independently a bond or an optionally substituted methylene.

All chiral conformations and combinations thereof are included in the compounds of Formula I. When different substituents are recited for the R groups, there is no chirality assumed or intended by the order of recitation, although all conformations are included. Some of the compounds of Formula I for use in embodiments of the present disclosure may exist as single stereoisomers (i.e., essentially free of other stereoisomers), racemates, and/or mixtures of enantiomers, and/or diastereomers. All such single stereoisomers, racemates, and mixtures thereof are intended to be within the scope of the present disclosure. Furthermore, some of the compounds for use in embodiments of the present disclosure can exist as cis and trans geometric isomers, and all such isomers and mixtures thereof are intended to be within the scope of the present disclosure.

Exemplary compounds of Formula I, and analogs thereof, can include the compounds shown in Table 1. The compounds of Formula I can include pharmaceutically acceptable salts thereof.

TABLE 1

Exemplary Compounds of Formula I

| Compound Number | Compound Structure | IC50 (μM) 20 nM Arf6 | IC50 (μM) 200 nM Arf6 |
|---|---|---|---|
| 1 | 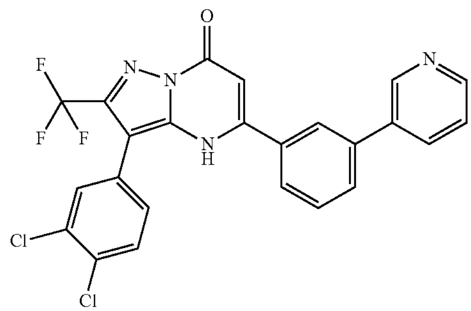 [SMILES: O=c1cc(-c2cccc(-c3cccnc3)c2)[nH]c2c(-c3ccc(Cl)c(Cl)c3)c(C(F)(F)F)nn12] | 0.25 | |
| 2 | 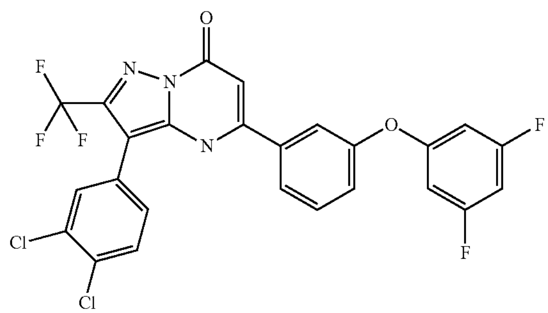 [SMILES: O=c1cc(-c2cccc(Oc3cc(F)cc(F)c3)c2)[nH]c2c(-c3ccc(Cl)c(Cl)c3)c(C(F)(F)F)nn12] | 0.33 | |
| 3 | 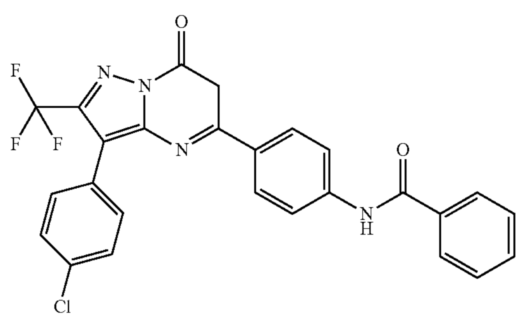 [SMILES: O=C(Nc1ccc(C2=Nc3c(-c4ccc(Cl)cc4)c(C(F)(F)F)nn3C(=O)C2)cc1)c1ccccc1] | 0.5 | |
| 4 | 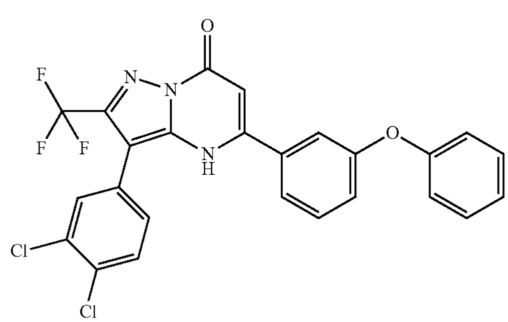 [SMILES: O=c1cc(-c2cccc(Oc3ccccc3)c2)[nH]c2c(-c3ccc(Cl)c(Cl)c3)c(C(F)(F)F)nn12] | 0.52 | 0.46 |

TABLE 1-continued

Exemplary Compounds of Formula I

| Compound Number | Compound Structure | IC50 (μM) 20 nM Arf6 | IC50 (μM) 200 nM Arf6 |
|---|---|---|---|
| 5 | (2-phenyl-3-(3,4-dichlorophenyl)-5-(4-nitrophenyl)pyrazolo[1,5-a]pyrimidin-7(4H)-one) | 0.58 | |
| 6 | (2-(trifluoromethyl)-3-(3,4-dichlorophenyl)-5-(4-phenoxyphenyl)pyrazolo[1,5-a]pyrimidin-7(4H)-one) | 0.66 | 1.1 |
| 7 | (2-(trifluoromethyl)-3-(3,4-dichlorophenyl)-5-(4-nitrophenyl)pyrazolo[1,5-a]pyrimidin-7(4H)-one) | 0.66 | |
| 8 | (2-(trifluoromethyl)-3-(4-chloro-3-(trifluoromethyl)phenyl)-5-(4-nitrophenyl)pyrazolo[1,5-a]pyrimidin-7(4H)-one) | 0.67 | |

TABLE 1-continued

Exemplary Compounds of Formula I

| Compound Number | Compound Structure | IC50 (μM) 20 nM Arf6 | IC50 (μM) 200 nM Arf6 |
|---|---|---|---|
| 9 | 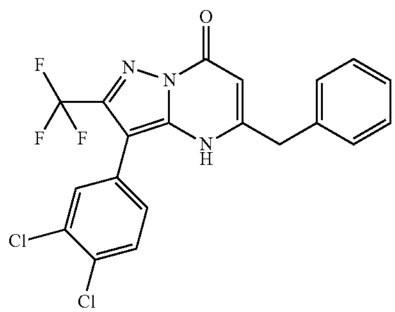 [SMILES: O=c1cc(Cc2ccccc2)[nH]c2c(-c3ccc(Cl)c(Cl)c3)c(C(F)(F)F)nn12] | 0.84 | 1.6 |
| 10 | 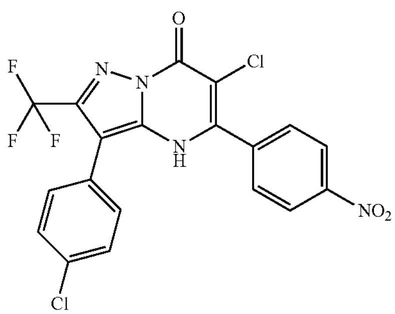 [SMILES: O=c1c(Cl)c(-c2ccc([N+](=O)[O-])cc2)[nH]c2c(-c3ccc(Cl)cc3)c(C(F)(F)F)nn12] | 0.88 | |
| 11 | 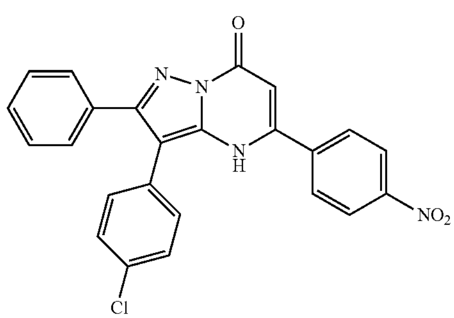 [SMILES: O=c1cc(-c2ccc([N+](=O)[O-])cc2)[nH]c2c(-c3ccc(Cl)cc3)c(-c3ccccc3)nn12] | 0.96 | |
| 12 | 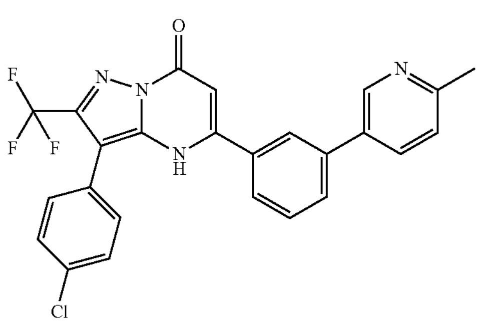 [SMILES: Cc1ccc(-c2cccc(-c3cc(=O)n4nc(C(F)(F)F)c(-c5ccc(Cl)cc5)c4[nH]3)c2)cn1] | 0.96 | |

TABLE 1-continued
Exemplary Compounds of Formula I
| Compound Number | Compound Structure | IC50 (μM) 20 nM Arf6 | IC50 (μM) 200 nM Arf6 |
|---|---|---|---|
| 13 | 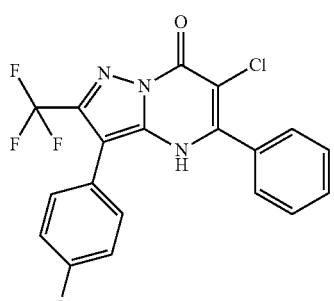 | 0.98 | |
| 14 | 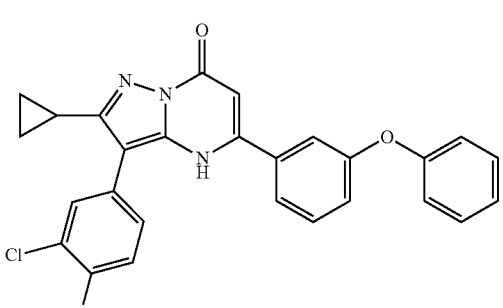 | 1 | |
| 15 | 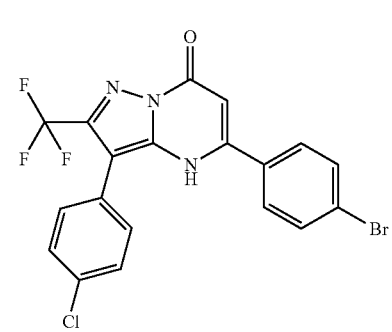 [SMILES: O=c1cc(-c2ccc(Br)cc2)[nH]c2c(-c3ccc(Cl)cc3)c(C(F)(F)F)nn12] | 1.1 | |
| 16 | 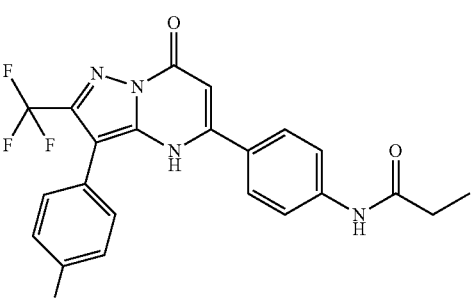 | 1.1 | |

TABLE 1-continued

Exemplary Compounds of Formula I

| Compound Number | Compound Structure | IC50 (μM) 20 nM Arf6 | IC50 (μM) 200 nM Arf6 |
| --- | --- | --- | --- |
| 17 | 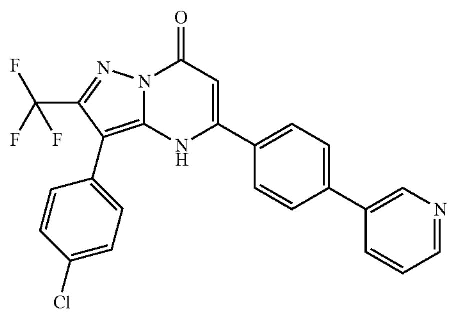 [SMILES: O=c1cc(-c2ccc(-c3cccnc3)cc2)[nH]c2c(-c3ccc(Cl)cc3)c(C(F)(F)F)nn12] | | 1.1 |
| 18 | 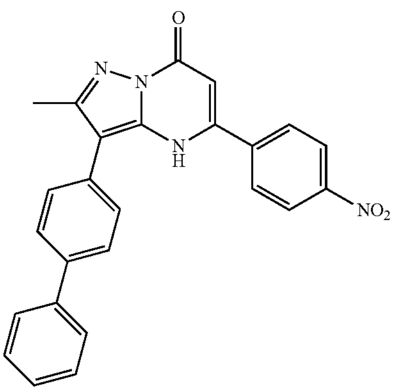 [SMILES: Cc1nn2c(=O)cc(-c3ccc([N+](=O)[O-])cc3)[nH]c2c1-c1ccc(-c2ccccc2)cc1] | | 1.1 |
| 19 | 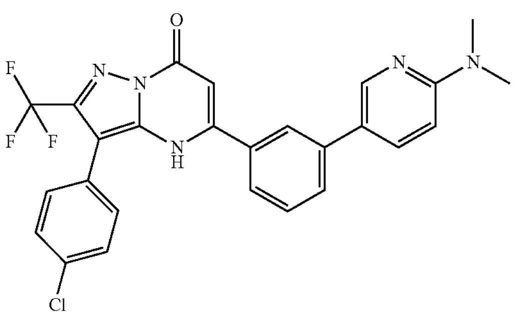 [SMILES: CN(C)c1ccc(-c2cccc(-c3cc(=O)n4nc(C(F)(F)F)c(-c5ccc(Cl)cc5)c4[nH]3)c2)cn1] | | 1.1 |
| 20 | 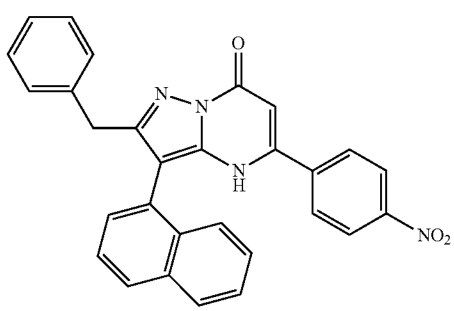 [SMILES: O=c1cc(-c2ccc([N+](=O)[O-])cc2)[nH]c2c(-c3cccc4ccccc34)c(Cc3ccccc3)nn12] | | 1.1 |

TABLE 1-continued

Exemplary Compounds of Formula I

| Compound Number | Compound Structure | IC50 (μM) 20 nM Arf6 | IC50 (μM) 200 nM Arf6 |
|---|---|---|---|
| 21 | 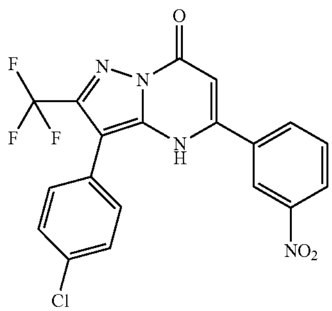 [SMILES: O=c1cc(-c2cccc([N+](=O)[O-])c2)[nH]c2c(-c3ccc(Cl)cc3)c(C(F)(F)F)nn12] | 1.2 | |
| 22 | 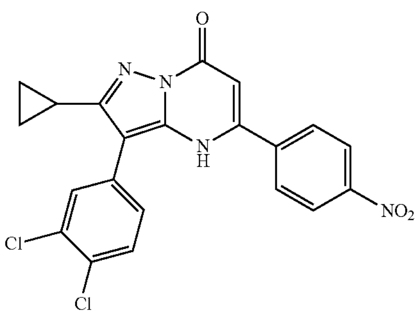 [SMILES: O=c1cc(-c2ccc([N+](=O)[O-])cc2)[nH]c2c(-c3ccc(Cl)c(Cl)c3)c(C3CC3)nn12] | 1.2 | |
| 23 | 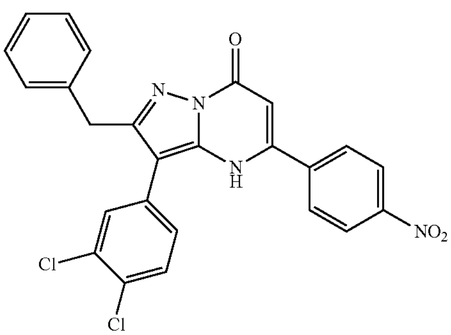 [SMILES: O=c1cc(-c2ccc([N+](=O)[O-])cc2)[nH]c2c(-c3ccc(Cl)c(Cl)c3)c(Cc3ccccc3)nn12] | 1.2 | |
| 24 | 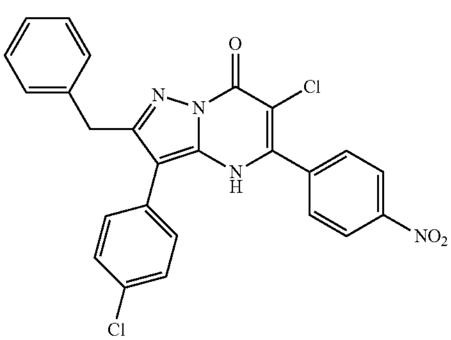 [SMILES: O=c1c(Cl)c(-c2ccc([N+](=O)[O-])cc2)[nH]c2c(-c3ccc(Cl)cc3)c(Cc3ccccc3)nn12] | 1.3 | 1.4 |

TABLE 1-continued

Exemplary Compounds of Formula I

| Compound Number | Compound Structure | IC50 (μM) 20 nM Arf6 | IC50 (μM) 200 nM Arf6 |
|---|---|---|---|
| 25 | 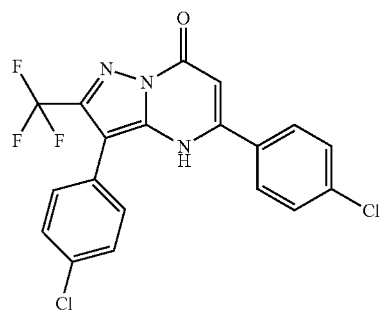 [SMILES: O=c1cc(-c2ccc(Cl)cc2)[nH]c2c(-c3ccc(Cl)cc3)c(C(F)(F)F)nn12] | 1.4 | |
| 26 | 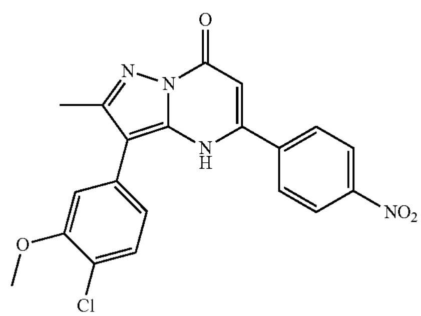 [SMILES: COc1cc(-c2c(C)nn3c(=O)cc(-c4ccc([N+](=O)[O-])cc4)[nH]c23)ccc1Cl] | 1.4 | |
| 27 | 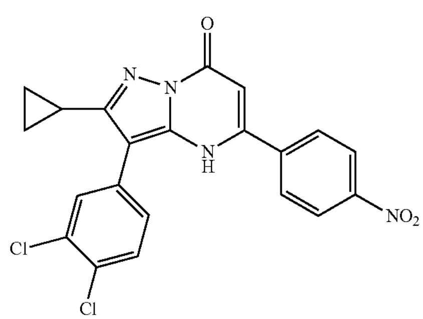 [SMILES: O=c1cc(-c2ccc([N+](=O)[O-])cc2)[nH]c2c(-c3ccc(Cl)c(Cl)c3)c(C3CC3)nn12] | 1.4 | |
| 28 | 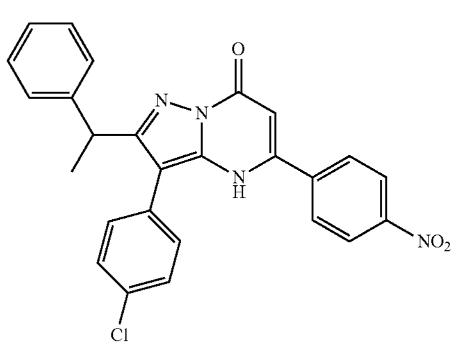 [SMILES: CC(c1ccccc1)c1nn2c(=O)cc(-c3ccc([N+](=O)[O-])cc3)[nH]c2c1-c1ccc(Cl)cc1] | 1.4 | |

TABLE 1-continued

Exemplary Compounds of Formula I

| Compound Number | Compound Structure | IC50 (μM) 20 nM Arf6 | IC50 (μM) 200 nM Arf6 |
|---|---|---|---|
| 29 | 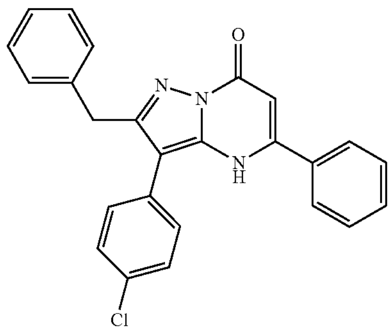 [SMILES: O=c1cc(-c2ccccc2)[nH]c2c(-c3ccc(Cl)cc3)c(Cc3ccccc3)nn12] | 1.5 | 3.3 |
| 30 | 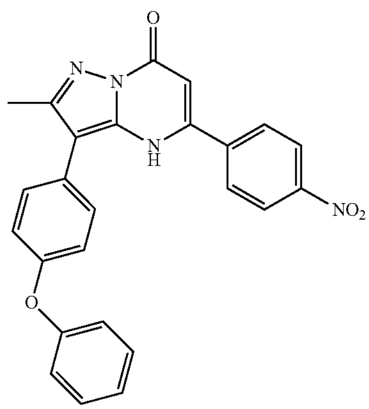 [SMILES: Cc1nn2c(=O)cc(-c3ccc([N+](=O)[O-])cc3)[nH]c2c1-c1ccc(Oc2ccccc2)cc1] | 1.5 | |
| 31 | 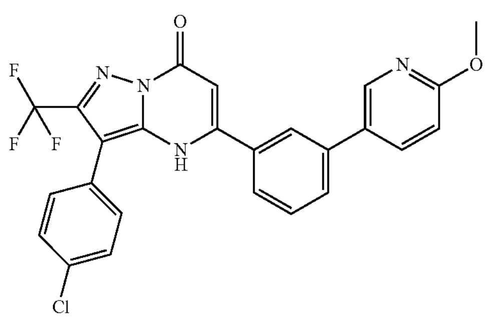 [SMILES: COc1ccc(-c2cccc(-c3cc(=O)n4nc(C(F)(F)F)c(-c5ccc(Cl)cc5)c4[nH]3)c2)cn1] | 1.5 | |
| 32 | 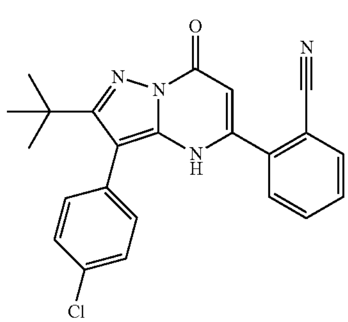 [SMILES: CC(C)(C)c1nn2c(=O)cc(-c3ccccc3C#N)[nH]c2c1-c1ccc(Cl)cc1] | 1.5 | |

TABLE 1-continued
Exemplary Compounds of Formula I
| Compound Number | Compound Structure | IC50 (μM) 20 nM Arf6 | IC50 (μM) 200 nM Arf6 |
|---|---|---|---|
| 33 | 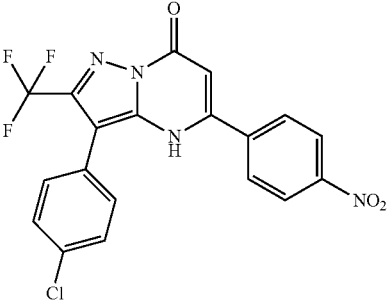 [SMILES: O=c1cc(-c2ccc([N+](=O)[O-])cc2)[nH]c2c(-c3ccc(Cl)cc3)c(C(F)(F)F)nn12] | 1.6 | 2.6 |
| 34 | 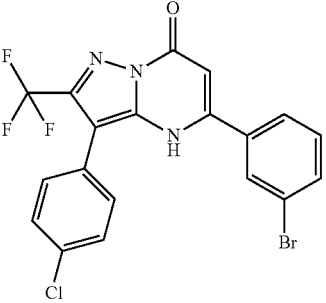 [SMILES: O=c1cc(-c2cccc(Br)c2)[nH]c2c(-c3ccc(Cl)cc3)c(C(F)(F)F)nn12] | 1.6 | |
| 35 | 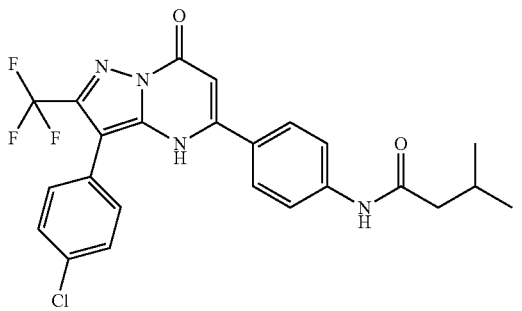 [SMILES: CC(C)CC(=O)Nc1ccc(-c2cc(=O)n3nc(C(F)(F)F)c(-c4ccc(Cl)cc4)c3[nH]2)cc1] | 1.7 | |
| 36 | 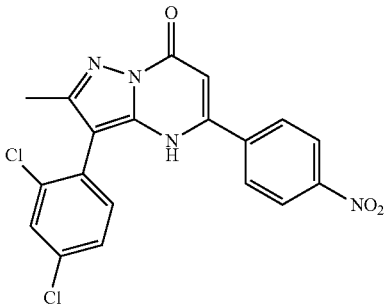 [SMILES: Cc1nn2c(=O)cc(-c3ccc([N+](=O)[O-])cc3)[nH]c2c1-c1ccc(Cl)cc1Cl] | 1.7 | |

TABLE 1-continued
Exemplary Compounds of Formula I
| Compound Number | Compound Structure | IC50 (µM) 20 nM Arf6 | IC50 (µM) 200 nM Arf6 |
| --- | --- | --- | --- |
| 37 | 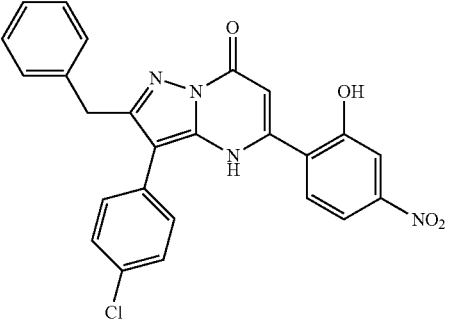 [SMILES: O=c1cc(-c2ccc([N+](=O)[O-])cc2O)[nH]c2c(-c3ccc(Cl)cc3)c(Cc3ccccc3)nn12] | | 1.7 |
| 38 | 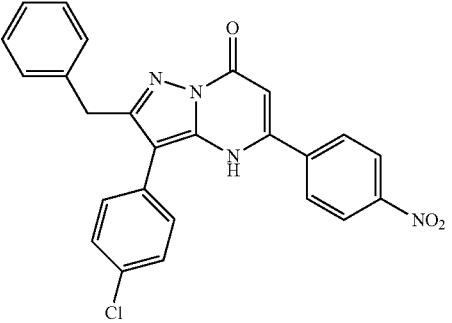 [SMILES: O=c1cc(-c2ccc([N+](=O)[O-])cc2)[nH]c2c(-c3ccc(Cl)cc3)c(Cc3ccccc3)nn12] | 1.8 | 1.4 |
| 39 | 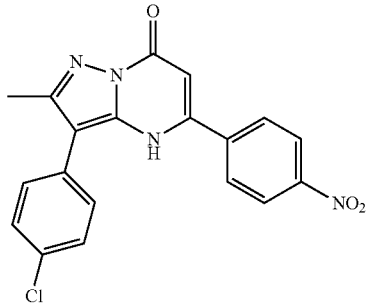 [SMILES: Cc1nn2c(=O)cc(-c3ccc([N+](=O)[O-])cc3)[nH]c2c1-c1ccc(Cl)cc1] | 1.9 | 4.7 |
| 40 | 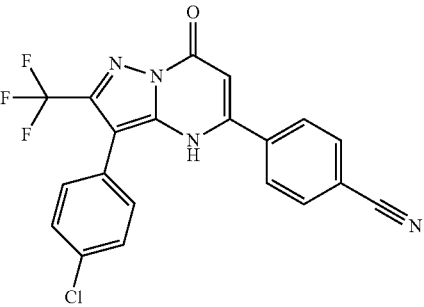 [SMILES: N#Cc1ccc(-c2cc(=O)n3nc(C(F)(F)F)c(-c4ccc(Cl)cc4)c3[nH]2)cc1] | 1.9 | |

TABLE 1-continued

Exemplary Compounds of Formula I

| Compound Number | Compound Structure | IC50 (μM) 20 nM Arf6 | IC50 (μM) 200 nM Arf6 |
|---|---|---|---|
| 41 | 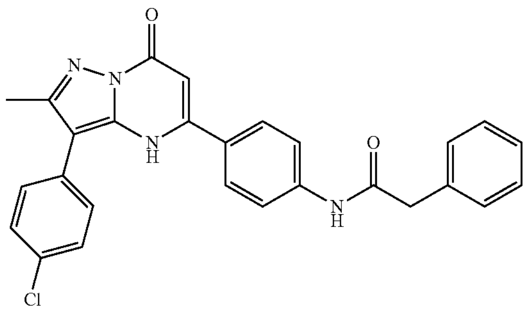 [SMILES: Cc1nn2c(=O)cc(-c3ccc(NC(=O)Cc4ccccc4)cc3)[nH]c2c1-c1ccc(Cl)cc1] | | 1.9 |
| 42 | 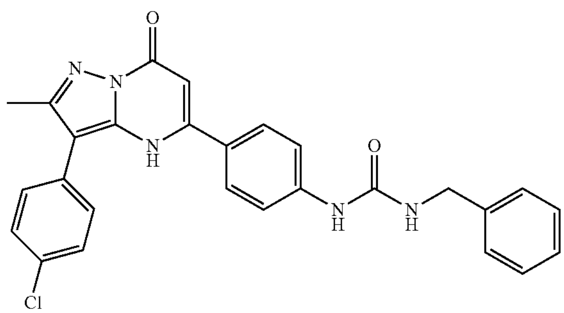 [SMILES: Cc1nn2c(=O)cc(-c3ccc(NC(=O)NCc4ccccc4)cc3)[nH]c2c1-c1ccc(Cl)cc1] | | 2.1 |
| 43 | 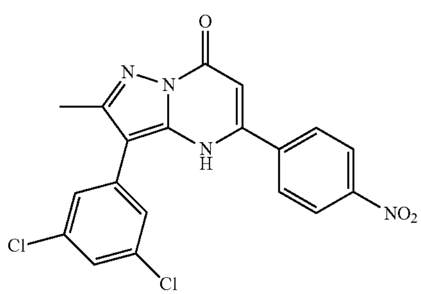 [SMILES: Cc1nn2c(=O)cc(-c3ccc([N+](=O)[O-])cc3)[nH]c2c1-c1cc(Cl)cc(Cl)c1] | | 2.1 |
| 44 | 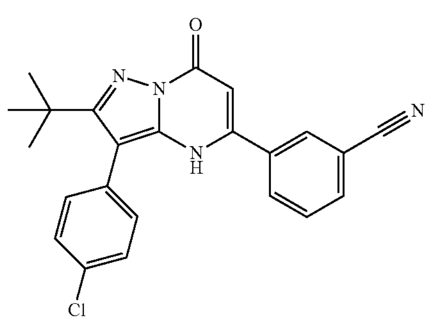 [SMILES: CC(C)(C)c1nn2c(=O)cc(-c3cccc(C#N)c3)[nH]c2c1-c1ccc(Cl)cc1] | | 2.2 |

TABLE 1-continued

Exemplary Compounds of Formula I

| Compound Number | Compound Structure | IC50 (μM) 20 nM Arf6 | IC50 (μM) 200 nM Arf6 |
|---|---|---|---|
| 45 | 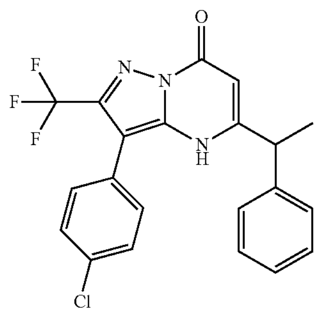 [SMILES: CC(c1ccccc1)c1cc(=O)n2nc(C(F)(F)F)c(-c3ccc(Cl)cc3)c2[nH]1] | 2.3 | |
| 46 | 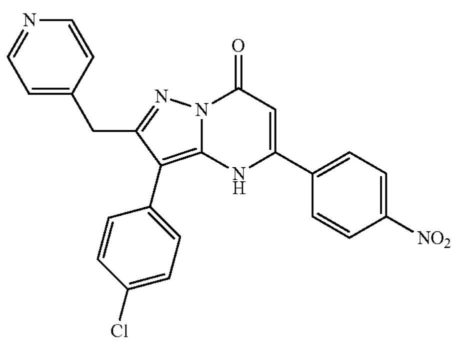 [SMILES: O=c1cc(-c2ccc([N+](=O)[O-])cc2)[nH]c2c(-c3ccc(Cl)cc3)c(Cc3ccncc3)nn12] | 2.4 | 3.2 |
| 47 | 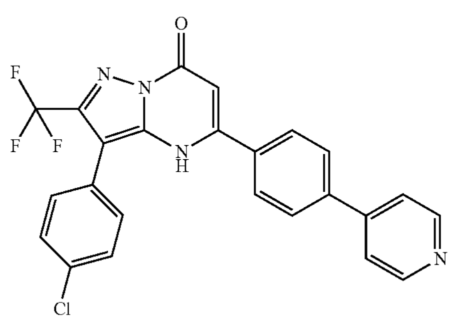 [SMILES: O=c1cc(-c2ccc(-c3ccncc3)cc2)[nH]c2c(-c3ccc(Cl)cc3)c(C(F)(F)F)nn12] | 2.4 | |
| 48 | 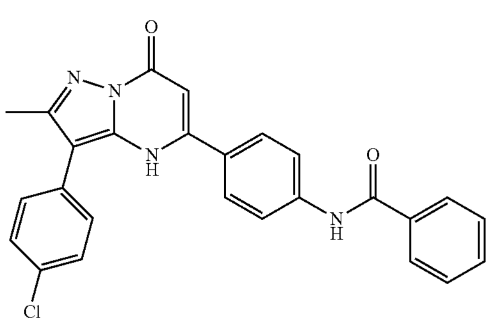 [SMILES: Cc1nn2c(=O)cc(-c3ccc(NC(=O)c4ccccc4)cc3)[nH]c2c1-c1ccc(Cl)cc1] | 2.4 | |

TABLE 1-continued

Exemplary Compounds of Formula I

| Compound Number | Compound Structure | IC50 (μM) 20 nM Arf6 | IC50 (μM) 200 nM Arf6 |
|---|---|---|---|
| 49 | 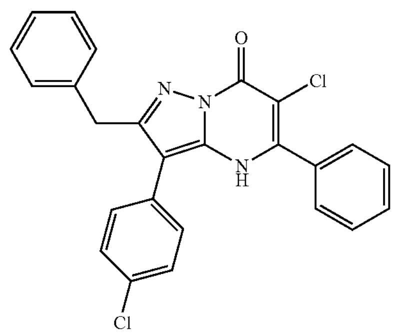 [SMILES: O=c1c(Cl)c(-c2ccccc2)[nH]c2c(-c3ccc(Cl)cc3)c(Cc3ccccc3)nn12] | 2.5 | |
| 50 | 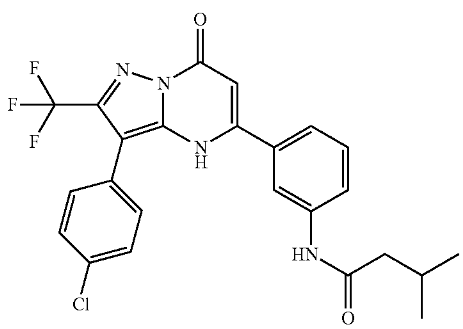 [SMILES: CC(C)CC(=O)Nc1cccc(-c2cc(=O)n3nc(C(F)(F)F)c(-c4ccc(Cl)cc4)c3[nH]2)c1] | 2.5 | |
| 51 | 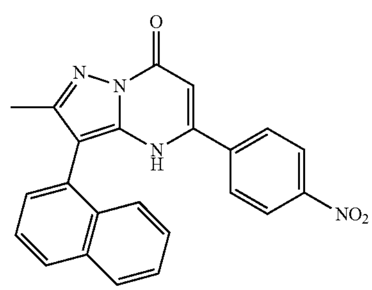 [SMILES: Cc1nn2c(=O)cc(-c3ccc([N+](=O)[O-])cc3)[nH]c2c1-c1cccc2ccccc12] | 2.7 | 4.9 |
| 52 | 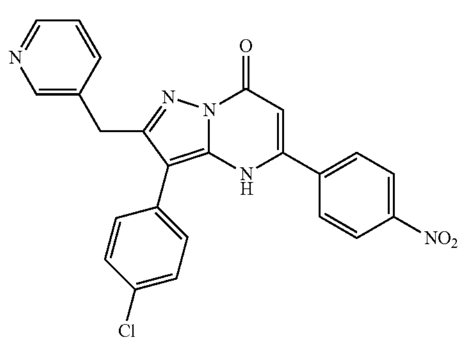 [SMILES: O=c1cc(-c2ccc([N+](=O)[O-])cc2)[nH]c2c(-c3ccc(Cl)cc3)c(Cc3cccnc3)nn12] | 2.8 | 4.8 |

TABLE 1-continued
Exemplary Compounds of Formula I
| Compound Number | Compound Structure | IC50 (μM) 20 nM Arf6 | IC50 (μM) 200 nM Arf6 |
|---|---|---|---|
| 53 | 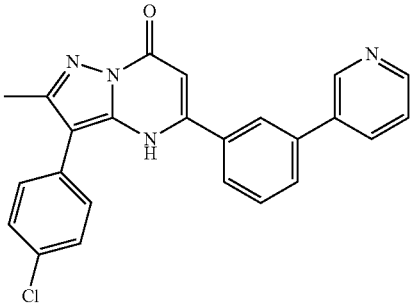 [SMILES: Cc1nn2c(=O)cc(-c3cccc(-c4cccnc4)c3)[nH]c2c1-c1ccc(Cl)cc1] | 3 | |
| 54 | 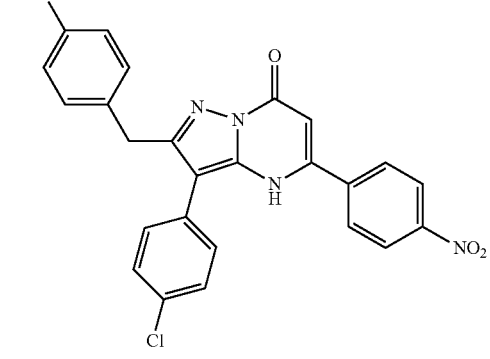 | 3 | |
| 55 | 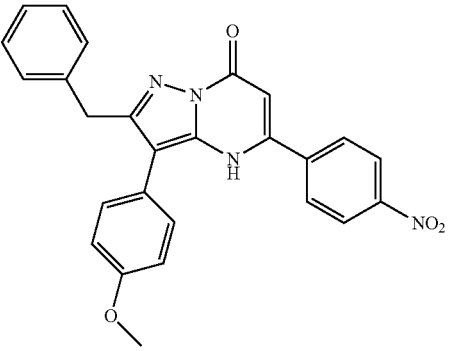 [SMILES: COc1ccc(-c2c(Cc3ccccc3)nn3c(=O)cc(-c4ccc([N+](=O)[O-])cc4)[nH]c23)cc1] | 3.1 | |
| 56 | 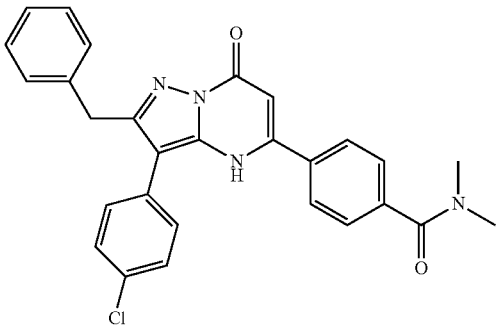 [SMILES: CN(C)C(=O)c1ccc(-c2cc(=O)n3nc(Cc4ccccc4)c(-c4ccc(Cl)cc4)c3[nH]2)cc1] | 3.2 | 2.6 |

TABLE 1-continued

Exemplary Compounds of Formula I

| Compound Number | Compound Structure | IC50 (µM) 20 nM Arf6 | IC50 (µM) 200 nM Arf6 |
|---|---|---|---|
| 57 | 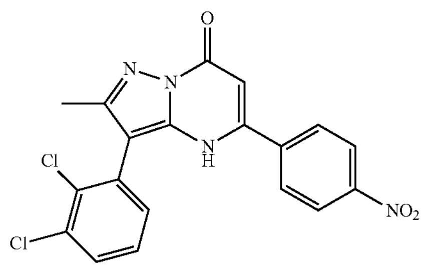 [SMILES: Cc1nn2c(=O)cc(-c3ccc([N+](=O)[O-])cc3)[nH]c2c1-c1cccc(Cl)c1Cl] | 3.2 | |
| 58 | 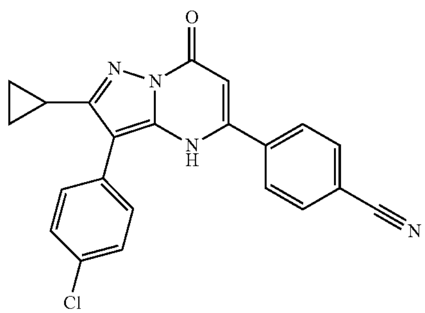 [SMILES: N#Cc1ccc(-c2cc(=O)n3nc(C4CC4)c(-c4ccc(Cl)cc4)c3[nH]2)cc1] | 3.2 | |
| 59 | 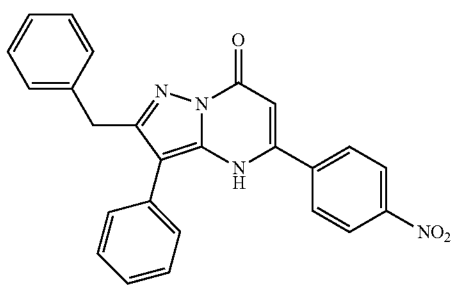 [SMILES: O=c1cc(-c2ccc([N+](=O)[O-])cc2)[nH]c2c(-c3ccccc3)c(Cc3ccccc3)nn12] | 3.2 | |
| 60 | 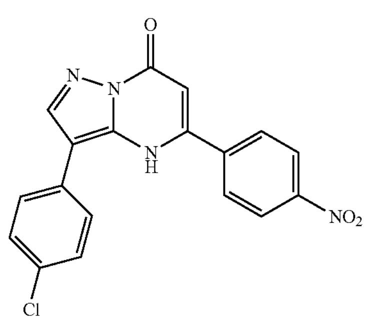 [SMILES: O=c1cc(-c2ccc([N+](=O)[O-])cc2)[nH]c2c(-c3ccc(Cl)cc3)cnn12] | 3.2 | |
| 61 | 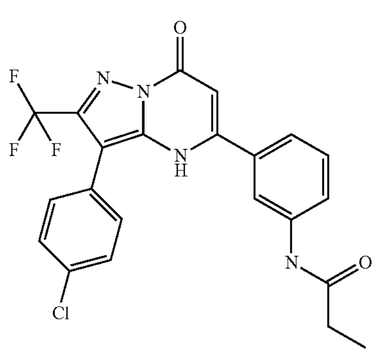 [SMILES: CCC(=O)Nc1cccc(-c2cc(=O)n3nc(C(F)(F)F)c(-c4ccc(Cl)cc4)c3[nH]2)c1] | 3.3 | |

TABLE 1-continued
Exemplary Compounds of Formula I
| Compound Number | Compound Structure | IC50 (μM) 20 nM Arf6 | IC50 (μM) 200 nM Arf6 |
|---|---|---|---|
| 62 | 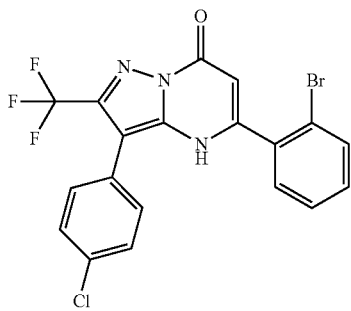 [SMILES: O=c1cc(-c2ccccc2Br)[nH]c2c(-c3ccc(Cl)cc3)c(C(F)(F)F)nn12] | 3.3 | |
| 63 | 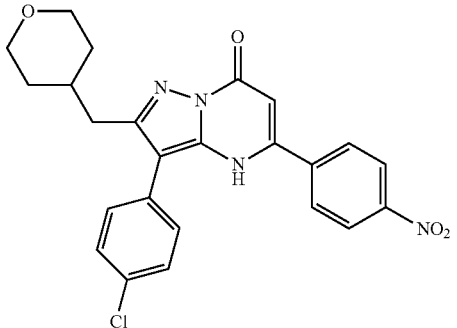 | 3.6 | |
| 64 | 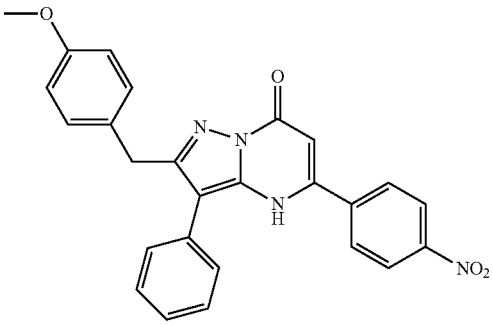 [SMILES: COc1ccc(Cc2nn3c(=O)cc(-c4ccc([N+](=O)[O-])cc4)[nH]c3c2-c2ccccc2)cc1] | 3.6 | |
| 65 | 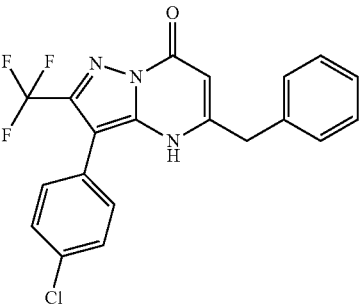 [SMILES: O=c1cc(Cc2ccccc2)[nH]c2c(-c3ccc(Cl)cc3)c(C(F)(F)F)nn12] | 3.7 | 4.9 |

TABLE 1-continued

Exemplary Compounds of Formula I

| Compound Number | Compound Structure | IC50 (µM) 20 nM Arf6 | IC50 (µM) 200 nM Arf6 |
|---|---|---|---|
| 66 | 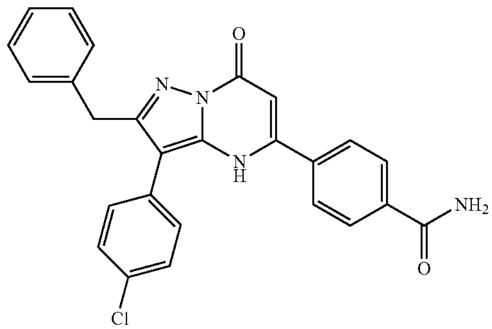 [SMILES: NC(=O)c1ccc(-c2cc(=O)n3nc(Cc4ccccc4)c(-c4ccc(Cl)cc4)c3[nH]2)cc1] | 3.7 | 2.8 |
| 67 | 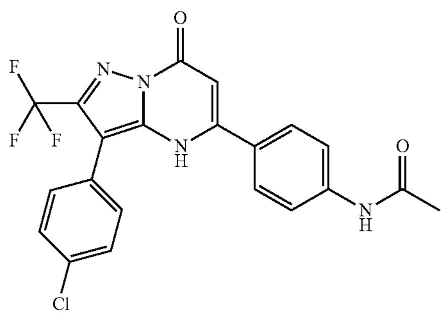 [SMILES: CC(=O)Nc1ccc(-c2cc(=O)n3nc(C(F)(F)F)c(-c4ccc(Cl)cc4)c3[nH]2)cc1] | 3.7 | |
| 68 | 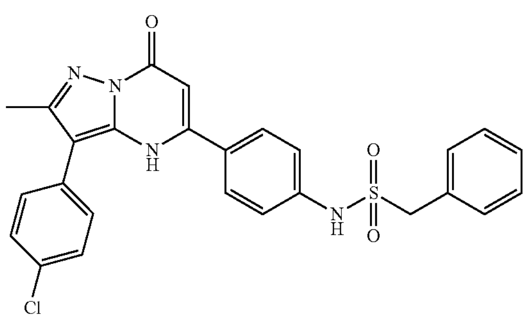 [SMILES: Cc1nn2c(=O)cc(-c3ccc(NS(=O)(=O)Cc4ccccc4)cc3)[nH]c2c1-c1ccc(Cl)cc1] | 3.8 | |
| 69 | 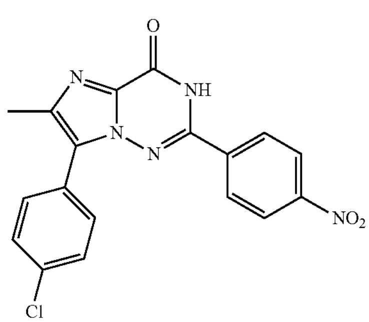 [SMILES: Cc1nc2c(=O)[nH]c(-c3ccc([N+](=O)[O-])cc3)nn2c1-c1ccc(Cl)cc1] | 4 | |

TABLE 1-continued

Exemplary Compounds of Formula I

| Compound Number | Compound Structure | IC50 (μM) 20 nM Arf6 | IC50 (μM) 200 nM Arf6 |
|---|---|---|---|
| 70 | 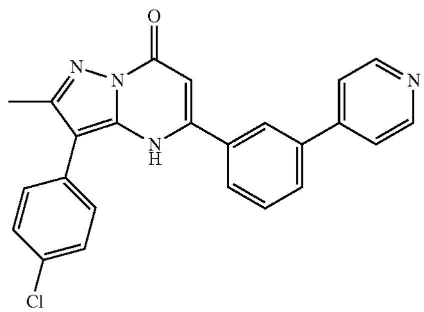 [SMILES: Cc1nn2c(=O)cc(-c3cccc(-c4ccncc4)c3)[nH]c2c1-c1ccc(Cl)cc1] | 4.1 | |
| 71 | 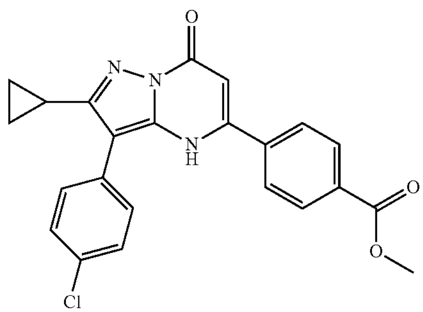 [SMILES: COC(=O)c1ccc(-c2cc(=O)n3nc(C4CC4)c(-c4ccc(Cl)cc4)c3[nH]2)cc1] | 4.1 | |
| 72 | 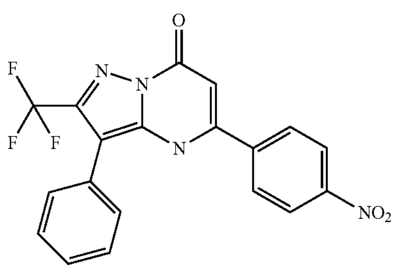 [SMILES: O=c1cc(-c2ccc([N+](=O)[O-])cc2)[nH]c2c(-c3ccccc3)c(C(F)(F)F)nn12] | 4.2 | 3.8 |
| 73 | 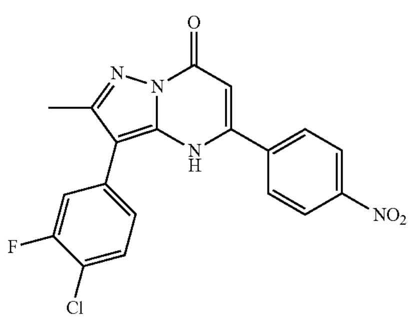 [SMILES: Cc1nn2c(=O)cc(-c3ccc([N+](=O)[O-])cc3)[nH]c2c1-c1ccc(Cl)c(F)c1] | 4.2 | |
| 74 | 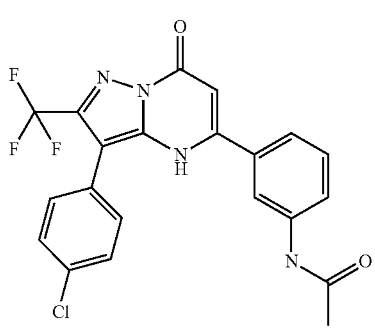 [SMILES: CC(=O)Nc1cccc(-c2cc(=O)n3nc(C(F)(F)F)c(-c4ccc(Cl)cc4)c3[nH]2)c1] | 4.3 | |

TABLE 1-continued

Exemplary Compounds of Formula I

| Compound Number | Compound Structure | IC50 (μM) 20 nM Arf6 | IC50 (μM) 200 nM Arf6 |
|---|---|---|---|
| 75 | 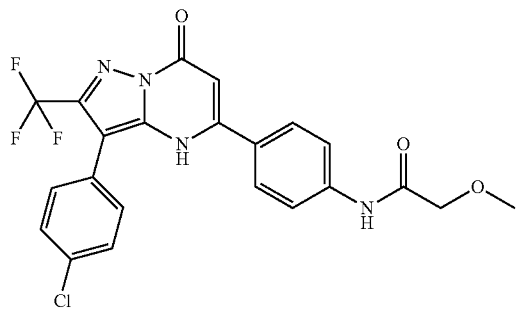 [SMILES: COCC(=O)Nc1ccc(-c2cc(=O)n3nc(C(F)(F)F)c(-c4ccc(Cl)cc4)c3[nH]2)cc1] | | 4.4 |
| 76 | 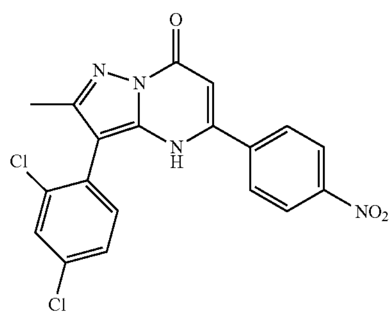 [SMILES: Cc1nn2c(=O)cc(-c3ccc([N+](=O)[O-])cc3)[nH]c2c1-c1ccc(Cl)cc1Cl] | | 4.5 |
| 77 | 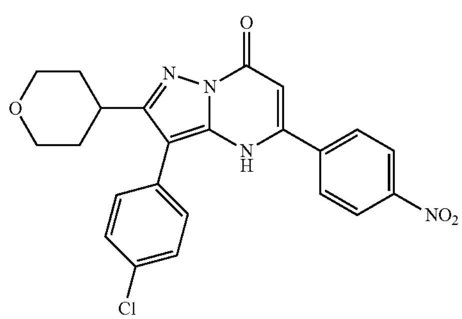 [SMILES: O=c1cc(-c2ccc([N+](=O)[O-])cc2)[nH]c2c(-c3ccc(Cl)cc3)c(C3CCOCC3)nn12] | | 5.1 |
| 78 | 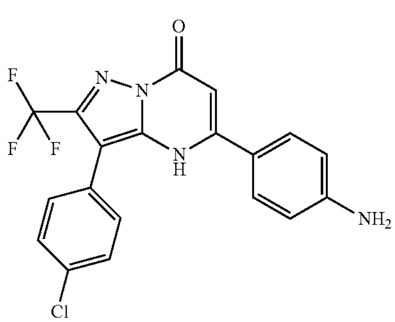 [SMILES: Nc1ccc(-c2cc(=O)n3nc(C(F)(F)F)c(-c4ccc(Cl)cc4)c3[nH]2)cc1] | | 5.2 |

TABLE 1-continued
Exemplary Compounds of Formula I
| Compound Number | Compound Structure | IC50 (μM) 20 nM Arf6 | IC50 (μM) 200 nM Arf6 |
|---|---|---|---|
| 79 | 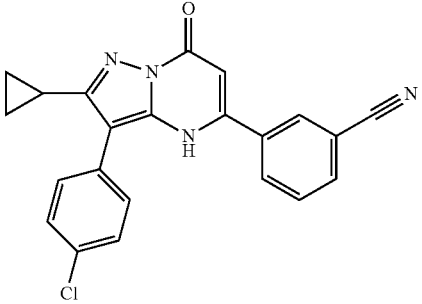 [SMILES: N#Cc1cccc(-c2cc(=O)n3nc(C4CC4)c(-c4ccc(Cl)cc4)c3[nH]2)c1] | 5.5 | |
| 80 | 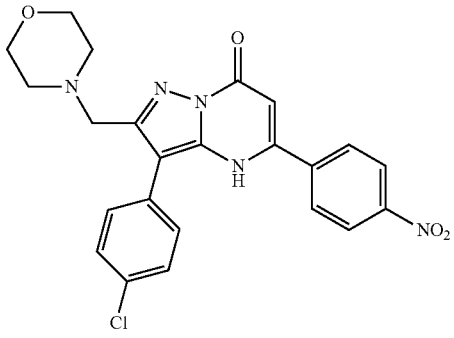 [SMILES: O=c1cc(-c2ccc([N+](=O)[O-])cc2)[nH]c2c(-c3ccc(Cl)cc3)c(CN3CCOCC3)nn12] | 5.9 | |
| 81 | 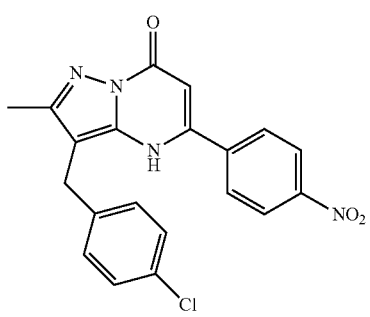 [SMILES: Cc1nn2c(=O)cc(-c3ccc([N+](=O)[O-])cc3)[nH]c2c1Cc1ccc(Cl)cc1] | 6 | |
| 82 | 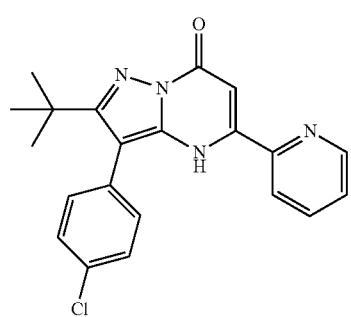 [SMILES: CC(C)(C)c1nn2c(=O)cc(-c3ccccn3)[nH]c2c1-c1ccc(Cl)cc1] | 6 | |

TABLE 1-continued

Exemplary Compounds of Formula I

| Compound Number | Compound Structure | IC50 (μM) 20 nM Arf6 | IC50 (μM) 200 nM Arf6 |
|---|---|---|---|
| 83 | 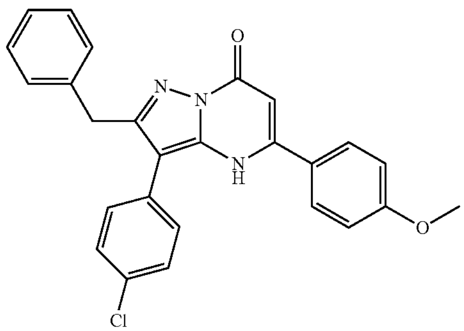 [SMILES: COc1ccc(-c2cc(=O)n3nc(Cc4ccccc4)c(-c4ccc(Cl)cc4)c3[nH]2)cc1] | | 6.2 |
| 84 | 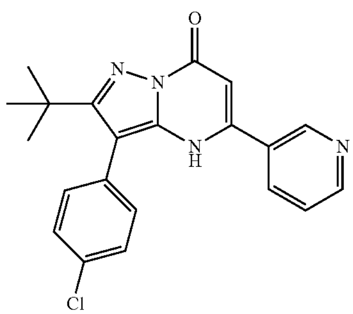 [SMILES: CC(C)(C)c1nn2c(=O)cc(-c3cccnc3)[nH]c2c1-c1ccc(Cl)cc1] | | 6.4 |
| 85 | 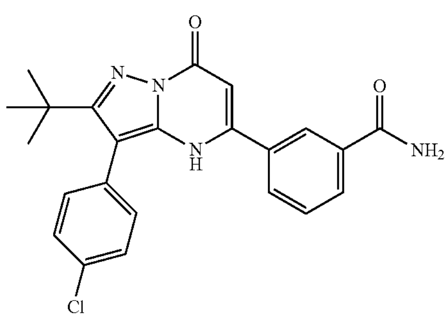 [SMILES: CC(C)(C)c1nn2c(=O)cc(-c3cccc(C(N)=O)c3)[nH]c2c1-c1ccc(Cl)cc1] | | 6.6 |
| 86 | 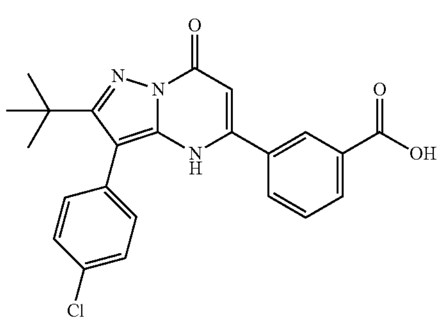 [SMILES: CC(C)(C)c1nn2c(=O)cc(-c3cccc(C(=O)O)c3)[nH]c2c1-c1ccc(Cl)cc1] | | 6.6 |

TABLE 1-continued

Exemplary Compounds of Formula I

| Compound Number | Compound Structure | IC50 (μM) 20 nM Arf6 | IC50 (μM) 200 nM Arf6 |
|---|---|---|---|
| 87 | 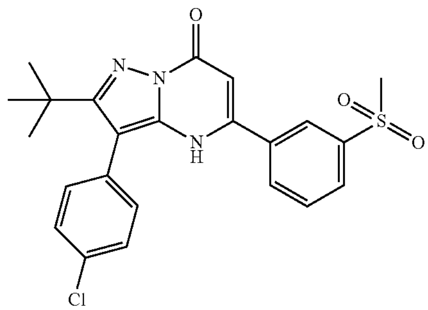 [SMILES: CC(C)(C)c1nn2c(=O)cc(-c3cccc(S(C)(=O)=O)c3)[nH]c2c1-c1ccc(Cl)cc1] | 6.7 | |
| 88 | 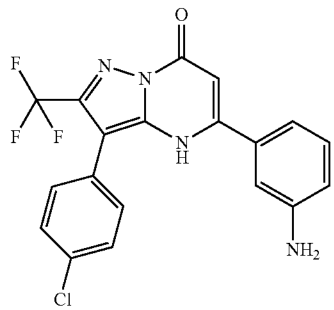 [SMILES: Nc1cccc(-c2cc(=O)n3nc(C(F)(F)F)c(-c4ccc(Cl)cc4)c3[nH]2)c1] | 7 | |
| 89 | 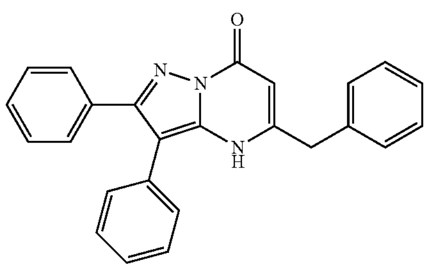 [SMILES: O=c1cc(Cc2ccccc2)[nH]c2c(-c3ccccc3)c(-c3ccccc3)nn12] | 7 | |
| 90 | 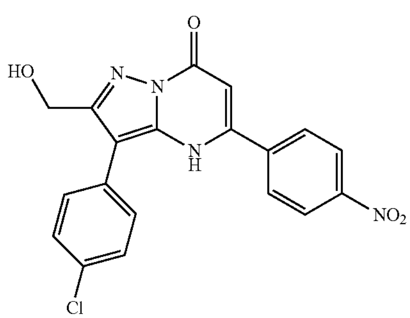 [SMILES: O=c1cc(-c2ccc([N+](=O)[O-])cc2)[nH]c2c(-c3ccc(Cl)cc3)c(CO)nn12] | 7.8 | |
| 91 | 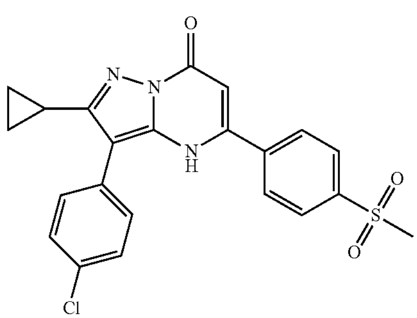 [SMILES: CS(=O)(=O)c1ccc(-c2cc(=O)n3nc(C4CC4)c(-c4ccc(Cl)cc4)c3[nH]2)cc1] | 7.9 | |

TABLE 1-continued

Exemplary Compounds of Formula I

| Compound Number | Compound Structure | IC50 (μM) 20 nM Arf6 | IC50 (μM) 200 nM Arf6 |
|---|---|---|---|
| 92 | 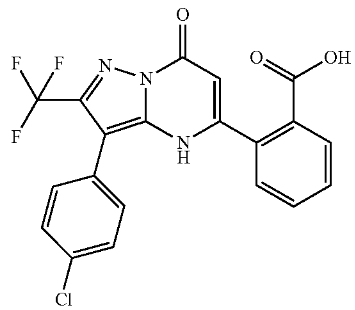 [SMILES: O=C(O)c1ccccc1-c1cc(=O)n2nc(C(F)(F)F)c(-c3ccc(Cl)cc3)c2[nH]1] | 8.1 | |
| 93 | 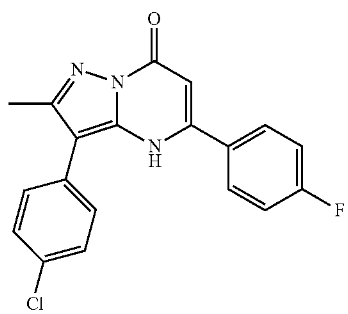 [SMILES: Cc1nn2c(=O)cc(-c3ccc(F)cc3)[nH]c2c1-c1ccc(Cl)cc1] | 8.2 | |
| 94 | 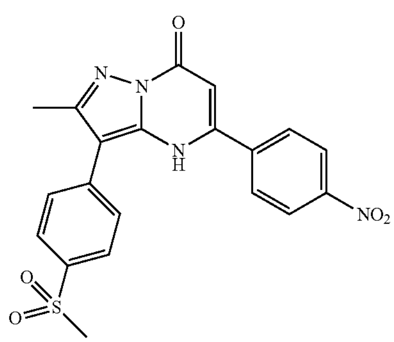 [SMILES: Cc1nn2c(=O)cc(-c3ccc([N+](=O)[O-])cc3)[nH]c2c1-c1ccc(S(C)(=O)=O)cc1] | 8.8 | |
| 95 | 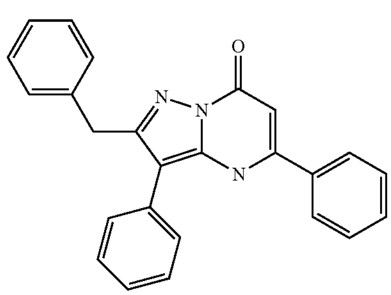 [SMILES: O=c1cc(-c2ccccc2)[nH]c2c(-c3ccccc3)c(Cc3ccccc3)nn12] | 9.4 | |

TABLE 1-continued

Exemplary Compounds of Formula I

| Compound Number | Compound Structure | IC50 (μM) 20 nM Arf6 | IC50 (μM) 200 nM Arf6 |
|---|---|---|---|
| 96 | 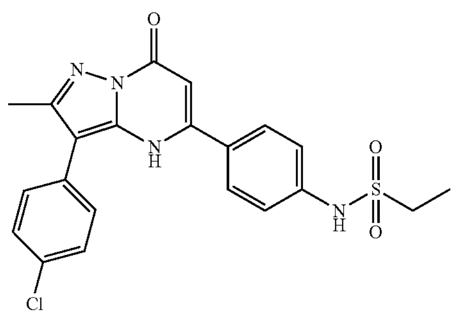 [SMILES: CCS(=O)(=O)Nc1ccc(-c2cc(=O)n3nc(C)c(-c4ccc(Cl)cc4)c3[nH]2)cc1] | 10 | |
| 97 | 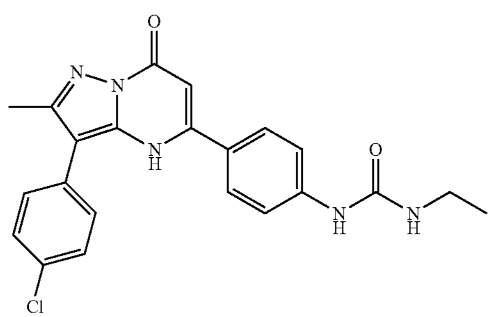 [SMILES: CCNC(=O)Nc1ccc(-c2cc(=O)n3nc(C)c(-c4ccc(Cl)cc4)c3[nH]2)cc1] | 11 | |
| 98 | 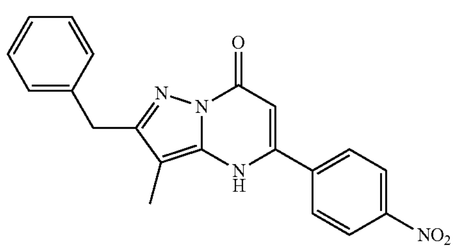 [SMILES: Cc1c(Cc2ccccc2)nn2c(=O)cc(-c3ccc([N+](=O)[O-])cc3)[nH]c12] | 11 | |
| 99 | 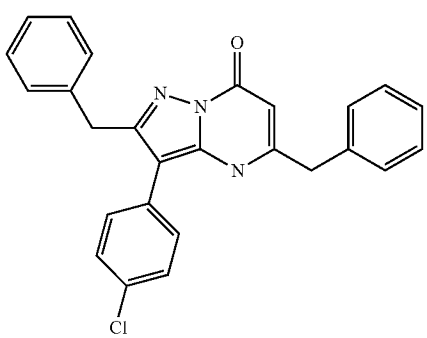 [SMILES: O=c1cc(Cc2ccccc2)[nH]c2c(-c3ccc(Cl)cc3)c(Cc3ccccc3)nn12] | 11 | |
| 100 | 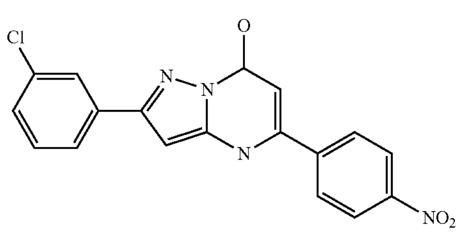 [SMILES: O=[N+]([O-])c1ccc(C2=CC(O)n3nc(-c4cccc(Cl)c4)cc3N2)cc1] | 13 | 10 |

TABLE 1-continued
Exemplary Compounds of Formula I
| Compound Number | Compound Structure | IC50 (µM) 20 nM Arf6 | IC50 (µM) 200 nM Arf6 |
|---|---|---|---|
| 101 | 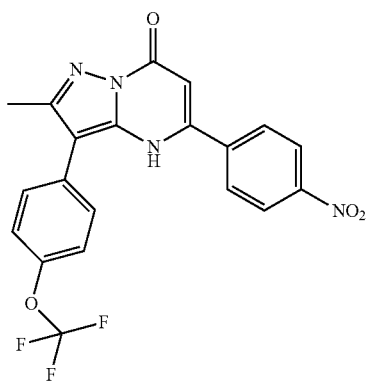 [SMILES: Cc1nn2c(=O)cc(-c3ccc([N+](=O)[O-])cc3)[nH]c2c1-c1ccc(OC(F)(F)F)cc1] | 13 | |
| 102 | 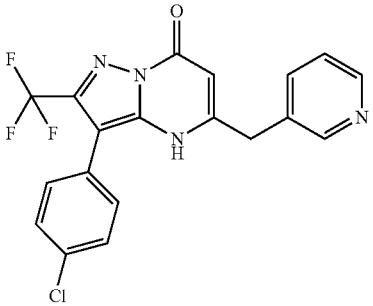 [SMILES: O=c1cc(Cc2cccnc2)[nH]c2c(-c3ccc(Cl)cc3)c(C(F)(F)F)nn12] | 14 | 17 |
| 103 | 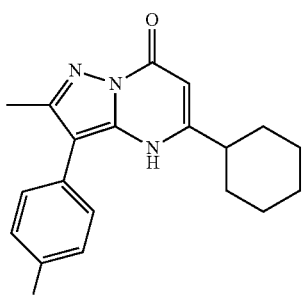 | 14 | |
| 104 | 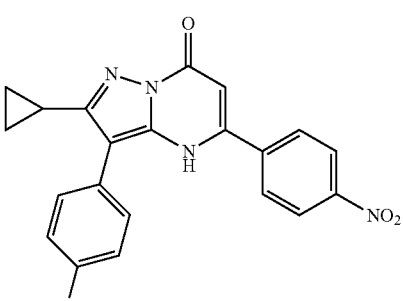 | 14 | |

TABLE 1-continued
Exemplary Compounds of Formula I
| Compound Number | Compound Structure | IC50 (μM) 20 nM Arf6 | IC50 (μM) 200 nM Arf6 |
|---|---|---|---|
| 105 | 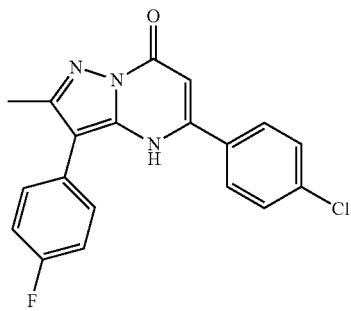 [SMILES: Cc1nn2c(=O)cc(-c3ccc(Cl)cc3)[nH]c2c1-c1ccc(F)cc1] | | 15 |
| 106 | 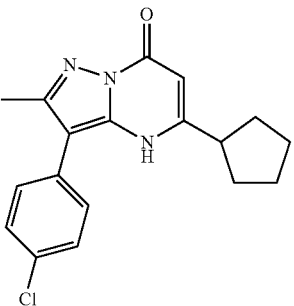 [SMILES: Cc1nn2c(=O)cc(C3CCCC3)[nH]c2c1-c1ccc(Cl)cc1] | | 16 |
| 107 | 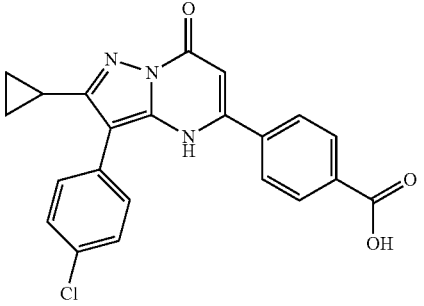 [SMILES: O=C(O)c1ccc(-c2cc(=O)n3nc(C4CC4)c(-c4ccc(Cl)cc4)c3[nH]2)cc1] | | 16 |
| 108 | 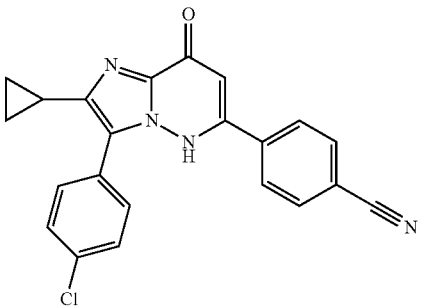 [SMILES: N#Cc1ccc(-c2cc(=O)c3nc(C4CC4)c(-c4ccc(Cl)cc4)n3[nH]2)cc1] | | 16 |

TABLE 1-continued

Exemplary Compounds of Formula I

| Compound Number | Compound Structure | IC50 (μM) 20 nM Arf6 | IC50 (μM) 200 nM Arf6 |
|---|---|---|---|
| 109 | 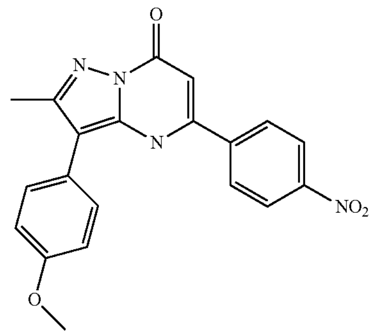 [SMILES: COc1ccc(-c2c(C)nn3c(=O)cc(-c4ccc([N+](=O)[O-])cc4)[nH]c23)cc1] | | 17 |
| 110 | 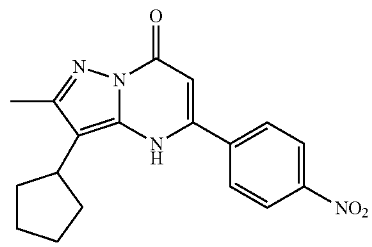 [SMILES: Cc1nn2c(=O)cc(-c3ccc([N+](=O)[O-])cc3)[nH]c2c1C1CCCC1] | | 19 |
| 111 | 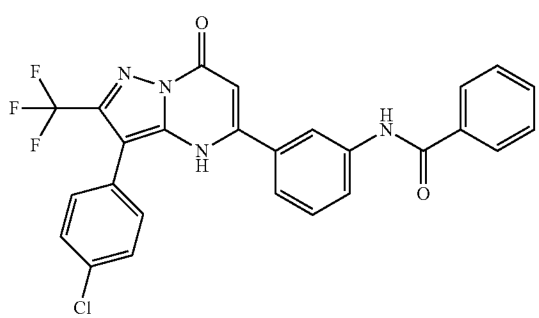 [SMILES: O=C(Nc1cccc(-c2cc(=O)n3nc(C(F)(F)F)c(-c4ccc(Cl)cc4)c3[nH]2)c1)c1ccccc1] | | 20 |
| 112 | 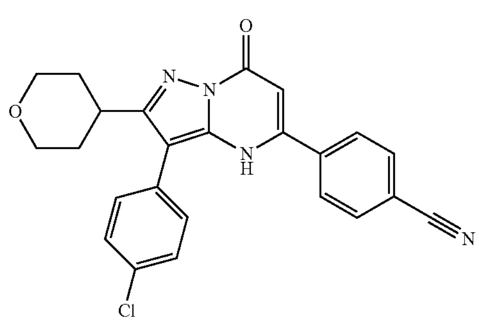 [SMILES: N#Cc1ccc(-c2cc(=O)n3nc(C4CCOCC4)c(-c4ccc(Cl)cc4)c3[nH]2)cc1] | | 20 |

Additional compounds with Arf6 activity can include the compounds shown in Table 2, analogs thereof, and pharmaceutically acceptable salts thereof.

TABLE 2
Additional Exemplary Compounds
| Compound Number | Compound Structure | IC50 (μM) 20 nM Arf6 | IC50 (μM) 200 nM Arf6 |
|---|---|---|---|
| 113 | 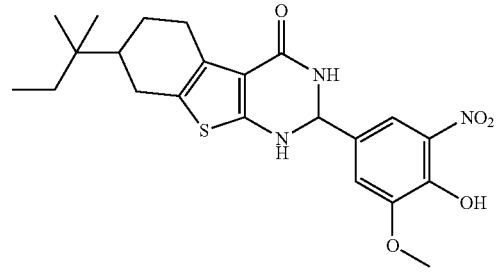 [SMILES: CCC(C)(C)C1CCc2c(sc3c2C(=O)NC(c2cc(OC)c(O)c([N+](=O)[O-])c2)N3)C1] | | 0.56 |
| 114 | 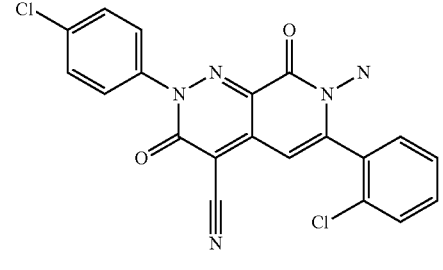 [SMILES: N#Cc1c(=O)n(-c2ccc(Cl)cc2)nc2c(=O)n(N)c(-c3ccccc3Cl)cc12] | | 1.1 |
| 115 | 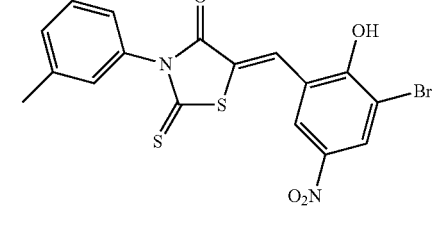 | | 1.1 |
| 116 | 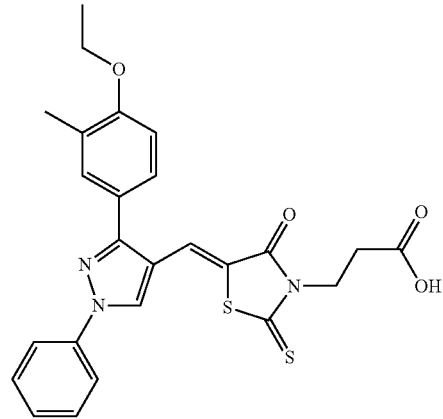 [SMILES: CCOc1ccc(-c2nn(-c3ccccc3)cc2/C=C2\SC(=S)N(CCC(=O)O)C2=O)cc1C] | | 1.4 |

TABLE 2-continued
Additional Exemplary Compounds
| Compound Number | Compound Structure | IC50 (µM) 20 nM Arf6 | IC50 (µM) 200 nM Arf6 |
|---|---|---|---|
| 117 | 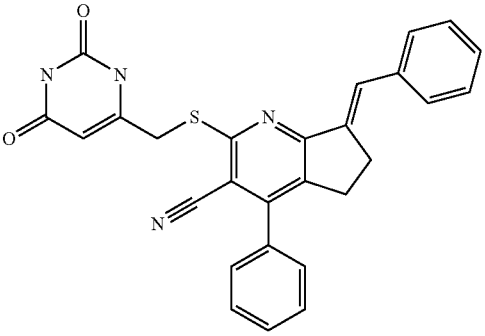 [SMILES: N#Cc1c(SCc2cc(=O)[nH]c(=O)[nH]2)nc2c(c1-c1ccccc1)CC/C2=C\c1ccccc1] | | 1.5 |
| 118 | 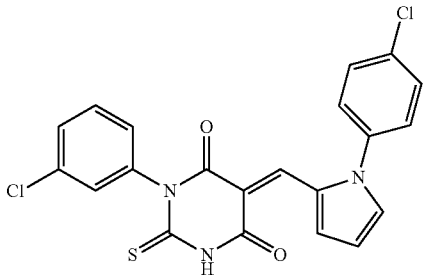 [SMILES: O=C1NC(=S)N(c2cccc(Cl)c2)C(=O)/C1=C/c1cccn1-c1ccc(Cl)cc1] | | 1.8 |
| 119 | 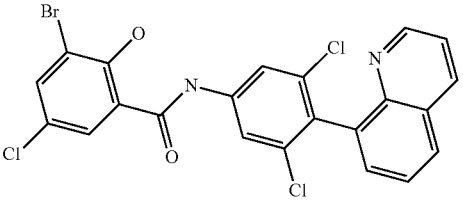 [SMILES: O=C(Nc1cc(Cl)c(-c2cccc3cccnc23)c(Cl)c1)c1cc(Cl)cc(Br)c1O] | | 2.1 |
| 120 | 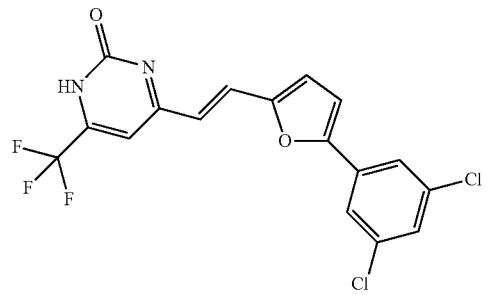 [SMILES: O=c1nc(/C=C/c2ccc(-c3cc(Cl)cc(Cl)c3)o2)cc(C(F)(F)F)[nH]1] | | 3.4 |
| 121 | 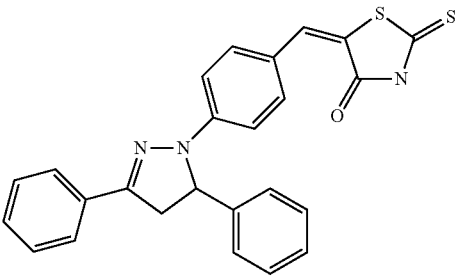 [SMILES: O=C1NC(=S)S/C1=C/c1ccc(N2N=C(c3ccccc3)CC2c2ccccc2)cc1] | | 3.7 |

TABLE 2-continued
Additional Exemplary Compounds
| Compound Number | Compound Structure | IC50 (μM) 20 nM Arf6 | IC50 (μM) 200 nM Arf6 |
|---|---|---|---|
| 122 | 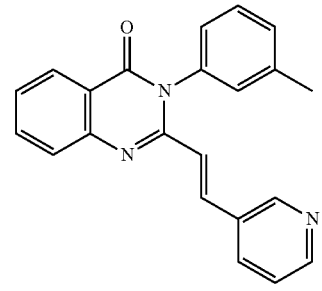 [SMILES: Cc1cccc(-n2c(/C=C/c3cccnc3)nc3ccccc3c2=O)c1] | | 4.7 |
| 123 | 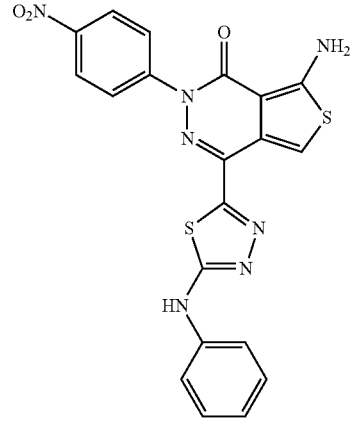 [SMILES: Nc1scc2c(-c3nnc(Nc4ccccc4)s3)nn(-c3ccc([N+](=O)[O-])cc3)c(=O)c12] | | 5.1 |
| 124 | 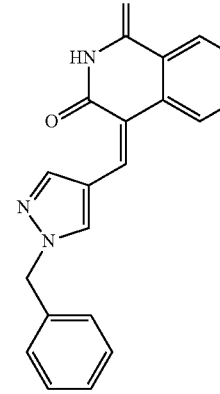 | | 5.4 |

TABLE 2-continued
Additional Exemplary Compounds
| Compound Number | Compound Structure | IC50 (μM) 20 nM Arf6 | IC50 (μM) 200 nM Arf6 |
|---|---|---|---|
| 125 | 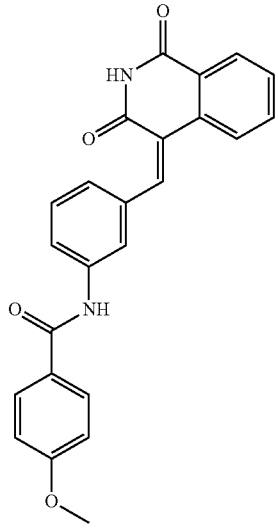 [SMILES: COc1ccc(C(=O)Nc2cccc(/C=C3\C(=O)NC(=O)c4ccccc43)c2)cc1] | | 6.5 |
| 126 | 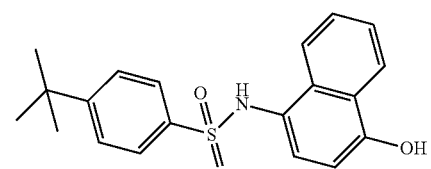 | | 6.7 |
| 127 | 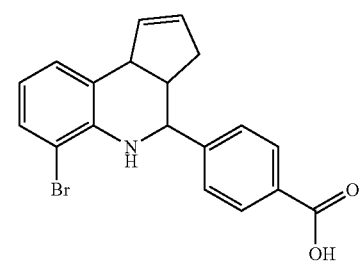 [SMILES: O=C(O)c1ccc(C2Nc3c(Br)cccc3C3C=CCC32)cc1] | | 8 |
| 128 | 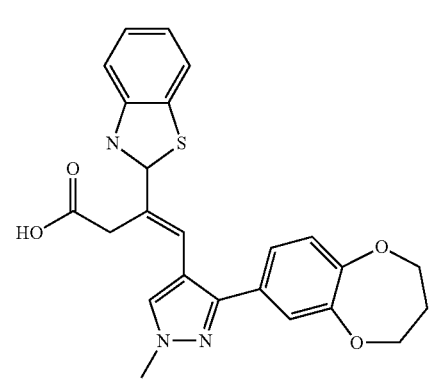 [SMILES: Cn1cc(/C=C(\CC(=O)O)C2Nc3ccccc3S2)c(-c2ccc3c(c2)OCCCO3)n1] | | 8.4 |

TABLE 2-continued
Additional Exemplary Compounds
| Compound Number | Compound Structure | IC50 (μM) 20 nM Arf6 | IC50 (μM) 200 nM Arf6 |
|---|---|---|---|
| 129 | 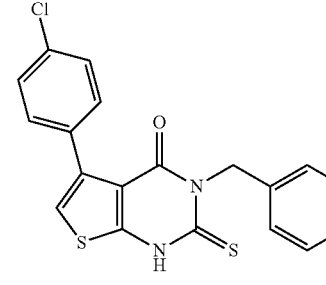 | | 9.7 |
| 130 | 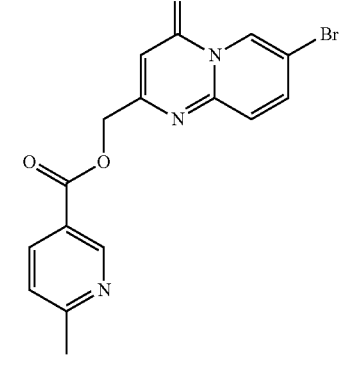 | | 9.9 |
| 131 | 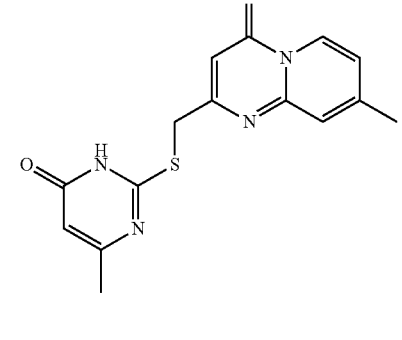 | | 11 |
| 132 | 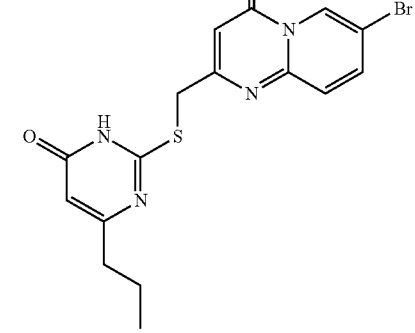 | | 30 |

TABLE 2-continued

Additional Exemplary Compounds

| Compound Number | Compound Structure | IC50 (μM) 20 nM Arf6 | IC50 (μM) 200 nM Arf6 |
|---|---|---|---|
| 133 | 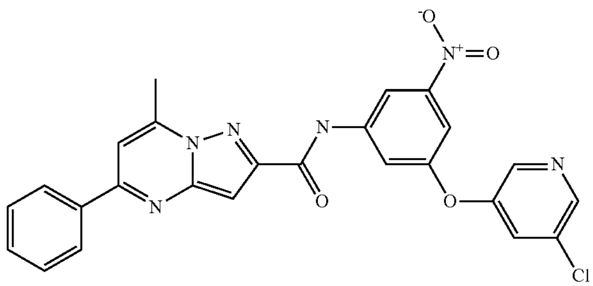 | | 13 |
| 134 | 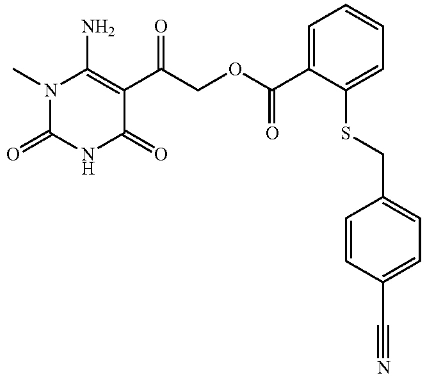 [SMILES: Cn1c(N)c(C(=O)COC(=O)c2ccccc2SCc2ccc(C#N)cc2)c(=O)[nH]c1=O] | | 13 |
| 135 | 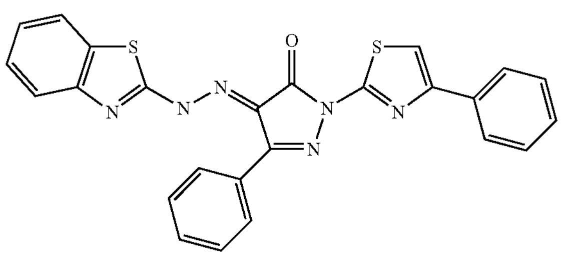 [SMILES: O=C1/C(=N/Nc2nc3ccccc3s2)C(c2ccccc2)=NN1c1nc(-c2ccccc2)cs1] | | 16 |
| 136 | 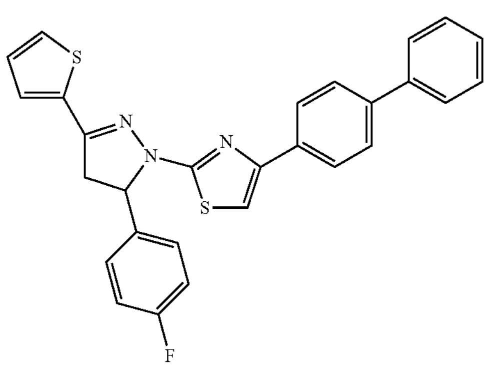 [SMILES: Fc1ccc(C2CC(c3cccs3)=NN2c2nc(-c3ccc(-c4ccccc4)cc3)cs2)cc1] | | 16 |

TABLE 2-continued

Additional Exemplary Compounds

| Compound Number | Compound Structure | IC50 (μM) 20 nM Arf6 | IC50 (μM) 200 nM Arf6 |
|---|---|---|---|
| 137 | 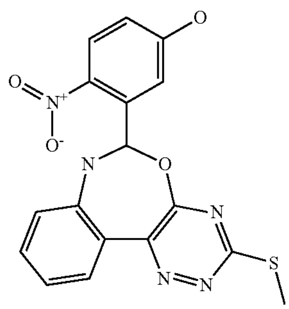 [SMILES: CSc1nnc2c(n1)OC(c1cc(O)ccc1[N+](=O)[O-])Nc1ccccc1-2] | | 17 |
| 138 | 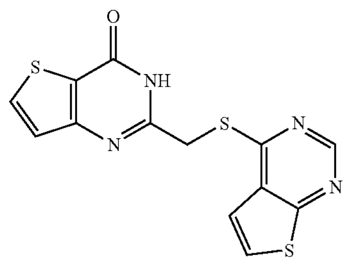 [SMILES: O=c1[nH]c(CSc2ncnc3sccc23)nc2ccsc12] | | 17 |
| 139 | 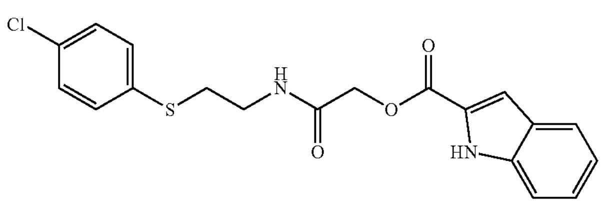 [SMILES: O=C(COC(=O)c1cc2ccccc2[nH]1)NCCSc1ccc(Cl)cc1] | | 19 |
| 140 | 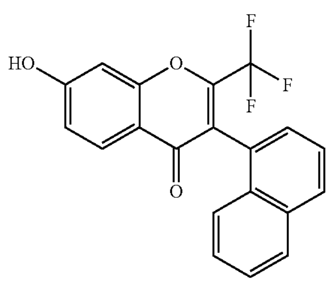 [SMILES: O=c1c(-c2cccc3ccccc23)c(C(F)(F)F)oc2cc(O)ccc12] | | 29 |
| 141 | 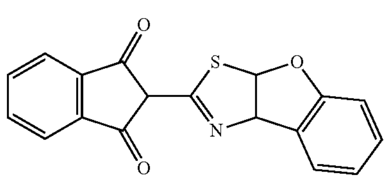 [SMILES: O=C1c2ccccc2C(=O)C1C1=NC2c3ccccc3OC2S1] | | 31 |
| 142 | 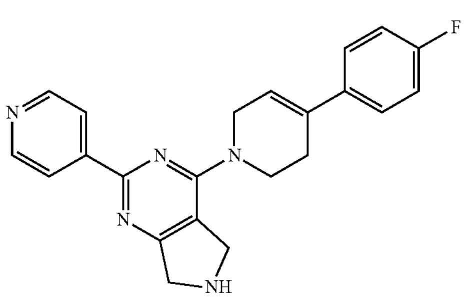 [SMILES: Fc1ccc(C2=CCN(c3nc(-c4ccncc4)nc4c3CNC4)CC2)cc1] | | 1.2 |

TABLE 2-continued

Additional Exemplary Compounds

| Compound Number | Compound Structure | IC50 (μM) 20 nM Arf6 | IC50 (μM) 200 nM Arf6 |
|---|---|---|---|
| 143 | 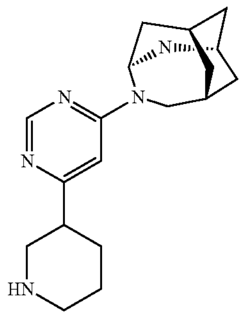 [SMILES: c1nc(C2CCCNC2)cc(N2C[C@@H]3C[C@@H]4C[C@H](C3)N[C@@H]2C4)n1] | | |
| 144 | 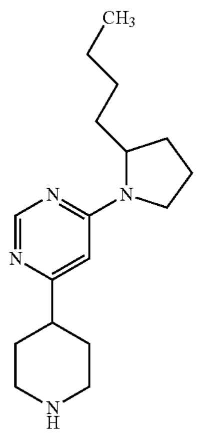 [SMILES: CCCCC1CCCN1c1cc(C2CCNCC2)ncn1] | | |

Certain embodiments of the compounds disclosed herein comprise compounds with $IC_{50}$ values less than about 50 μM. Other embodiments comprise compounds with $IC_{50}$ values less than about 15 μM. Certain other embodiments comprise compounds with $IC_{50}$ values less than about 10 μM, less than about 5 μM, or less than about 1 μM.

In certain embodiments, Compound Number 143 inhibited Arf6 (20 nM assay) by about 31% at 10 μM concentration (20 nM assay). In various embodiments, Compound Number 144 inhibited Arf6 (20 nM assay) by about 35% at 10 μM concentration (20 nM assay).

Protected derivatives of the disclosed compounds also are contemplated. A variety of suitable protecting groups for use with the compounds herein are disclosed. Other conventional protecting groups can be selected by those of skill in the art in consultation with, for example, Greene and Wuts, Protective Groups in Organic Synthesis; 3rd Ed.; John Wiley & Sons, New York, 1999.

The compounds of the present disclosure may be prepared in a variety of ways known to one skilled in the art of organic synthesis. The compounds of the present disclosure can be synthesized using the methods as described herein, together with synthetic methods known in the art of synthetic organic chemistry or variations thereof as appreciated by those skilled in the art.

The specific examples included herein are for illustrative purposes only and are not to be considered as limiting to this disclosure. Any active agents and reagents used in the following examples are either commercially available or can be prepared according to standard literature procedures by those skilled in the art of organic synthesis. In light of this disclosure, those of skill in the art will recognize that variations of these examples and other examples of the disclosed method would be possible without undue experimentation.

Some of the compounds of Formula I for use in embodiments of the present disclosure may exist as single stereoisomers (i.e., essentially free of other stereoisomers), racemates, and/or mixtures of enantiomers, and/or diastereomers. All such single stereoisomers, racemates, and mixtures thereof are intended to be within the scope of the present disclosure. Generally, the compounds that are optically active are used in a substantially optically pure form. Furthermore, some of the compounds for use in embodiments of the present disclosure can exist as cis and trans geometric isomers. All such isomers and mixtures thereof are intended to be within the scope of the present disclosure.

Additionally, the formulas are intended to cover solvated as well as unsolvated forms of the identified structures. For example, Formula I includes compounds of the indicated structure in both hydrated and non-hydrated forms. Other examples of solvates include the structures in combination with isopropanol, ethanol, methanol, DMSO, ethyl acetate, acetic acid, or ethanolamine.

In addition to compounds of Formula I, some embodiments of the present disclosure may comprise pharmaceutically acceptable prodrugs, pharmaceutically active metabolites, and pharmaceutically acceptable salts of such compounds.

Prodrugs and active metabolites of compound may be identified using routine techniques known in the art (see, e.g., Bertolini, G et al., J. Med. Chem., 40, 2011-2016 (1997); Shan, D. et al., J. Pharm. Sci., 86 (7), 756-767 (1997); Bagshawe K., Drug Dev. Res., 34, 220-230 (1995); Bodor N.; Advance in Drug Res., 13, 224-331 (1984); Bundgaard, H., Design of Prodrugs (Elsevier Press 1985); and Larsen, I. K., Design and Application of Prodrugs, Drug Design and Development (Krogsgaard-Larsen et al., eds., Harwood Academic Publishers, 1991)).

Definitions

It is to be understood that the terminology used herein is for the purpose of describing particular embodiments only, and is not intended to limit the scope of the present disclosure, which will be limited only by the appended claims.

Unless defined otherwise, all technical and scientific terms used herein have the meanings that would be commonly understood by one of skill in the art. As used herein, the singular forms "a", "an," and "the" are intended to include the plural forms as well, unless the context clearly indicates otherwise. Also, as used herein, "and/or" refers to and encompasses any and all possible combinations of one or more of the associated listed items. Furthermore, the term "about," as used herein when referring to a measurable value such as an amount of a compound, dose, time, temperature, and the like, is meant to encompass variations of 50%, 30%, 20%, 10%, 5%, 1%, 0.5%, or even 0.1% of the specified amount. All publications, patent applications, patents, and other references mentioned herein are incorporated by reference in their entirety.

As used herein, the term "alkyl" refers to a saturated aliphatic hydrocarbon including straight chain and branched chain groups. In an embodiment, the alkyl group has 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc. up to and including 20 carbon atoms). In certain embodiments, it is a medium size alkyl having 1 to 10 carbon atoms. In some embodiments, it is a lower alkyl having 1 to 6 carbon atoms, or 1 to 4 carbon atoms. The alkyl group may be substituted or unsubstituted. When substituted, the substituent group(s) may be one or more individually selected from cycloalkyl, aryl, heteroaryl, heteroalicyclic, hydroxy, alkoxy, aryloxy, mercapto, alkylthio, arylthio, cyano, halo, carbonyl, thiocarbonyl, O-carbamyl, N-carbamyl, O-thiocarbamyl, N-thiocarbamyl, C-amido, N-amido, C-carboxy, O-carboxy, cyanato, isocyanato, thiocyanato, isothiocyanato, nitro, silyl, and amino.

As used herein, the term "halo" refers to chloro, fluoro, bromo, and iodo.

As used herein, the term "hydroxy" refers to an —OH group.

As used herein, the term "alkoxy" refers to both an —O-alkyl and an —O-cycloalkyl group, as defined herein. Lower alkoxy refers to —O-lower alkyl groups.

As used herein, the term "aryloxy" refers to both an —O-aryl and an —O-heteroaryl group, as defined herein.

As used herein, the term "alkylthio" group refers to both an S-alkyl and an —S-cycloalkyl group, as defined herein.

As used herein, the term "arylthio" group refers to both an —S-aryl and an —S-heteroaryl group, as defined herein.

As used herein, the term "carbonyl" group refers to a —C(=O)R" group, where R" is selected from the group consisting of hydro, alkyl, cycloalkyl, aryl, heteroaryl (bonded through a ring carbon) and heterocyclic (bonded through a ring carbon), as defined herein.

As used herein, the term "carboxy" group refers to a —C(=O)OR" group with R" as defined above.

As used herein, the term "carboxy salt" refers to a —C(=O)O— M+ group wherein M+ is selected from the group consisting of lithium, sodium, magnesium, calcium, potassium, barium, iron, zinc, and quaternary ammonium.

As used herein, the term "acetyl" group refers to a —C(=O)CH$_3$ group.

As used herein, the term "carboxylic acid" refers to a carboxy group in which R" is hydro.

As used herein, the term "haloalkyl" refers to an alkyl group substituted with 1 to 6 halo groups, and may be a haloalkyl with a —CX$_3$ group wherein X is a halo group. The halo groups can be independently selected.

As used herein, the term "cyano" refers to a —C≡N group.

As used herein, the term "sulfonyl" refers to a —S(=O)$_2$R" group, with R" being hydrogen, alkyl, or lower alkyl.

As used herein, the term "sulfonamido" refers to a —S(=O)$_2$NR"$_2$, with each R" independently selected from hydrogen, alkyl, or lower alkyl.

As used herein, the term "O-carbamyl" refers to a —OC(=O)NR"$_2$ group with each R" independently selected from hydrogen, alkyl, or lower alkyl.

As used herein, the term "N-carbamyl" refers to a —NR"C(=O)NR"$_2$ group, with each R" independently selected from hydrogen, alkyl, or lower alkyl.

As used herein, the term "amino" refers to an —NR"$_2$ group, with each R" independently selected from the group consisting of hydrogen and alkyl.

As used herein, the term "C-amido" refers to a —C(=O)NR"$_2$ group with each R" independently selected from hydrogen, alkyl, or lower alkyl. An "N-amido" refers to a NR"C(=O)R"— group with each R" independently selected from hydrogen, alkyl, or lower alkyl.

As used herein, the term "nitro" refers to a —NO$_2$ group.

As used herein, the term "methylene" refers to a —CH$_2$— group. A substituted methylene group is a methylene group wherein the carbon atom may be substituted with alkyl or cycloalkyl.

As used herein, the term "cycloalkyl" refers to an all-carbon monocyclic or fused alkyl ring (i.e., rings which share an adjacent pair of carbon atoms) group wherein one or more of the rings does not have a completely conjugated pi-electron system. Examples, without limitation, of cycloalkyl groups are cyclopropane, cyclobutane, cyclopentane, cyclopentene, cyclohexane, adamantane, cyclohexadiene, cycloheptane, and cycloheptatriene. A cycloalkyl group may be substituted or unsubstituted. When substituted, the substituent group(s) may be one or more individually selected from alkyl, aryl, heteroaryl, heterocyclic, hydroxy, alkoxy, aryloxy, mercapto, alkylthio, arylthio, cyano, halo, carbonyl, carboxy, O-carbamyl, N-carbamyl, C-amido, N-amido, nitro, and amino.

As used herein, the term "heterocycle" or "heterocyclic" refers to a saturated or partially saturated 3, 4, 5, 6, or 7-membered monocyclic, or 7, 8, 9, or 10-membered bicyclic ring system, which consists of carbon atoms and from one to four heteroatoms independently selected from the group consisting of O, N, and S, wherein the nitrogen and sulfur heteroatoms can be optionally oxidized, the nitrogen can be optionally quaternized, and including any bicyclic group in which any of the above-defined heterocyclic rings is fused to a benzene ring, and wherein the heterocyclic ring can be substituted on carbon or on a nitrogen atom if the resulting compound is stable. Non-limiting saturated or partially saturated heterocyclic groups include tetrahydrofuranyl, pyranyl, piperidinyl, piperazinyl, pyrrolidinyl, imidazolidinyl, imidazolinyl, indolinyl, morpholinyl, pyrazolidinyl, pyrazolinyl, tetronoyl, and tetramoyl groups. Example of "heterocycles" or "heterocyclic" rings also include, but are not limited to, morpholino, pyranyl, piperidyl, piperazinyl, pyrrolidinyl, thiomorpholino, homopiperazinyl, imidazolyl, imidazolidinyl, pyrazolidinyl, dioxanyl, and dioxolanyl. "Heterocycle" can include heteroaryls when the pi-electron system of a heterocycle is completely conjugated.

As used herein, the term "aryl" refers to an all-carbon monocyclic or fused-ring polycyclic (i.e., rings which share adjacent pairs of carbon atoms) groups having a completely conjugated pi-electron system. Examples, without limitation, of aryl groups are phenyl, naphthalenyl, and anthracenyl. The aryl group may be substituted or unsubstituted. When substituted, the substituted group(s) may be one or more selected from halo, trihalomethyl, alkyl, hydroxy, alkoxy, aryloxy, mercapto, alkylthio, arylthio, cyano, nitro, carbonyl, C-carboxy, O-carboxy, C-amido, N-amido, N-alkyl, sulfinyl, sulfonyl, S-sulfonamido, N-sulfonamido, trihalo-methanesulfonamido, and amino.

As used herein, the term "heteroaryl" refers to groups having 5, 6, 7, 8, 9, 10, 11, 12, 13, or 14 ring atoms; 6, 10, or 14 pi electrons shared in a cyclic array; and containing carbon atoms and 1, 2, or 3 oxygen, nitrogen, or sulfur heteroatoms. Non-limiting heteroaryl groups include thienyl (thiophenyl), benzo[b]thienyl, naphtho[2,3-b]thienyl, thianthrenyl, furyl (furanyl), isobenzofuranyl, chromenyl, xanthenyl, phenoxanthinyl, pyrrolyl, including without limitation 2H-pyrrolyl, imidazolyl, pyrazolyl, pyridyl (pyridinyl), including without limitation 2-pyridyl, 3-pyridyl, 4-pyridyl, pyrazinyl, pyrimidinyl, pyridazinyl, pyrido[1,2-a]pyrimidin-4-one, pyrazolo[1,5-a]pyrimidinyl, including without limitation pyrazolo[1,5-a]pyrimidin-3-yl, 1,2-benzoisoxazol-3-yl, benzimidazolyl, 2-oxindolyl, and 2 oxobenzimidazolyl. Where the heteroaryl group contains a nitrogen atom in a ring, such nitrogen atom may be in the form of an N-oxide, e.g., a pyridyl N oxide, pyrazinyl N-oxide, and pyrimidinyl N-oxide. When substituted, the substituted group(s) may be one or more selected from alkyl, cycloalkyl, halo, trihalomethyl, hydroxy, alkoxy, aryloxy, mercapto, alkylthio, arylthio, cyano, nitro, carbonyl, sulfonamido, carboxy, sulfinyl, sulfonyl, 0-carbamyl, N-carbamyl, C-amido, N-amido, and amino.

As used herein, the term "unit dosage form" refers to a physically discrete unit, such as a capsule or tablet suitable as a unitary dosage for a human patient. Each unit contains a predetermined quantity of a compound of Formula I, which was discovered or believed to produce the desired pharmacokinetic profile which yields the desired therapeutic effect. The dosage unit is composed of a compound of Formula I in association with at least one pharmaceutically acceptable carrier, salt, excipient, or combination thereof.

As used herein, the term "dose" or "dosage" refers to the amount of active ingredient that an individual takes or is administered at one time. For example, an 800 mg dose of a compound of Formula I refers to, in the case of a twice-daily dosage regimen, a situation where the individual takes 800 mg of a compound of Formula I twice a day, e.g., 800 mg in the morning and 800 mg in the evening. The 800 mg of a compound of Formula I dose can be divided into two or more dosage units, e.g., two 400 mg dosage units of a compound of Formula I in tablet form or two 400 mg dosage units of a compound of Formula I in capsule form.

"A pharmaceutically acceptable prodrug" is a compound that may be converted under physiological conditions or by solvolysis to the specified compound or to a pharmaceutically acceptable salt of such compound.

"A pharmaceutically active metabolite" is intended to mean a pharmacologically active product produced through metabolism in the body of a specified compound or salt thereof. Metabolites of a compound may be identified using routine techniques known in the art and their activities determined using tests such as those described herein.

"A pharmaceutically acceptable salt" is intended to mean a salt that retains the biological effectiveness of the free acids and bases of the specified compound and that is not biologically or otherwise undesirable. A compound for use in some embodiments of the present disclosure may comprise a sufficiently acidic, a sufficiently basic, or both functional groups, and accordingly react with any of a number of inorganic or organic bases, and inorganic and organic acids, to form a pharmaceutically acceptable salt. Exemplary pharmaceutically acceptable salts include those salts prepared by reaction of the compounds of the present disclosure with a mineral or organic acid or an inorganic base, such as salts including sulfates, pyrosulfates, bisulfates, sulfites, bisulfites, phosphates, monohydrophosphates, dihydrophosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4 dioates, hexyne-1,6-dioates, benzoates, chlorobenzoates, methyl benzoates, dinitrobenzoates, hydroxybenzoates, methoxybenzoates, phthalates, sulfonates, xylenesulfonates, phenylacetates, phenylpropionates, phenylbutyrates, citrates, lactates, gamma-hydroxybutyrates, glycollates, tartrates, methane-sulfonates, propanesulfonates, naphthalene-1-sulfonates, naphthalene-2-sulfonates, and mandelates.

Pharmaceutical compositions are provided herein. Pharmaceutical compositions according to the present description include a pharmaceutically acceptable carrier and a therapeutically effective amount of an active compound according to the present description. The pharmaceutical compositions can take the form of, for example, solutions, suspensions, emulsion, tablets, pills, capsules, powders, sustained-release formulations, or suppositories. Examples of suitable pharmaceutical carriers are described in, for example, Remington's Pharmaceutical Sciences, by E. W. Martin. The pharmaceutical compositions disclosed herein may be prepared for administration by any suitable route known to the skilled artisan including, for example, intravenous, subcutaneous, intramuscular, intradermal, transdermal, intrathecal, intracerebral, intraperitoneal, intransal, epidural, pulmonary, and oral routes. Administration can be immediate or rapid, such as by injection, or carried out over a period of time, such as by infusion or administration of controlled or delayed release formulations.

Where pharmaceutical formulations are prepared for treating tissues in the central nervous system, administration can be by injection or infusion into the cerebrospinal fluid (CSF). Moreover, where pharmaceutical compositions are prepared for delivery to cells or tissues in the central nervous system, the pharmaceutical composition may be formulated to include one or more other carriers or components capable of promoting penetration of the active compound or a derivative of the active compound across the blood-brain barrier.

When prepared for oral administration, the pharmaceutical compositions described herein may be prepared, for example, in capsules, tablets, caplets, lozenges, and aqueous suspensions or solutions. Pharmaceutical compositions described herein prepared for oral administration can be formulated using known carriers, including known fillers, diluents, excipients, binders, surfactants, suspending agents, emulsifiers, lubricants, sweeteners, flavorants, and colorants, suited to formulation of the desired dosage form. Additionally, pharmaceutical compositions as described herein can be prepared using formulation approaches that utilize encapsulation in liposomes, microparticles, microcapsules, receptor-mediated endocytosis (see, e.g., Wu et al. J. Biol. Chem. 262:4429-32, 1987), to facilitate delivery or uptake of the active compound.

Examples of pharmaceutically acceptable carriers include sterile liquids, such as water and oils, including those of petroleum, animal, vegetable or synthetic origin, such as peanut oil, soybean oil, mineral oil, and sesame oil. Aqueous carriers, including water, are typical carriers for pharmaceutical compositions prepared for intravenous administration. As further examples, saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene glycol, water, and ethanol. The composition, if desired, can also contain wetting or emulsifying agents, or pH buffering agents.

The pharmaceutical compositions described herein can be formulated using any of the active compounds described herein, including any pharmaceutically acceptable salts, esters, isomers, or solvates thereof. In certain embodiments, the pharmaceutical compositions described herein include an active compound as described herein, and in alternative embodiments, the pharmaceutical compositions include two or more active compounds according to the present description. The amount of the one or more active compounds included in the pharmaceutical composition will vary, depending upon, for example, the nature and activity of the active compound(s), the nature and composition of the dosage form, and the desired dose to be administered to a subject.

In some instances, it can be desirable to administer the compositions described herein locally to the area in need of treatment. Local administration can be achieved by, for example, and not by way of limitation, local infusion during surgery, topical application (e.g., in conjunction with a wound dressing after surgery), by injection, by means of a catheter, by means of a suppository, or by means of an implant, the implant being of a porous, non-porous, or gelatinous material, including membranes such as silastic membranes, or fibers. In one embodiment, administration can be by direct injection at the site of bacterial infection.

In another embodiment, the agent can be delivered in a vesicle, in particular a liposome. In yet another embodiment, the agent can be delivered in a controlled release system. In one such embodiment, a pump can be used. In another such embodiment, polymeric materials can be used. In yet another such embodiment, a controlled release system can be placed in proximity of the therapeutic target, thus utilizing only a fraction of the systemic dose.

In addition to one or more active compounds as described herein and a pharmaceutical carrier, pharmaceutical compositions according to the present description may include one or more additional therapeutic or prophylactic agents.

It should be understood, however, that a specific dosage and treatment regime for any particular subject or disease state will depend upon a variety of factors, including the age, body weight, general health, gender, diet, time of administration, nature of active compound(s), rate of excretion, drug combination, the judgment of the treating physician, and the severity of the particular disease being treated. Moreover, determination of the amount of a pharmaceutical composition to be administered to a subject will depend upon, among other factors, the amount and specific activity of the active compound(s) included in the pharmaceutical composition and the use or incorporation of additional therapeutic or prophylactic agents or treatment regimes. Determination of therapeutically effective dosages may be based on animal model studies and is typically guided by determining effective dosages and administration protocols that significantly reduce the occurrence or severity of disease in model subjects.

A non-limiting range for a therapeutically effective amount of the active compounds described herein is from about 0.001 mg/kg to about 100 mg/kg body weight per day. For example, pharmaceutical compositions according to the present description can be prepared and administered such that the amount of active compound according to the present description administered to a subject is selected from between about 0.001 mg/kg and about 50 mg/kg, between about 0.01 mg/kg and about 20 mg/kg, between about 0.1 and about 10 mg/kg, and between about 0.1 mg/kg and about 5 mg/kg body weight per day.

In one aspect, there is provided a compound of Formula I:

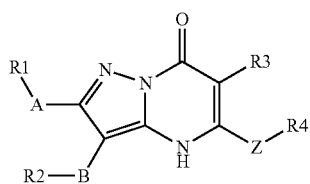

FORMULA I wherein R1 is selected from at least one of hydrogen, hydroxyl, halo, alkyl, alkoxy, haloalkyl, haloalkoxy, cycloalkyl, phenyl, substituted phenyl, pyridyl, morpholino, or pyranyl;
R2 is selected from at least one of hydrogen, alkyl, optionally substituted aryl, cycloalkyl, or sulfonyl;
R3 is selected from at least one of hydrogen, alkyl, or halo;
R4 is selected from at least one of hydrogen, alkyl, optionally substituted aryl, cycloalkyl, or pyridyl;
A, B, and Z are each independently a bond or an optionally substituted methylene; and pharmaceutically acceptable salts thereof.

In an additional aspect, there is provided a method for the treatment or prevention of a disease in a patient suffering from a disease relating to vascular leak, vascular inflammation, and/or angiogenesis including, but not limited to, acute lung injury; influenza-induced acute respiratory distress; sepsis; hemorrhagic fever viruses such as Ebola virus, Marburg virus, hantavirus, and/or dengue virus; age-related macular degeneration; rheumatoid arthritis; or cancer, with an inhibitor of Arf6, the method comprising administering a therapeutically effective amount of a compound which is an Arf6 inhibitor, or a pharmaceutically acceptable salt of the compound thereof.

In another aspect, there is provided a use of the compounds of Formula I or additional compounds having Arf6 activity (i.e., inhibitors, or partial inhibitors, of Arf6), including those shown in Tables 1 and 2, in the treatment or prevention of diseases relating to vascular leak, vascular inflammation, and/or angiogenesis including, but not limited to, acute lung injury; influenza-induced acute respiratory distress; sepsis; hemorrhagic fever viruses such as Ebola virus, Marburg virus, hantavirus, or dengue virus; age-related macular degeneration; rheumatoid arthritis; or cancer.

In yet another aspect there is provided a pharmaceutical composition comprising a compound of Formula I or additional compounds having Arf6 activity, including those shown in Tables 1 and 2, and at least one pharmaceutically acceptable carrier and/or excipient.

In another aspect, there is provided a pharmaceutical composition comprising a therapeutically effective amount of a compound of Formula I or another compound having Arf6 activity, including those shown in Tables 1 and 2, to treat or prevent diseases relating to vascular leak, vascular inflammation, and/or angiogenesis including, but not limited to, acute lung injury; influenza-induced acute respiratory distress; sepsis; hemorrhagic fever viruses such as Ebola virus, Marburg virus, hantavirus, or dengue virus; age-related macular degeneration; rheumatoid arthritis; or cancer; such compositions can comprise a compound of Formula I or another compound having Arf6 activity, including those shown in Tables 1 and 2, in association with one or more pharmaceutically acceptable diluents and/or excipients.

In some embodiments, a method for treating a patient having, or at risk of developing, a disorder relating to vascular leak, vascular inflammation, and/or angiogenesis, may comprise administering to a patient (i.e., a patient in need thereof) an effective amount of a pharmaceutical composition, comprising an Arf6 inhibitor and/or a pharmaceutically acceptable salt of an Arf6 inhibitor In certain embodiments, the pharmaceutical composition may further comprise a pharmaceutically acceptable carrier. Additionally, methods for treating a patient having, or at risk of developing, a disorder relating to vascular leak, vascular inflammation, and/or angiogenesis may comprise reducing a pathological effect or symptom of the disorder relating to vascular leak, vascular inflammation, and/or angiogenesis, or to reduce the risk of developing the disorder relating to vascular leak, vascular inflammation, and/or angiogenesis. In some embodiments, a pathological effect and/or a symptom of the disorder relating to vascular leak, vascular inflammation, and/or angiogenesis may comprise macular degeneration, macular edema, retinopathies, vision loss, edema, respiratory distress, and/or tumorigenesis.

In various embodiments, the disorder relating to vascular leak, vascular inflammation, and/or angiogenesis may be selected from at least one of, but not limited to, an acute lung injury, influenza-induced acute respiratory distress, sepsis, age-related macular degeneration, diabetic retinopathy, macular edema, rheumatoid arthritis, and/or cancer. Further, in various other embodiments, the disorder relating to vascular leak, vascular inflammation, and/or angiogenesis may be a hemorrhagic fever virus infection selected from, but not limited to, at least one of an Ebola virus infection, a Marburg virus infection, a hantavirus infection, and/or a dengue virus infection.

In some embodiments, a method for treating a patient having, or at risk of developing, a disorder relating to vascular leak, vascular inflammation, and/or angiogenesis may further comprise identifying a patient having the disorder relating to vascular leak, vascular inflammation, and/or angiogenesis, wherein the patient has abnormal, enhanced, or increased Arf6 activity.

In another aspect, a method for treating a patient having, or at risk of developing, an ocular disorder is provided. In some embodiments, a method for treating a patient having, or at risk of developing, an ocular disorder may comprise administering to a patient an effective amount of a pharmaceutical composition comprising an Arf6 inhibitor or a pharmaceutically acceptable salt of an Arf6 inhibitor. In certain embodiments, the pharmaceutical composition may also comprise a pharmaceutically acceptable carrier. The administration of a pharmaceutical composition as described herein may reduce a pathological effect or symptom of the ocular disorder, or reduce the risk of developing the ocular disorder. In some embodiments, a pathological effect or a symptom of the ocular disease may comprise retinopathy, macular edema, and/or loss of visual acuity. In certain embodiments, the ocular disorder may include, but is not limited to, age-related macular degeneration, diabetic retinopathy, retinopathy of prematurity, and/or macular edema.

In another aspect, a method for treating a patient having, or at risk of developing, an inflammatory disorder is provided. In some embodiments, a method for treating a patient having, or at risk of developing, an inflammatory disorder may comprise administering to a patient an effective amount of a pharmaceutical composition comprising an Arf6 inhibitor or a pharmaceutically acceptable salt of an Arf6 inhibitor. In certain embodiments, the pharmaceutical composition may also comprise a pharmaceutically acceptable carrier. The administration of a pharmaceutical composition as described herein may reduce a pathological effect or symptom of the inflammatory disorder, or reduce the risk of developing the inflammatory disorder. In some embodiments, a pathological effect or a symptom of the inflammatory disorder may comprise swelling, edema, pain, respiratory distress, and/or multi-organ failure. In certain embodiments, the inflammatory disorder may include, but is not limited to, acute lung injury, acute respiratory distress, sepsis, and/or rheumatoid arthritis.

Such compounds (i.e., inhibitors of Arf6) may also be useful in methods for the treatment or prevention of a disorder treatable with an inhibitor of Arf6 in a patient. Such methods may comprise administering a therapeutically effective amount of a compound which is an Arf6 inhibitor, or a pharmaceutically acceptable salt of the Arf6 inhibitor. In some embodiments, the Arf6 inhibitor may be a compound of Formula I.

In a certain aspect, there is provided a method for the treatment or prevention of a disorder treatable by inhibiting the activity of Arf6 in a patient. The method may comprise administering a therapeutically effective amount of a pharmaceutical composition comprising an Arf6 inhibitor, or a pharmaceutically acceptable salt of an Arf6 inhibitor. In certain embodiments, the pharmaceutical composition may further comprise a pharmaceutically acceptable carrier. Additionally, methods for the treatment or prevention of a disorder treatable by inhibiting the activity of Arf6 in a patient may reduce a pathological effect or symptom of the disorder treatable by inhibition of the activity of Arf6, or to reduce the risk of developing the disorder treatable by inhibiting the activity of Arf6.

In certain embodiments, the methods of treating a patient as disclosed herein may comprise treating a mammalian patient, a human patient, or another suitable patient.

As discussed above, in some embodiments, the Arf6 inhibitor may comprise a compound of Formula I:

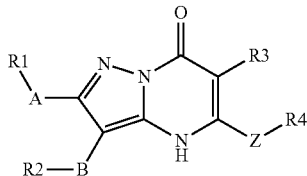

FORMULA I wherein R1 is selected from at least one of hydrogen, hydroxyl, halo, alkyl, alkoxy, haloalkyl, haloalkoxy, cycloalkyl, phenyl, substituted phenyl, pyridyl, morpholino, or pyranyl;
R2 is selected from at least one of hydrogen, alkyl, optionally substituted aryl, cycloalkyl, or sulfonyl;
R3 is selected from at least one of hydrogen, alkyl, or halo;
R4 is selected from at least one of hydrogen, alkyl, optionally substituted aryl, cycloalkyl, or pyridyl;
A, B, and Z are each independently a bond or an optionally substituted methylene; and/or pharmaceutically acceptable salts thereof. In certain embodiments, the Arf6 inhibitor may comprise at least one of Compound Numbers 1-112 as described above and/or pharmaceutically acceptable salts thereof. In certain other embodiments, also as discussed above, the Arf6 inhibitor may comprise at least one of Compound Numbers 113-144 and/or pharmaceutically acceptable salts thereof.

In another aspect, a pharmaceutical composition for use in any one of the methods of treatment disclosed herein may be provided. The pharmaceutical composition for use in any one of the methods of treatment disclosed herein may comprise a compound of Formula 1, at least one of Compound Numbers 1-112, and/or at least one of Compound Numbers 113-144. Additionally, the pharmaceutical composition for use in any one of the methods of treatment disclosed herein may comprise a pharmaceutically acceptable salt of at least one compound of Formula 1, a pharmaceutically acceptable salt of at least one of Compound Numbers 1-112, and/or a pharmaceutically acceptable salt of at least one of Compound Numbers 113-144. In various embodiments, the pharmaceutical composition for use in any one of the methods of treatment disclosed herein may further comprise a pharmaceutically acceptable carrier.

In yet another aspect, a pharmaceutical composition may be provided. The pharmaceutical composition may comprise a compound of Formula 1, at least one of Compound Numbers 1-112, and/or at least one of Compound Numbers 113-144. In some embodiments, the pharmaceutical composition may comprise a pharmaceutically acceptable salt of at least one compound of Formula 1, a pharmaceutically acceptable salt of at least one of Compound Numbers 1-112, and/or a pharmaceutically acceptable salt of at least one of Compound Numbers 113-144. In various embodiments, the pharmaceutical composition may further comprise a pharmaceutically acceptable carrier.

In certain embodiments, the pharmaceutical composition may be present in an amount effective to treat a patient having, or at risk of developing, a disorder relating to vascular leak, vascular inflammation, or angiogenesis; an ocular disorder; an inflammatory disorder; and/or a disorder treatable by inhibiting the activity of Arf6. In various embodiments, the patient may be a mammal, a human, or another suitable patient.

In yet another aspect there is provided a method for treating or preventing at least one of acute lung injury, influenza-induced acute respiratory distress, sepsis, or hemorrhagic fever virus, or other disease involving vascular leak in a mammal, comprising administering to the mammal a therapeutically effective amount of a compound or composition noted above. In a further aspect, the mammal is a human. In a still further aspect, the compound or composition is administered orally or parenterally.

In a further aspect, there is provided a method of treating or preventing at least one of an ocular disease; a lung injury; a viral infection; or an inflammatory disease, including ocular diseases involving impaired retinal permeability, impaired ocular vascularization, or ocular diseases that are the result of oxygen-induced retinopathy; acute lung injuries; H1N1 infection; and arthritis. The method may comprise administering to a patient a therapeutically effective amount of a compound or composition as described above.

The present disclosure additionally provides processes and methods for the synthesis and preparation of compounds of Formula I. General and specific processes are described in more detail as set forth in the Examples below.

EXAMPLES

To further illustrate these embodiments, the following examples are provided. These examples are not intended to limit the scope of the claimed invention, which should be determined solely on the basis of the attached claims.

Example 1—Primary Biochemical Assay for Inhibitors of Arf6

The catalytic exchange of intrinsically bound GDP for GTP that activates small GTPases, including Arf6, includes a multistep process that involves multiple conformational states of the GTPase, the respective GEF, and their interface (see, e.g., Bos J L, Rehmann H, Wittinghofer A., GEFs and GAPs: critical elements in the control of small G proteins, Cell. 2007 Jun. 1; 129(5):865-77; and Pasqualato S, Menetrey J, Franco M, Cherfils J., The structural GDP/GTP cycle of human Arf6, EMBO Rep. 2001 March; 2(3):234-8).

The primary biochemical assay uses a fluorometric assay for monitoring the replacement of bound nucleotide with a fluorogenic GTP derivative bearing a BODIPY FL moiety, allowing for the identification of compounds that can inhibit this exchange (see FIG. 1A). In certain embodiments, the methods disclosed herein may exploit the reduction of intramolecular fluorescence quenching of the modified nucleotide upon its binding to the target protein (see, e.g., McEwen D P, Gee K R, Kang H C, Neubig R R. Fluorescent BODIPY-GTP analogs: real-time measurement of nucleotide binding to G proteins. Anal Biochem. 2001 Apr. 1; 291(1): 109-17).

The truncated Arf6 derivative, which lacks the autoinhibitory N-terminal α-helix and, hence, is constitutively susceptible to nucleotide exchange, has been selected for assay construction along with the Sec7 domain of ARNO, which is known to possess all structural determinants involved in Arf6 recognition and catalysis (see FIG. 1B). The fluorometric assay formatted for 96-well microtiter plates has passed quality control based on the following criteria: i) S/B ratio of 4-fold and Z'-factor of 0.61; ii) linear correlation between signal intensity and ARNO concentration (see FIG. 1C); iii) sufficiently reproducible inhibitory effects of the reference inhibitor GDP for assay durations up to at least 1 hour (see FIG. 1D); and iv) lack of apparent fluorescence quenchers among 400 randomly selected compounds. The assay is amenable to automation with a throughput of approximately 5,000 data points per 8 hours.

Example 2—Cellular Assays

Arf6 pulldown assay: Assessment of intracellular levels of active Arf6 may be a direct mechanism-based approach for monitoring on-target cellular activities of active Arf6 inhibitors. A commercially available pull-down technique, which relies on recombinant Gga3 protein as a sensor of the GTP-bound state for the members of Arf protein family, can be employed for this purpose (see, e.g., Shiba T, Kawasaki M, Takatsu H, Nogi T, Matsugaki N, Igarashi N, Suzuki M, Kato R, Nakayama K, Wakatsuki S. Molecular mechanism of membrane recruitment of GGA by ARF in lysosomal protein transport. Nat Struct Biol. 2003 May; 10(5):386-93).

The vendor's procedure was modified from 10-cm culture dish to 24-well plate format and adapted to a number of different cell lines, including cultured mouse embryonic fibroblasts NIH 3T3 due to its robust response to Arf6 inhibitors observed in the proof-of-principle studies (see FIG. 2).

In addition to Arf6 pulldown, the following cellular assays have been established.

Figure 3A:
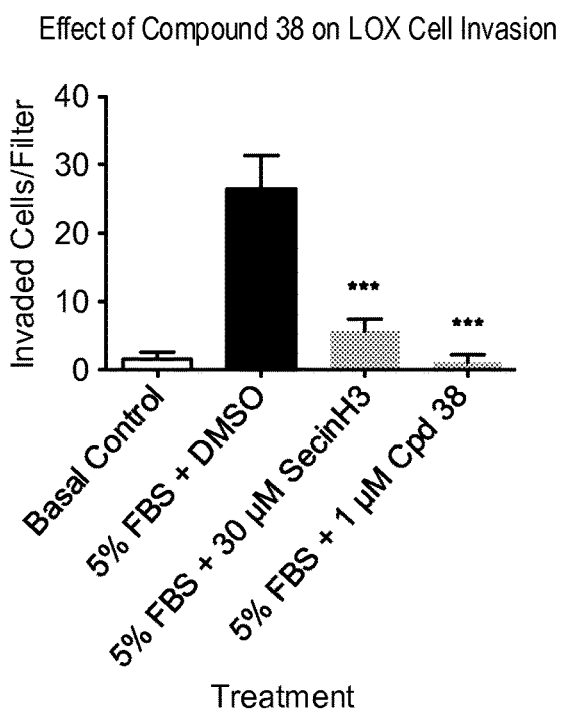
FIGS. 3A and 3B: Compound 38 can be a more potent inhibitor of melanoma cell invasion than SecinH3. At 1 µM, Compound 38 can substantially inhibit, or completely inhibit, FBS-induced LOX cell invasion through Matrigel, while the negative control does not. * $p<0.05$, *** $p<0.001$, Tukey's post-hoc test following one-way ANOVA.
Figure 3B:
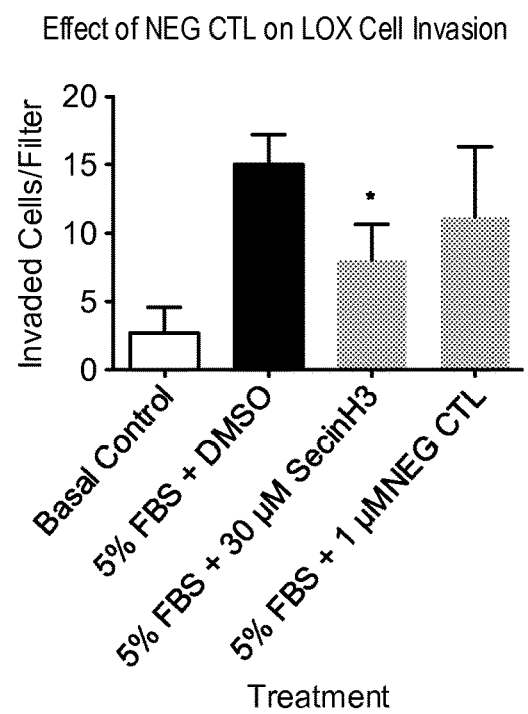

Cell invasion assay: This assay uses Matrigel Invasion Chambers (BD Biosciences) and monitors cell penetration through 8.0 μm filters coated with a solubilized basement membrane matrix, which serves as barrier for non-invading cells (see, e.g., Albini A, Iwamoto Y, Kleinman H K, Martin G R, Aaronson S A, Kozlowski J M, McEwan R N. A rapid in vitro assay for quantitating the invasive potential of tumor cells. Cancer Res. 1987 Jun. 15; 47(12):3239-45). Compound 38 can inhibit invasion of LOX melanoma cells in this assay (see FIGS. 3A and 3B).

The structure of SecinH3, a commercially available kinase inhibitor, is:

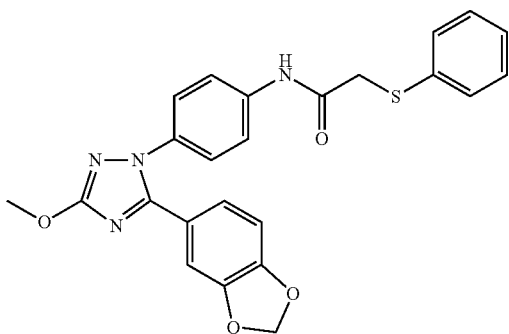 [SMILES: COc1nc(-c2ccc3c(c2)OCO3)n(-c2ccc(NC(=O)CSc3ccccc3)cc2)n1]

Figure 4A:
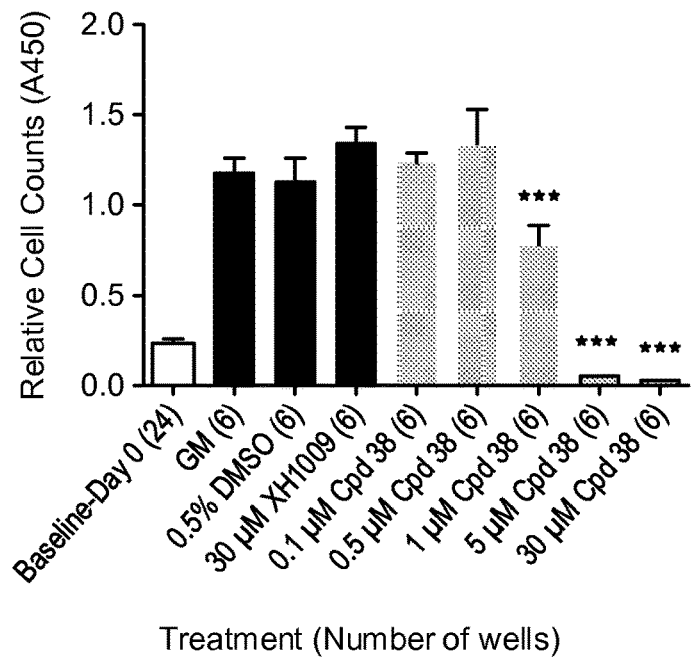
FIGS. 4A and 4B: Compound 38 can be a potent inhibitor of melanoma and glioblastoma cell proliferation. Compound 38 can be a potent inhibitor of LOX and LN-229 cell proliferation at concentrations greater than 1 µM. *** $p<0.001$, Tukey's post-hoc test following one-way ANOVA.
Figure 4B:
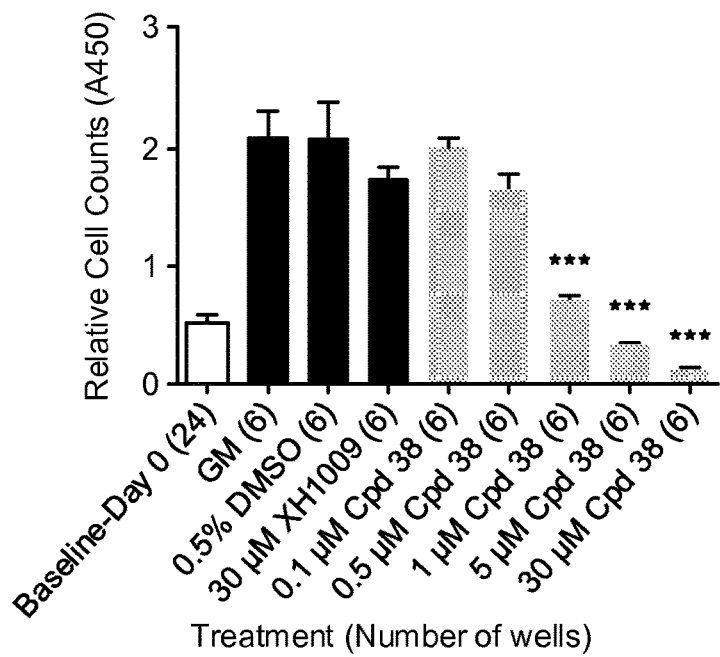

Cell proliferation assay: This assay employs WST-8 colorimetric readout (Dojindo) and relies on the total activity of mitochondrial dehydrogenases as a measure of the number of viable cells over time. Compound 38 can inhibit proliferation of both LOX melanoma cells and LN-229 glioblastoma cells (see FIGS. 4A and 4B).

Example 3—An Exemplary Synthesis of a Compound of Formula I

The synthesis of Compound 24, as shown in Table 1, was performed as follows. With reference to step (i) of FIG. 5, to a suspension of the reagent 1 (1.60 g, 5.63 mmol) in acetic acid was added ethyl 3-(4-nitrophenyl)-3-oxo-propanoate (1.47 g, 6.20 mmol) at room temperature. The reaction mixture was heated at 120° C. for 16 hours. At the end of this period, the mixture was cooled to room temperature and the solid separated was filtered and washed with cooled acetic acid followed by 20% ethyl acetate in hexanes to produce reagent 2: 2-benzyl-3-(4-chlorophenyl)-5-(4-nitrophenyl)-4H-pyrazolo[1,5-a]pyrimidin-7-one (1.2 g, 47%); $^1$H NMR (DMSO-d6): δ 4.02 (s, 2H), 6.16 (s, 1H), 7.05-7.25 (m, 5H), 7.36-7.50 (m, 4H), 8.00 (d, 2H), 8.35 (d, 2H), 12.28 (s, 1H).

Figure 5:
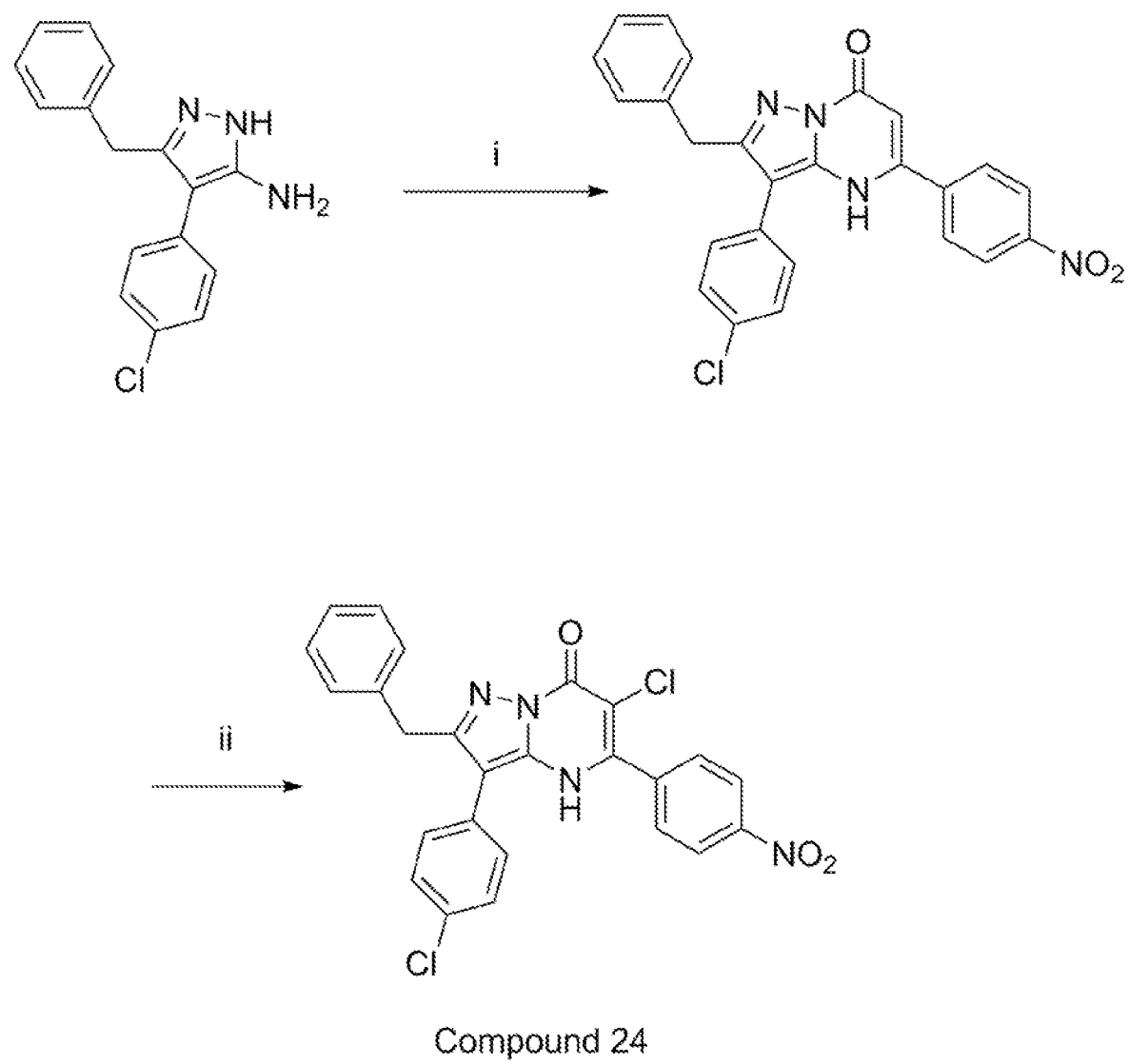
FIG. 5: The synthesis of an exemplary compound of Formula I.

With reference to step (ii) of FIG. 5, to a solution of reagent 2, (0.06 g, 0.13 mmol) in DMF was added NCS (0.021 g, 0.16 mmol) at room temperature with stirring. The stirring was continued for 16 hours at room temperature. The solid separated was collected and crude was crystallized from mixture of ethanol and dichloromethane to produce Compound 24 (2-benzyl-6-chloro-3-(4-chlorophenyl)-5-(4-nitrophenyl)-4H-pyrazolo[1,5-a]pyrimidin-7-one) as brown solid (0.032 g, 50.0%); $^1$H NMR (DMSO-d6): δ 4.10 (s, 2H), 7.05-7.50 (m, 9H), 7.90 (d, 2H), 8.38 (d, 2H), 12.8 (brs, 1H).

Example 4: Activity of Compounds 38 and 65 in Mouse Retinal Permeability

Figure 6:
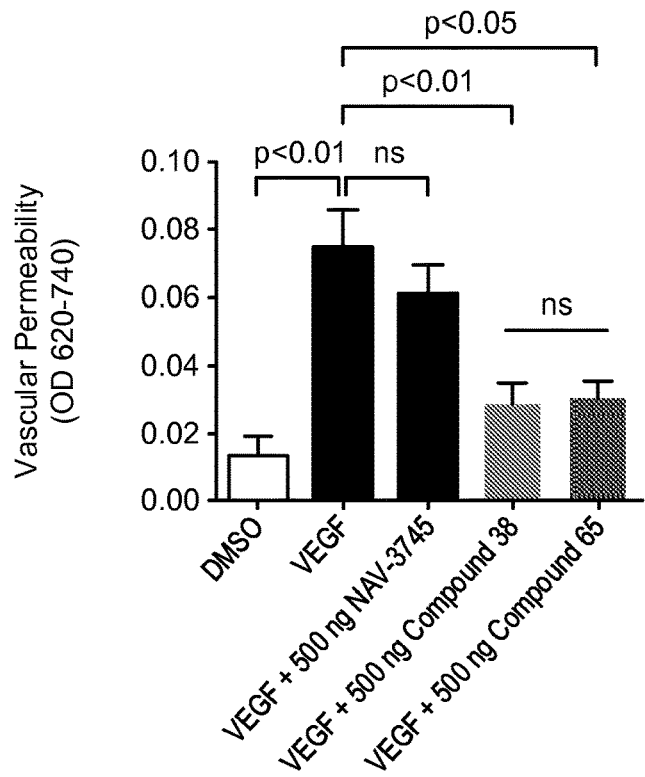
FIG. 6: Activity of an exemplary compound of Formula I in reducing VEGF-induced retinal permeability in mice.

Compounds 38 and 65 were shown to reduce VEGF-induced retinal permeability in mice (see FIG. 6). In the experiment, VEGF (50 ng) and either Compound 38 or 65 (500 ng) or NAV-3745 (500 ng) were given to mice in a single intraocular injection. Evans blue dye (EBD) was given via IV approximately 6 hours after the injection, and the retinas were harvested after an additional 2 hours. Retinal permeability was measured on Day 2 after an overnight extraction of EBD in formamide, at OD 620-740 nm.

NAV-3745 is a biochemically inactive analog of the compounds of Formula I. The structure of NAV-3745 is:

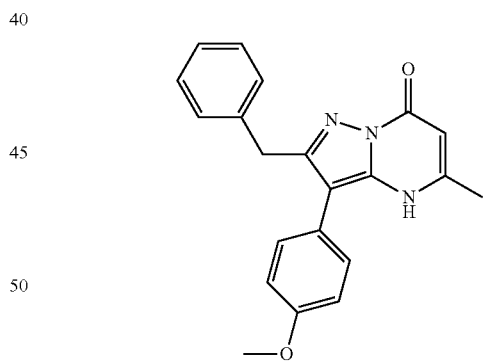

Both Compounds 38 and 65 reduced VEGF-induced retinal permeability, while NAV-3745 (negative control) had no effect. Data are shown as mean+/–SEM. ANOVA and post-hoc Tukey's test were used to analyze multiple comparisons. For these experiments, n=2-4 mice per treatment group, and both eyes were injected.

Figure 7:
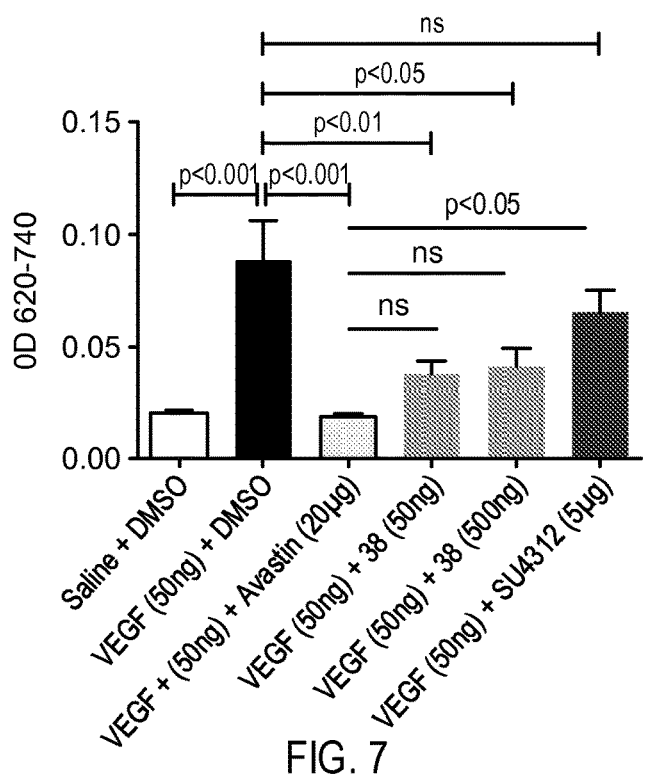
FIG. 7: Additional activity of an exemplary compound of Formula I in reducing VEGF-induced retinal permeability in mice.

FIG. 7 shows the activity of Compound 38 compared to Avastin and commercially available SU4312 for VEGF-induced retinal permeability in mice. In the experiment, VEGF (50 ng) and the test compound were given to mice in a single intraocular injection. Avastin was given at a dose of 20 μg, Compound 38 at either 50 ng or 500 ng (as noted in FIG. 7), and SU4312 at 5 μg. As with the previous experiment, Evans blue dye (EBD) was given via IV approximately 6 hours after the injection, and the retinas were harvested after an additional 2 hours. Retinal permeability was measured on Day 2 after an overnight extraction of EBD in formamide, at OD 620-740 nm.

Both Compound 38 and Avastin reduced VEGF-induced retinal permeability, while SU4312 had little effect at the chosen dose. Data are shown as mean+/−SEM. ANOVA and post-hoc Tukey's test were used to analyze multiple comparisons. For these experiments, n=3-5 mice per treatment group, and both eyes were injected.

Example 5—Activity of Compound 38 in Rat Retinal Permeability

Figure 8:
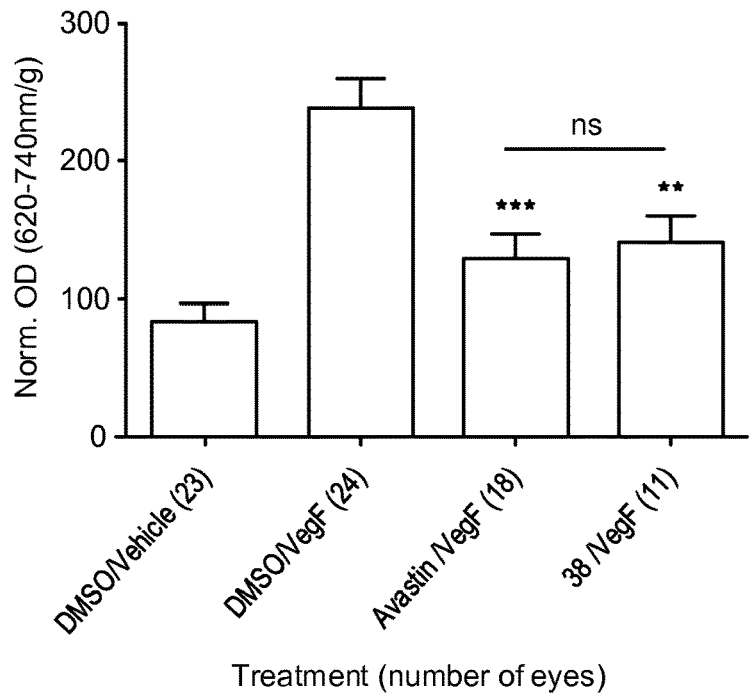
FIG. 8: Activity of an exemplary compound of Formula I in reducing VEGF-induced retinal permeability in rats.

Compound 38 was shown to reduce VEGF-induced retinal permeability in rats (see FIG. 8). In the experiment, VEGF (500 ng) and Avastin (200 μg) were given to rats in a single intraocular injection on Day 1. Compound 38 (60 mg/kg) was administered by IP injection 1 hour prior to VEGF on Day 1. Rats were given Evans blue dye (EBD) via IV infusion on Day 2, and the retinas were harvested after an additional 1.5 hours. The retinas were dissected and incubated overnight in formamide. Vascular leak was calculated on Day 3.

Compound 38 and Avastin reduced VEGF-induced retinal permeability (see FIG. 8). Data are shown as mean+/−SEM. ANOVA and post-hoc Tukey's test were used to analyze multiple comparisons. For these experiments, both eyes were injected.

Example 6—Activity of Compound 38 in Choroidal Neovascularization (CNV)

Figure 9:
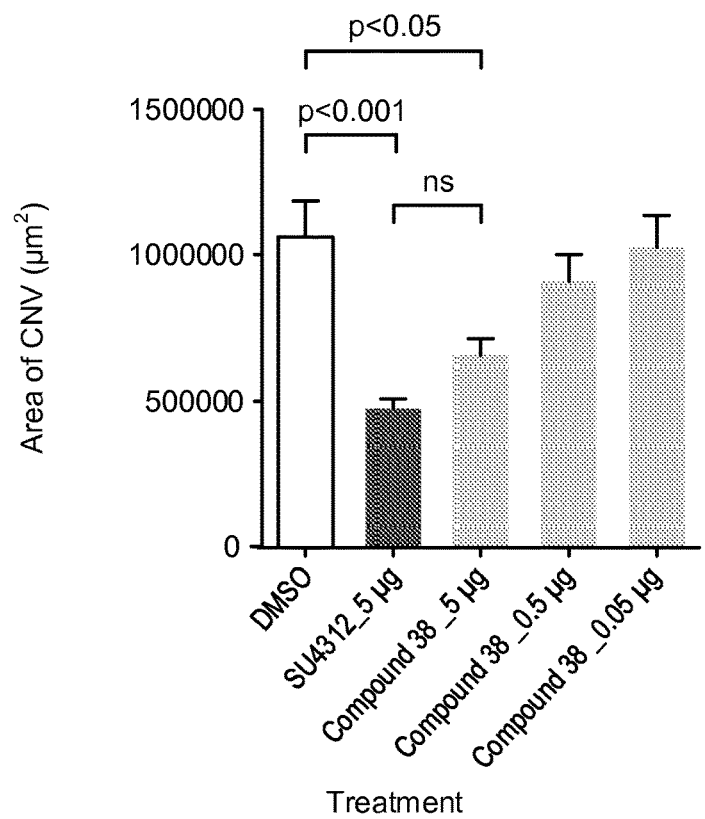
FIG. 9: Activity of an exemplary compound of Formula I in reducing Choroidal Neovascularization (CNV) in mice.

Compound 38 was shown to reduce CNV in mice (see FIG. 9). In the experiment on Day 0, the Bruch's membrane of each eye was disrupted with a laser. On Days 0 and 7, test compounds were administered, and on Day 14, the area of CNV was measured. Commercially available compound SU4312 was used as a positive control. Compound 38 was dosed at 5 μg, 0.5 μg, and 0.05 μg, as noted in FIG. 9.

Compound 38 reduced the area of CNV in a dose-dependent manner. Data are shown as mean+/−SEM. ANOVA and post-hoc Tukey's test were used to analyze multiple comparisons among all groups. For these experiments, n=10 mice per treatment group, and both eyes were treated.

Example 7—Activity of Compounds 4 and 38 in Mouse Oxygen-Induced Retinopathy

Figure 10:
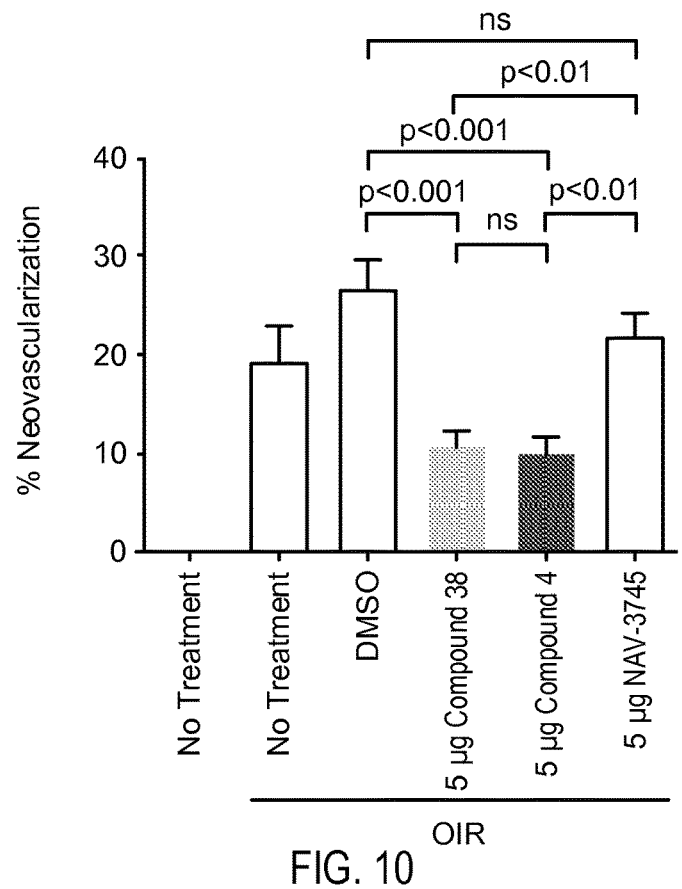
FIG. 10: Activity of exemplary compounds of Formula I in reducing oxygen-induced retinopathy in mice.

Compounds 4 and 38 were shown to reduce oxygen-induced retinopathy (OIR) in mice (see FIG. 10). In the experiment, mice pups were placed in a 75% oxygen environment from Days 5-12. The mice were returned to a normal oxygen environment on Day 13. The test compounds were administered (5 μg) by intraocular injection on Days 12 and 15, and the area of neovascularization was measured on Day 17.

Compounds 4 and 38 reduced the area of neovascularization. ANOVA and post-hoc Tukey's test were used to analyze multiple comparisons among all groups. For these experiments, n=4-6 mice per treatment group, and both eyes were treated.

Figure 11:
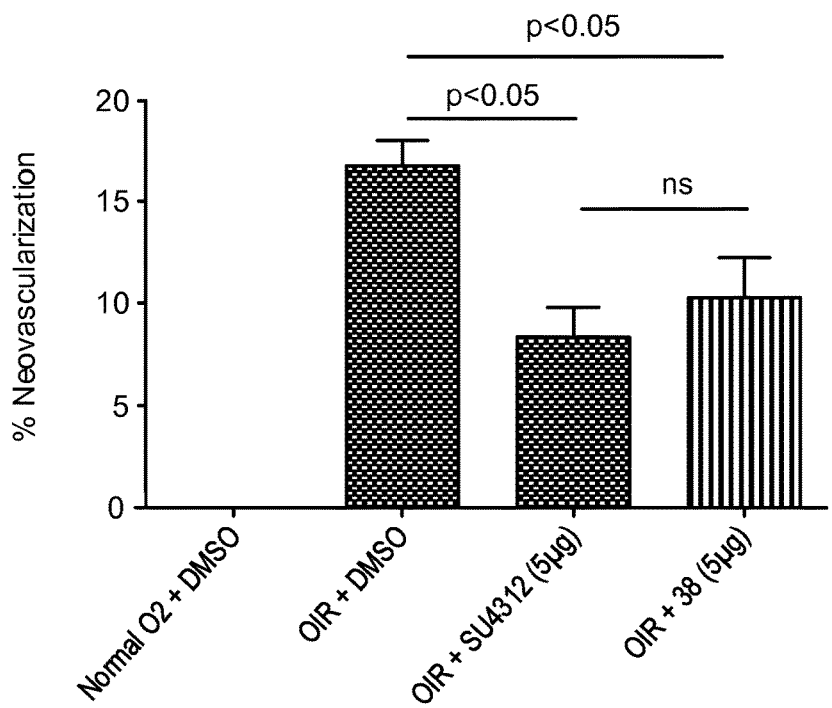
FIG. 11: Additional activity of an exemplary compound of Formula I in reducing oxygen-induced retinopathy in mice.

Compound 38 was compared with SU4312 in oxygen-induced retinopathy (OIR) in mice (see FIG. 11). In the experiment, mice pups were placed in a 75% oxygen environment from Days 5-12. The mice were returned to a normal oxygen environment on Day 13. The test compounds were administered (5 μg) by intraocular injection on Days 12 and 15, and the area of neovascularization was measured on Day 17.

Compound 38 and SU4312 both reduced the area of neovascularization. ANOVA and post-hoc Tukey's test were used to analyze multiple comparisons among all groups. For these experiments, n=4-5 mice per treatment group, and both eyes were treated.

Example 8—Activity of Compound 38 in LPS-Induced Acute Lung Injury

Figure 12A:
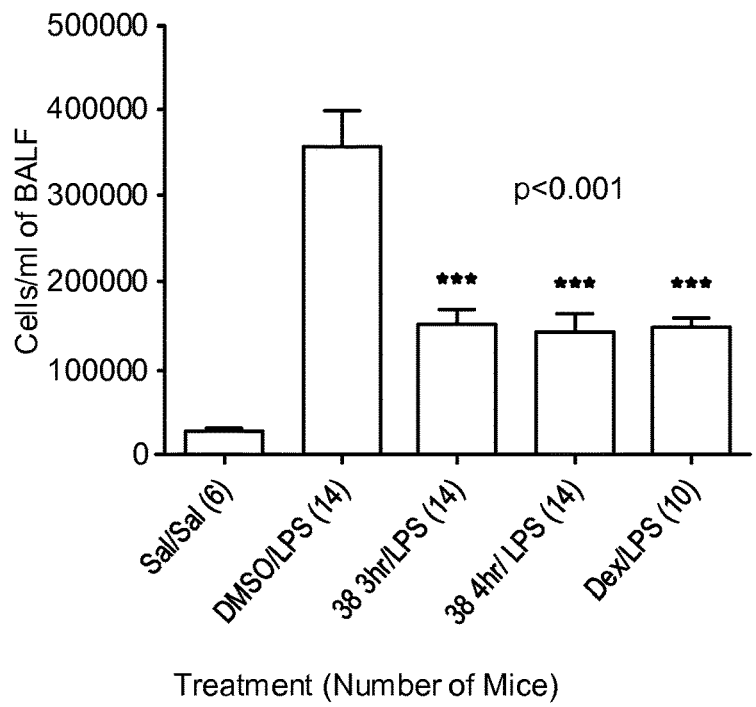
FIGS. 12A and 12B: Activity of an exemplary compound of Formula I in mouse LPS-induced acute lung injury.
Figure 12B:
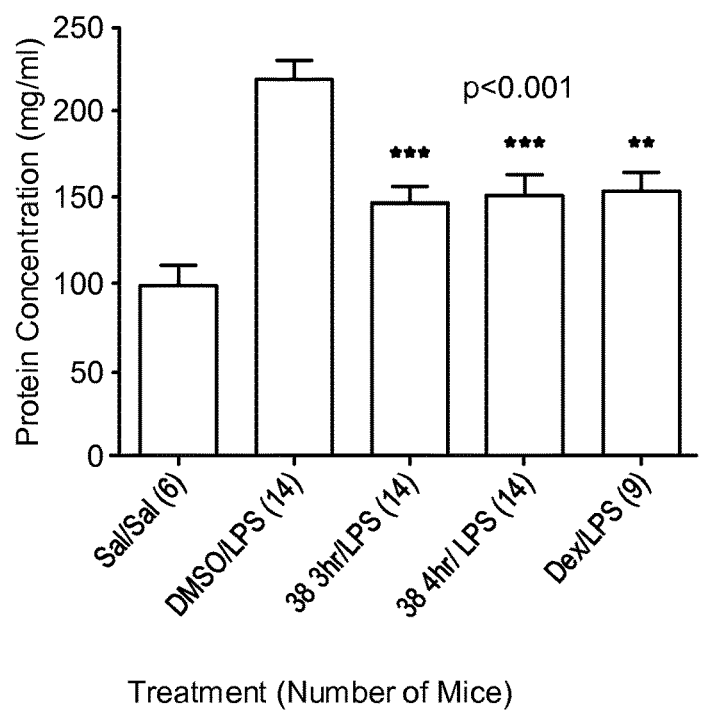

Compound 38 was shown to affect lipopolysaccharide (LPS)-induced acute lung Injury in mice (see FIGS. 12A and 12B). In the experiment, LPS (5 mg/kg) was given by intra-tracheal instillation. Compound 38 (60 mg/kg) was given either 3 hours or 4 hours after the LPS, as indicated in the Figures. Dexamethasone (5 mg/kg) was given as a positive control 2 hours after the LPS. Bronchoalveolar fluid (BALF) was analyzed for cell count and protein 24 hours after the LPS.

Compound 38 reduced the number of cells (see FIG. 12A) and protein concentration (see FIG. 12B) in the lung fluid in a similar manner as dexamethasone. ANOVA and post-hoc Tukey's test were used to analyze multiple comparisons.

Example 9—Activity of Compound 65 in Treating H1N1 Viral Infection

Figure 13:
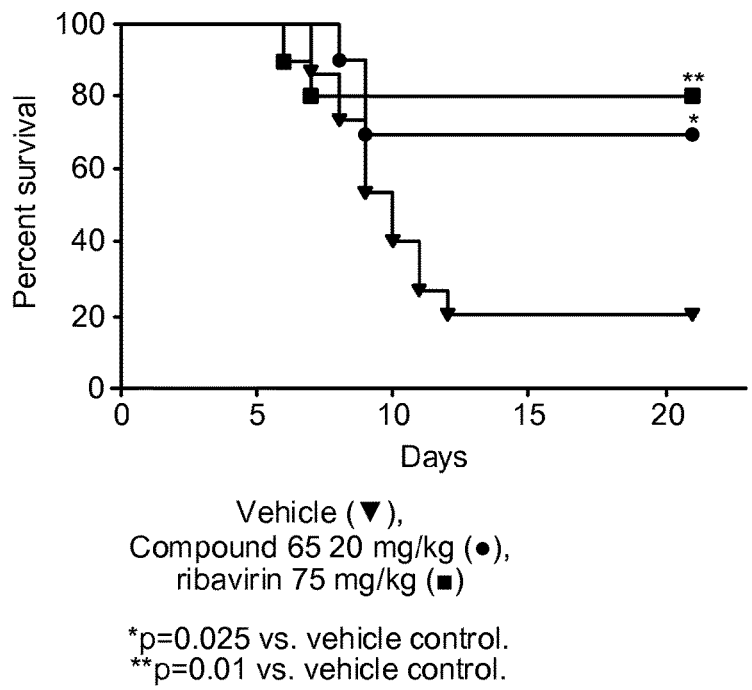
FIG. 13: Activity of an exemplary compound of Formula I for reducing mortality related to a viral infection in mice.

Compound 65 was shown to reduce mortality in mice infected with H1N1 virus (see FIG. 13). In the experiment, vehicle (▼), Compound 65 (●; 20 mg/kg) or ribavirin (■; 75 mg/kg) was given 4 hour prior to intranasal administration of virus, and the test compounds were given by IP injection once daily (QD) for five days.

Compound 65 reduced the mortality of mice nearly as well as ribavirin. The Gehan-Breslow-Wilcoxon test followed by Bonferroni correction was used to analyze multiple comparisons. *p=0.025 vs. vehicle control; **p=0.01 vs. vehicle control.

Figure 14:
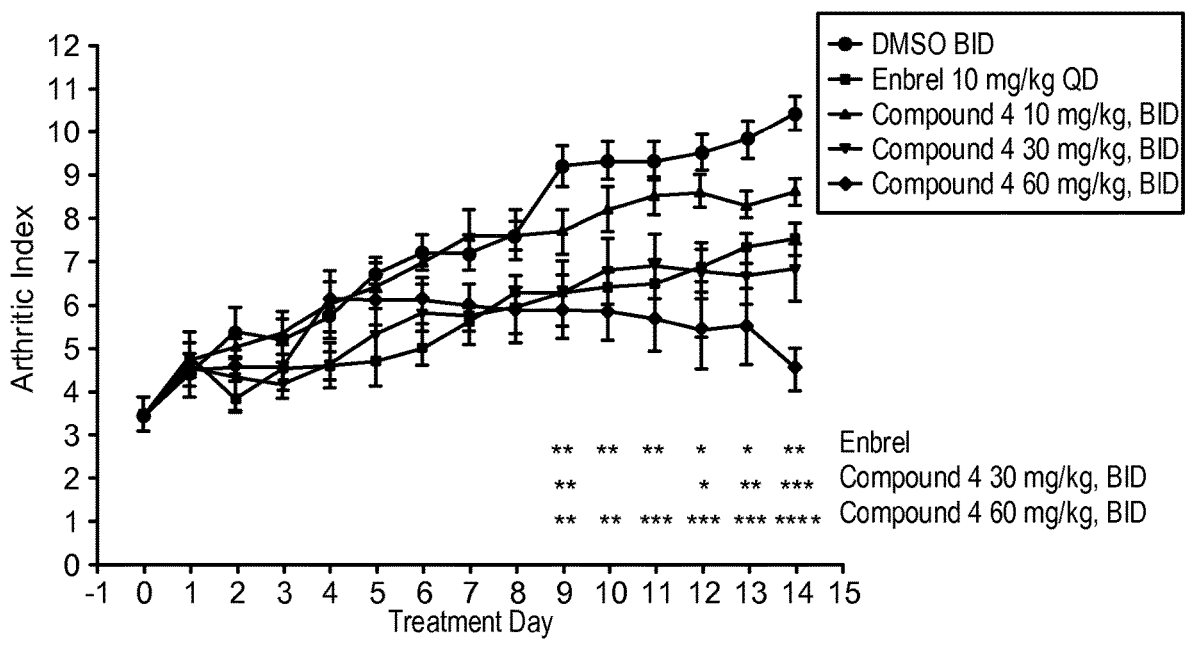
FIG. 14: Activity of an exemplary compound of Formula I for treating an inflammatory disease.

Example 10—Activity of Compound 4 in a Mouse Model of Collagen-Induced Arthritis Compound 4 was shown to reduce inflammation in a mouse model of arthritis (see FIG. 14). In the experiment, mice were immunized with collagen on Days 1 and 21, and randomized to treatment groups on or around Day 28, then subject to fourteen days of treatment with a test compound. Vehicle (●), Compound 4 at 10 mg/kg (▲), Compound 4 at 30 mg/kg (▼), Compound 4 at 60 mg/kg (♦), or Enbrel (■; 10 mg/kg) was given. Compound 4 was given twice daily (BID); Enbrel was given once daily (QD); and vehicle was given twice daily (BID).

Compound 4 reduced inflammation in mice as measured by the arthritic index nearly as well as, or better than, Enbrel, in a dose-dependent manner. The error bars represent the SEM; two-way ANOVA was used to provide a treatment p<0.0001; and Bonferroni's post hoc test was used to provide a *p=0.05, p=0.01, *p<0.001, and ****p<0.0001.

References to approximations are made throughout this specification, such as by use of the terms "about" or "approximately." For each such reference, it is to be understood that, in some embodiments, the value, feature, or characteristic may be specified without approximation. For example, where qualifiers such as "about," "substantially," and "generally" are used, these terms include within their scope the qualified words in the absence of their qualifiers.

Reference throughout this specification to "an embodiment" or "the embodiment" means that a particular feature, structure or characteristic described in connection with that embodiment is included in at least one embodiment. Thus, the quoted phrases, or variations thereof, as recited throughout this specification are not necessarily all referring to the same embodiment.

The claims following this written disclosure are hereby expressly incorporated into the present written disclosure, with each claim standing on its own as a separate embodiment. This disclosure includes all permutations of the independent claims with their dependent claims. Moreover, additional embodiments capable of derivation from the independent and dependent claims that follow are also expressly incorporated into the present written description.

It will be apparent to those having skill in the art that many changes may be made to the details of the above-described embodiments without departing from the underlying principles of the invention. The scope of the present invention should, therefore, be determined only by the following claims.

The invention claimed is:

1. A method for treating a patient having vascular leak, the method comprising:
   administering to the patient an effective amount of a pharmaceutical composition comprising:
   an Arf6 inhibitor comprising a compound of Formula I,

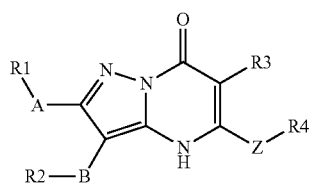

Formula I wherein R1 is selected from at least one of hydrogen, methyl, trifluoromethyl, hydroxyl, pyridyl, cyclopropyl, morpholino, tert-butyl, and phenyl optionally substituted with one or more alkyl, alkoxy, alkylthio, or halo groups;
   R2 is a phenyl optionally substituted with one or two substituents selected from the group consisting of hydrogen, chloro, fluoro, methoxy, trifluoromethyl, methyl, and phenyl;
   R3 is selected from the group consisting of hydrogen and chloro;
   R4 is selected from the group consisting of hydrogen, pyridyl, cycloalkyl, and a phenyl optionally substituted with one or more alkyl, alkoxy, aryloxy, halo, nitro, cyano, carboxy, amido, sulfonyl, sulfonamido, amino, or pyridyl, groups; and
   A, B, and Z are each independently a bond or optionally substituted methylene;
      or a pharmaceutically acceptable salt thereof inhibitor; and
      a pharmaceutically acceptable carrier;
   to reduce a pathological effect or symptom of having vascular leak.

2. The method of claim 1, wherein the patient having vascular leak has a disorder selected from at least one of an acute lung injury, acute respiratory distress syndrome, sepsis, age-related macular degeneration, and rheumatoid arthritis.

3. The method of claim 1, wherein the patient having vascular leak has a hemorrhagic fever virus infection selected from at least one of an Ebola virus infection, a Marburg virus infection, a hantavirus infection, and a dengue virus infection.

4. The method of claim 1, further comprising identifying a patient having a disorder relating to vascular leak, wherein the patient has enhanced Arf6 activity.

5. The method of claim 1, wherein R1 selected from the group consisting of benzyl, 4-methoxybenzyl, 3-chlorophenyl, 4-chlorophenyl, cyclopropyl, and trifluoromethyl.

6. The method of claim 1, wherein R4 is selected from the group consisting of benzyl, phenyl, and 4-nitrophenyl.

7. A method for treating a patient having vascular leak, the method comprising administering to the patient an effective amount of a pharmaceutical composition comprising at least one of the below compounds or a pharmaceutically acceptable salt thereof:

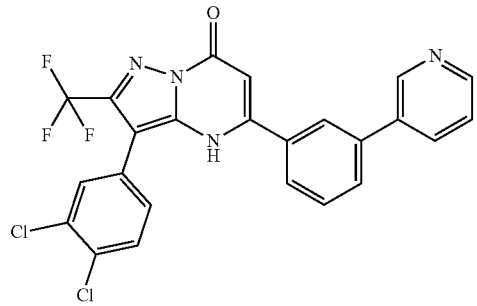

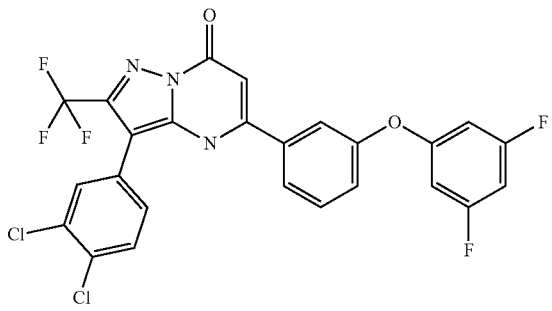

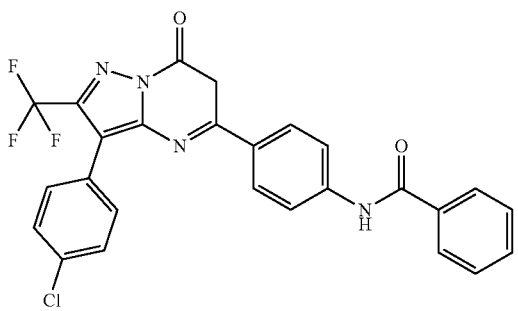

91
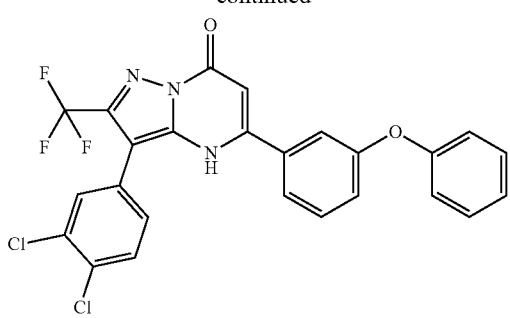
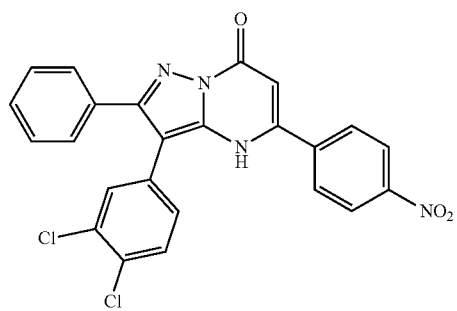
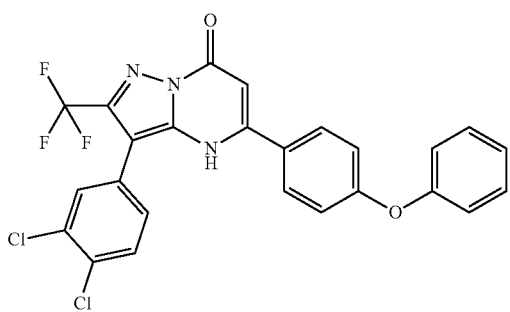
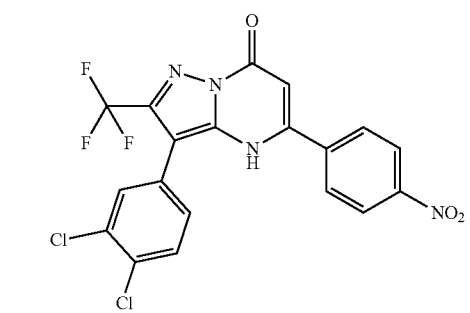
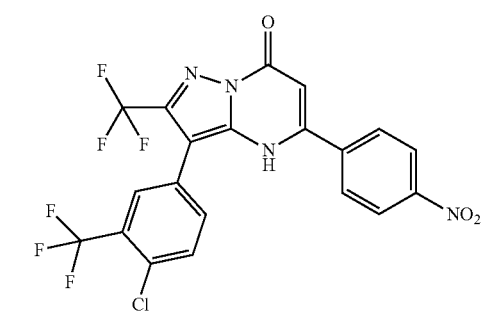
92
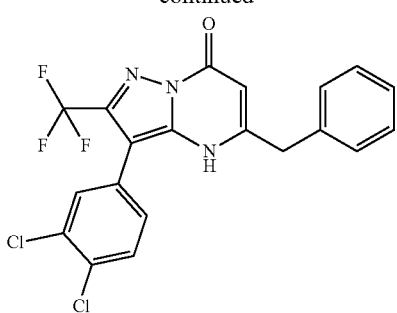
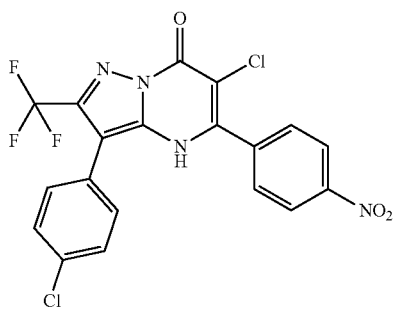
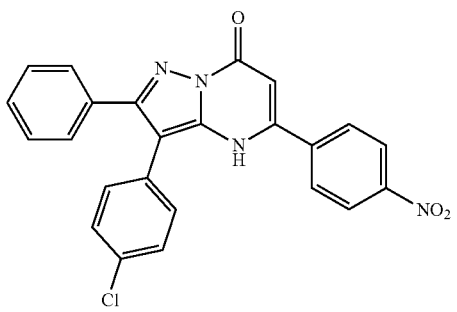
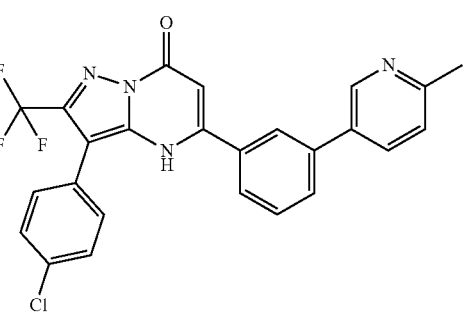
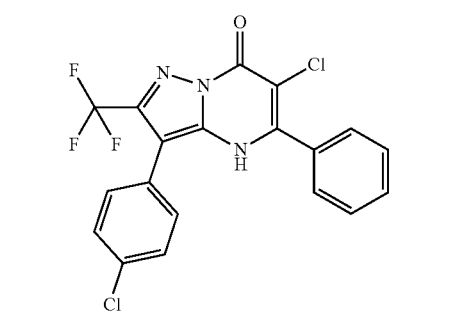

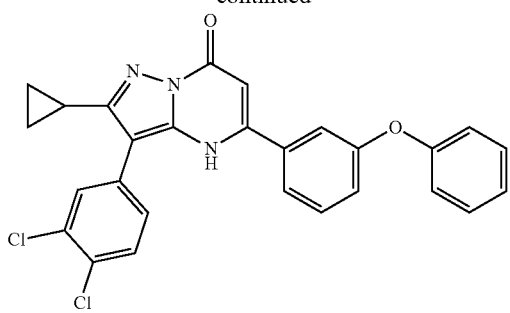
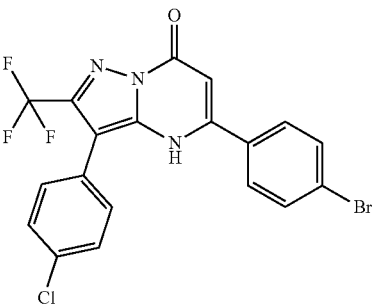
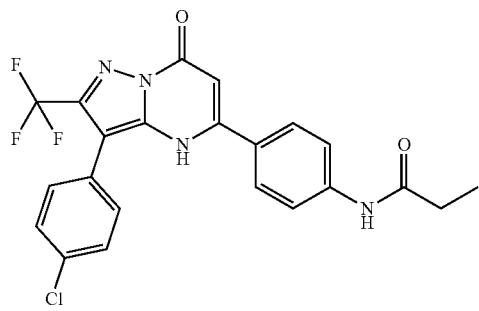
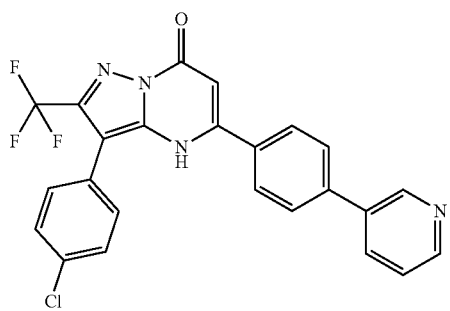
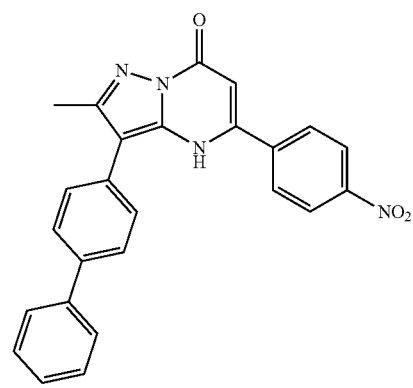
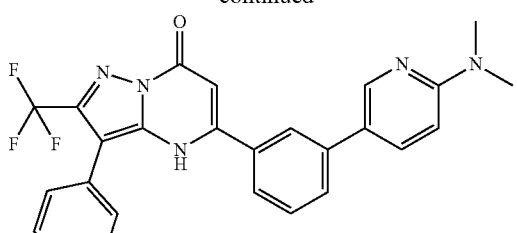
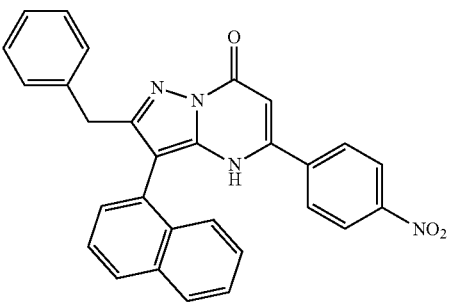
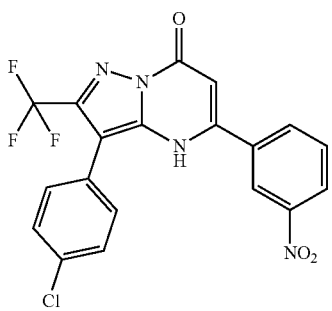
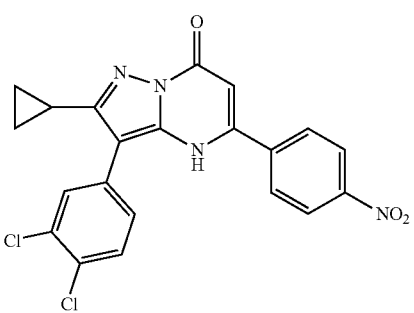
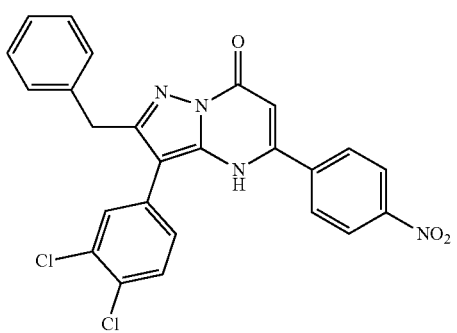

95
-continued
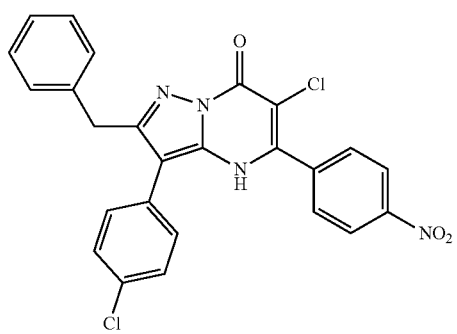
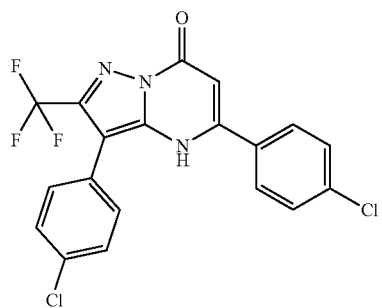
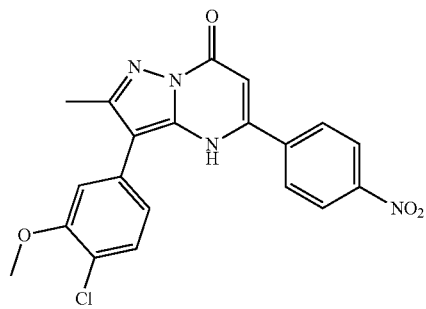
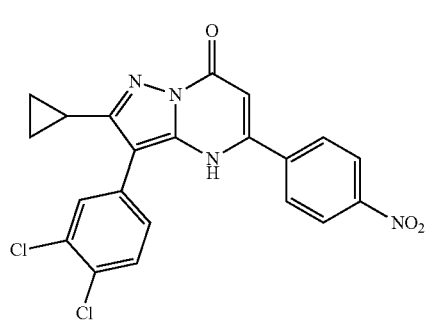
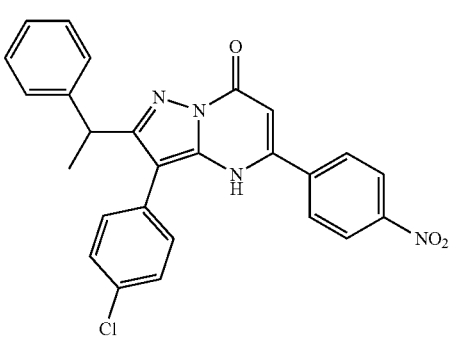
96
-continued
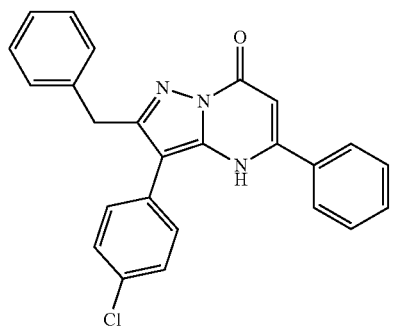
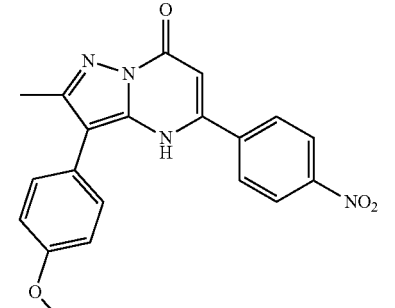
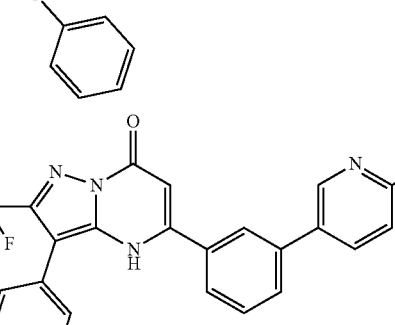
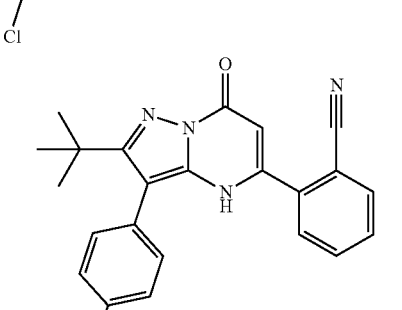
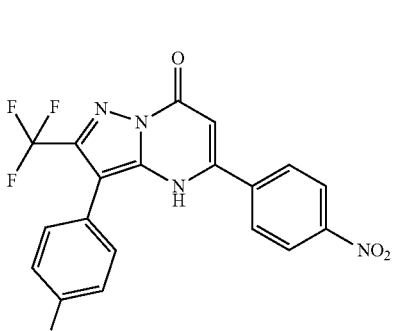

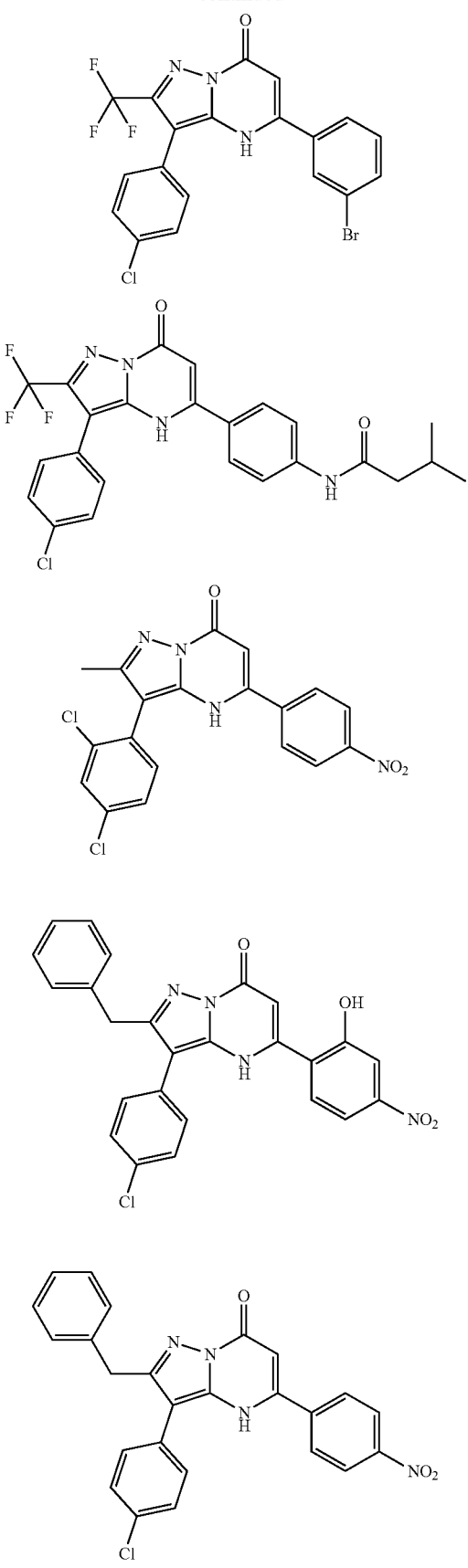

99
-continued
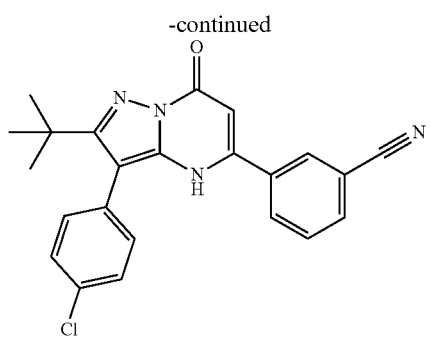
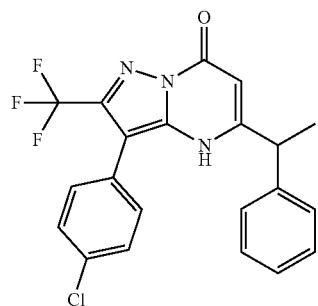
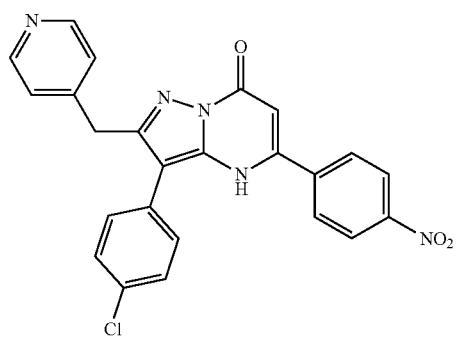 [SMILES: O=c1cc(-c2ccc([N+](=O)[O-])cc2)[nH]c2c(-c3ccc(Cl)cc3)c(Cc3ccncc3)nn12]
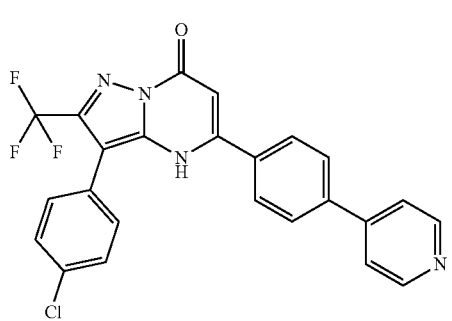
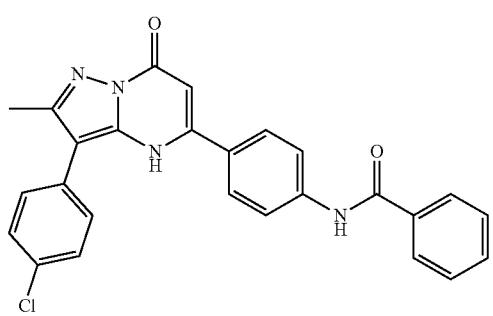
100
-continued
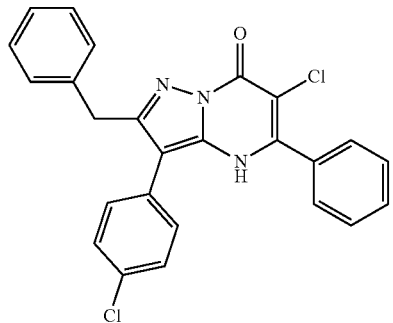
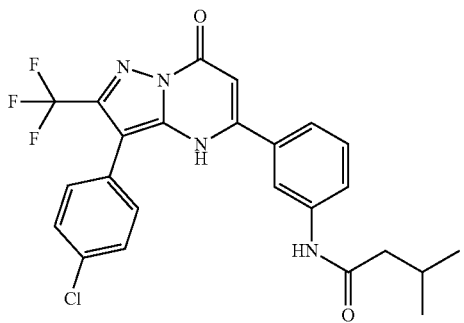
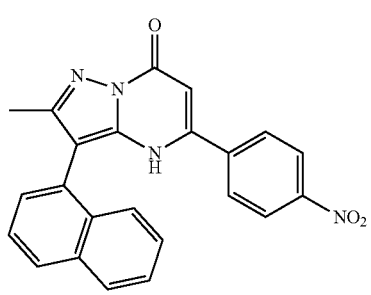
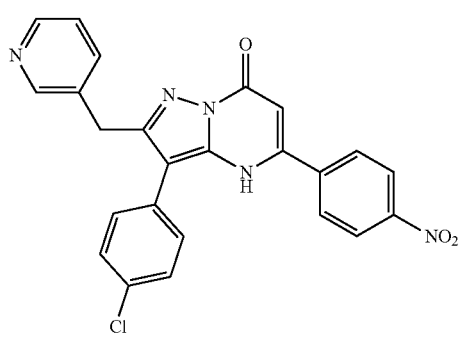
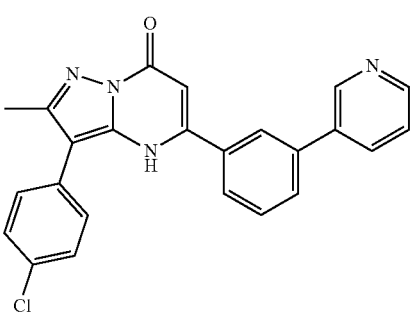

101
-continued
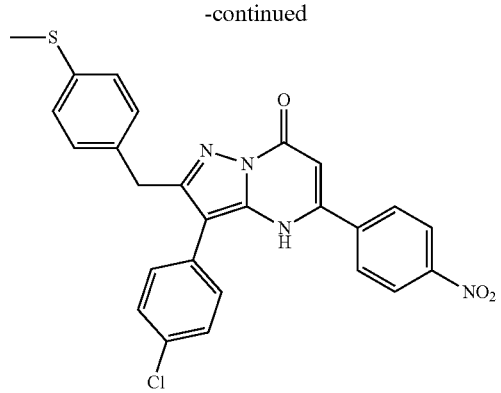
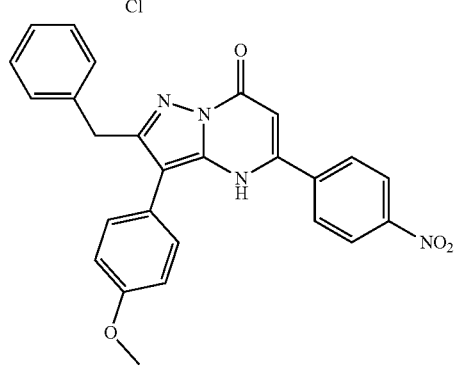
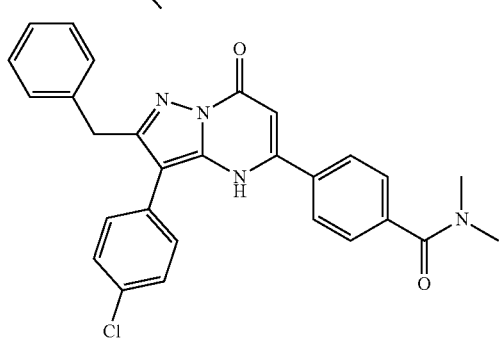
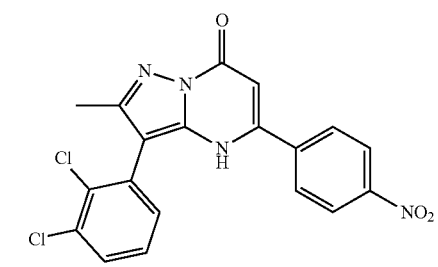
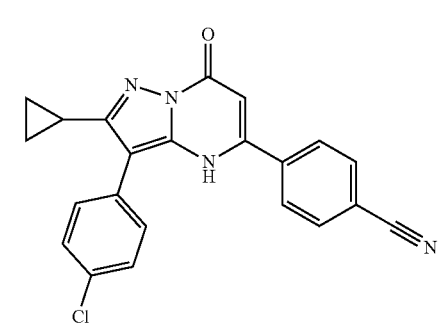
102
-continued
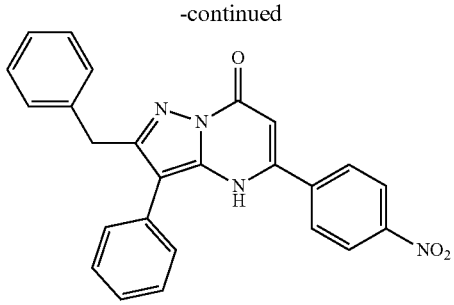
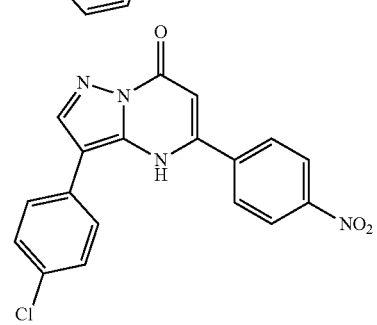
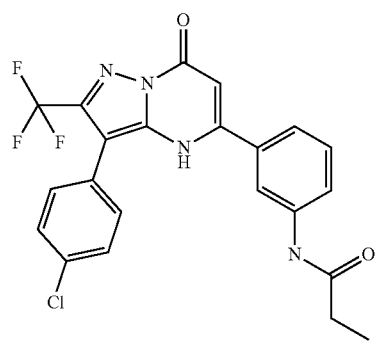
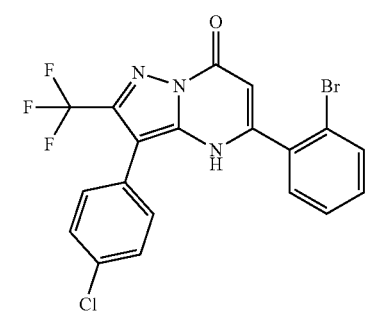
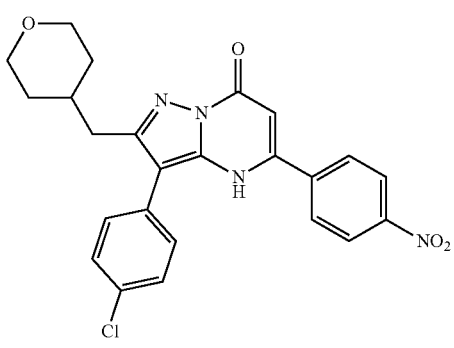

103
-continued
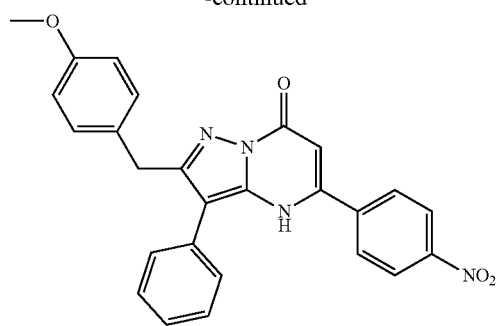
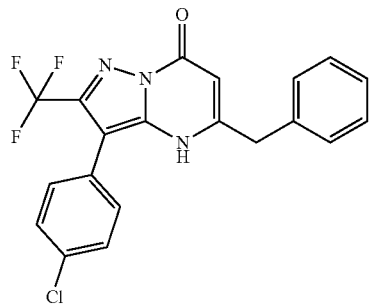
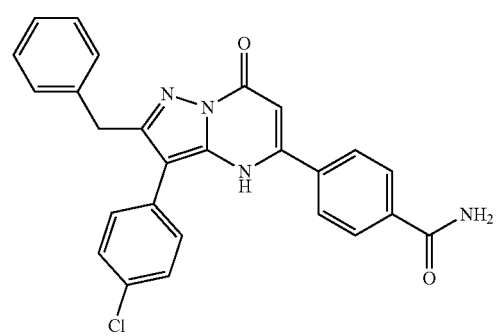
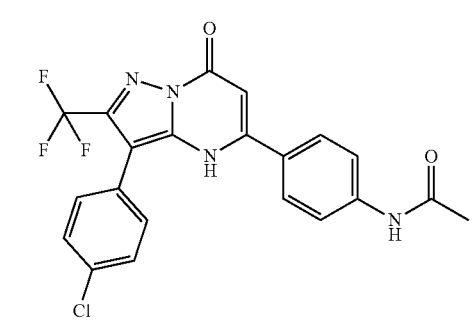
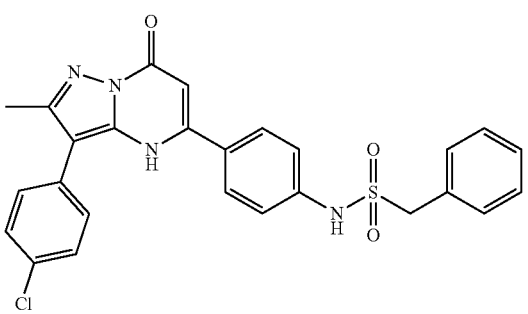
104
-continued
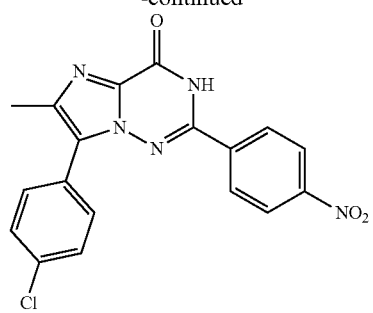
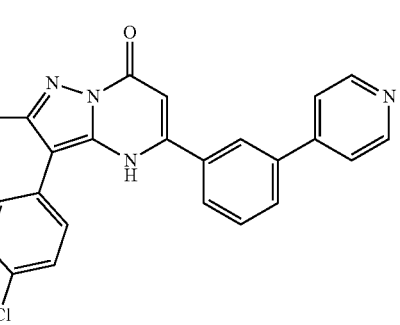
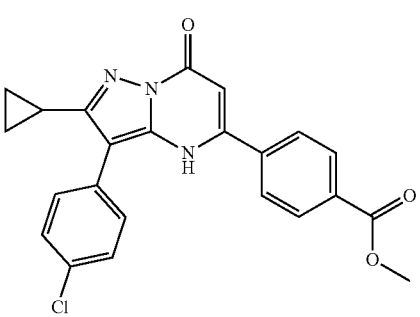
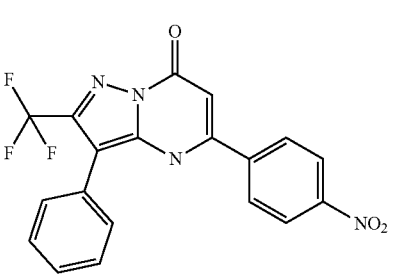
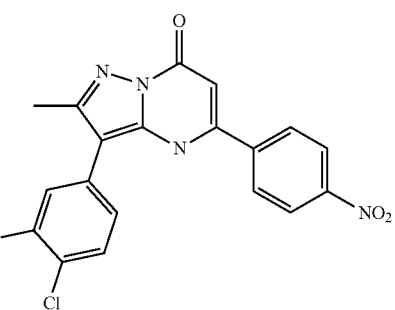

105
-continued
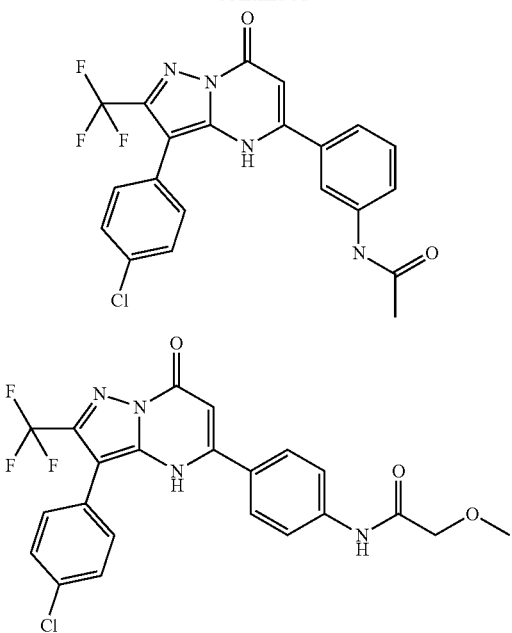
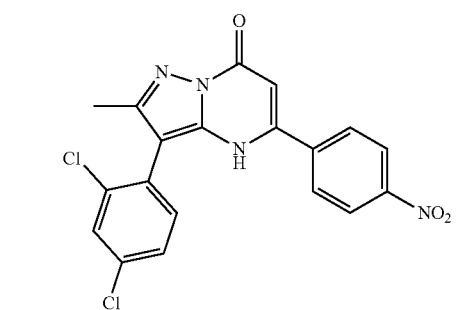
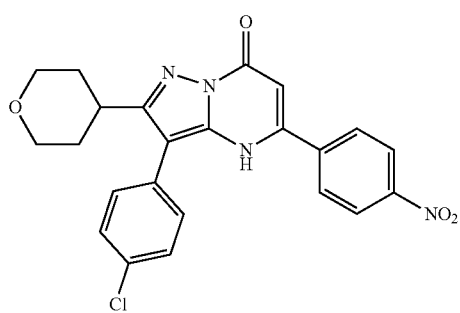
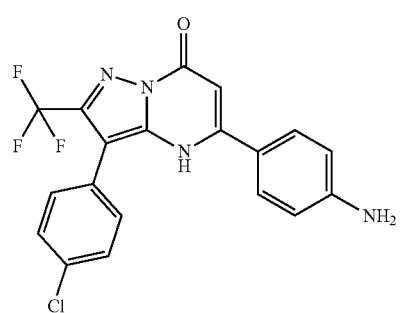
106
-continued
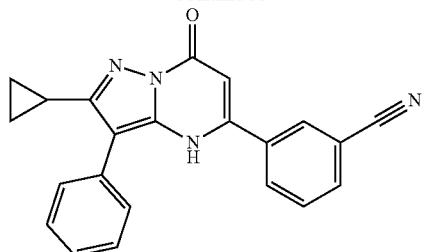
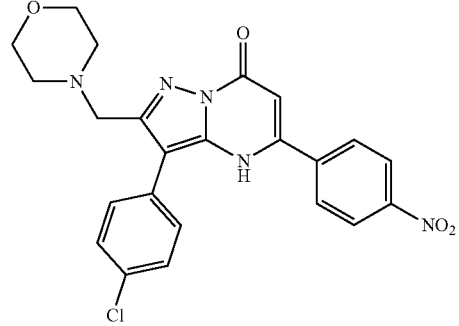
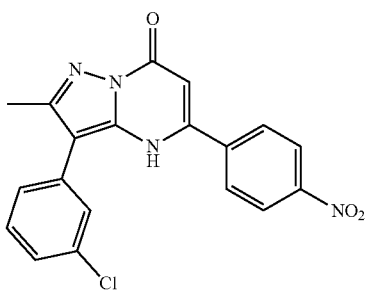
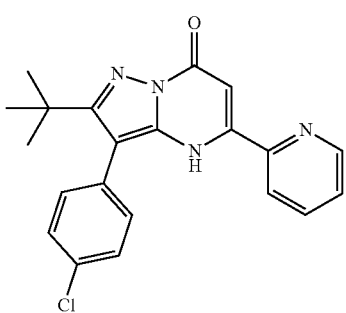
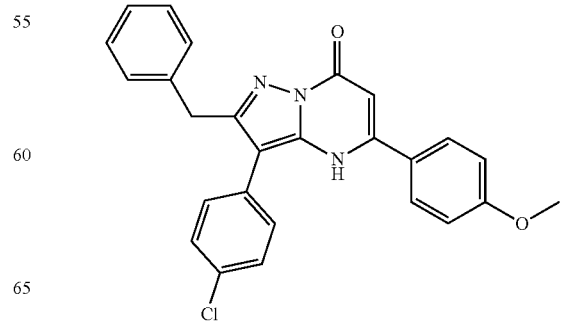

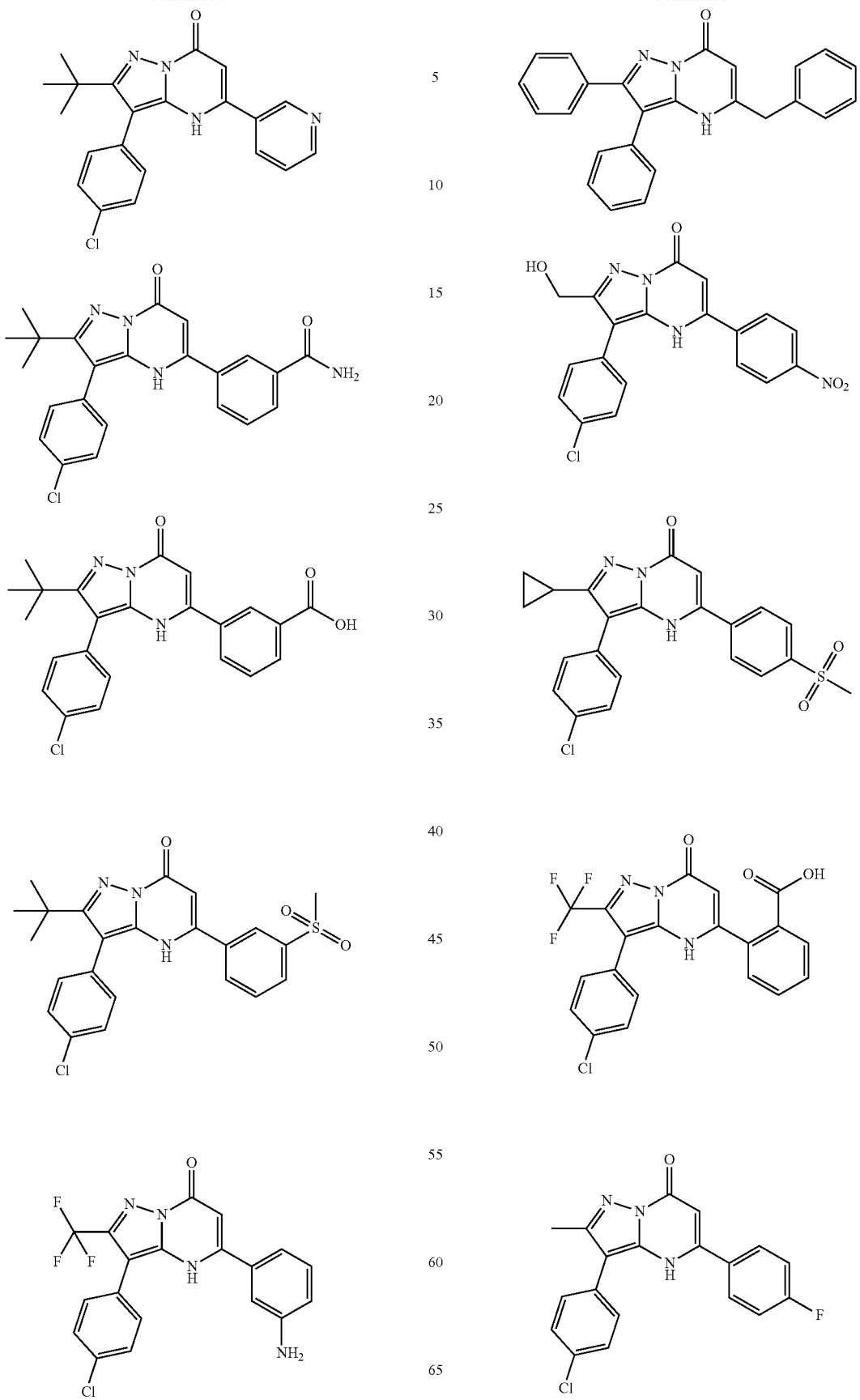

-continued
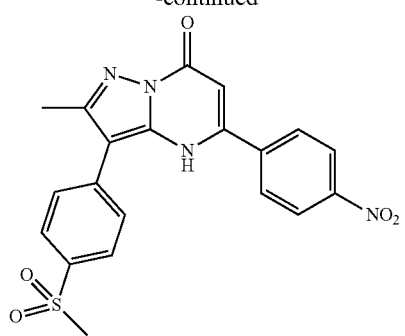
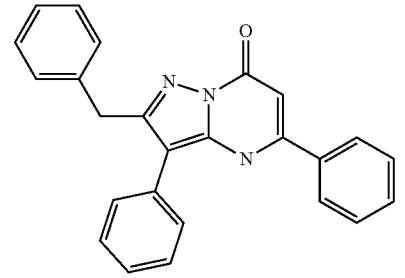
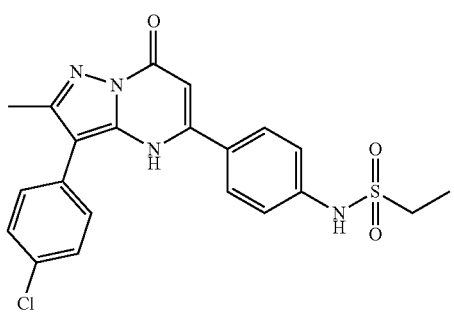
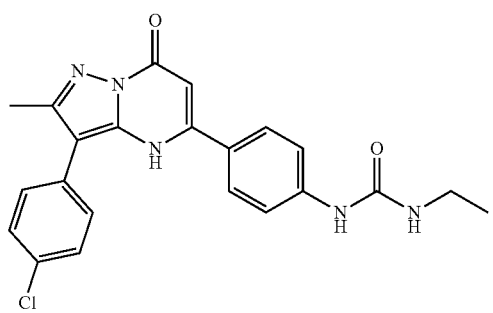
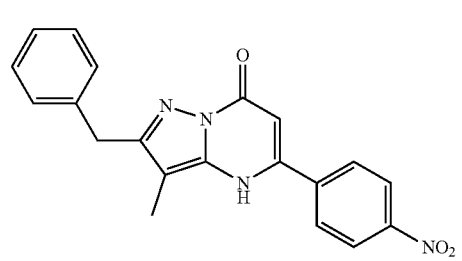
-continued
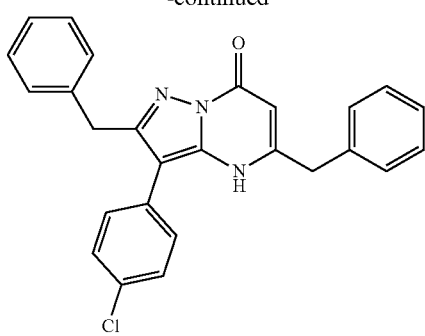
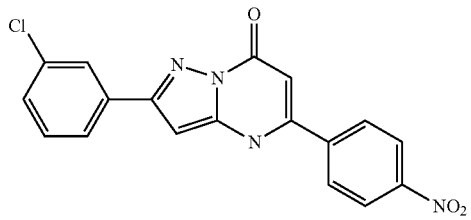
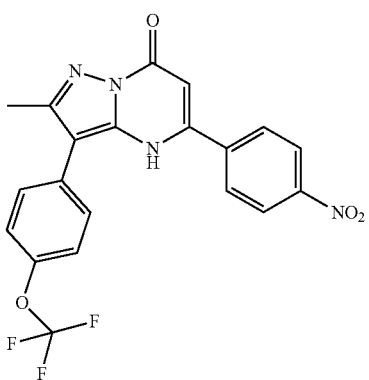
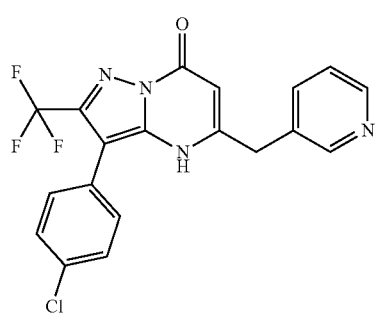
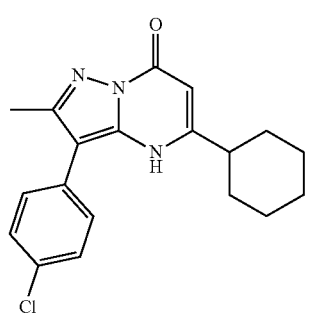

111
-continued

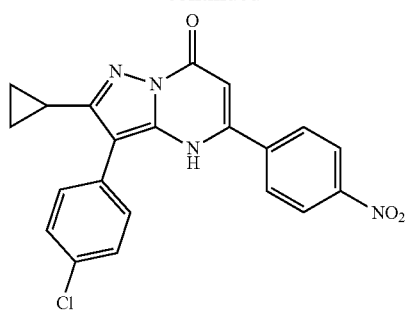

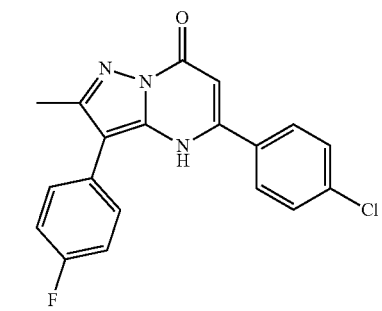

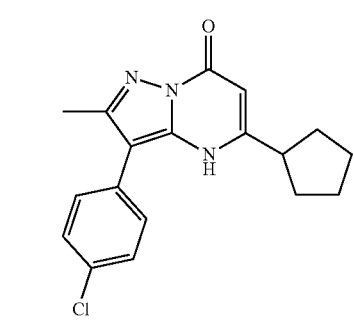

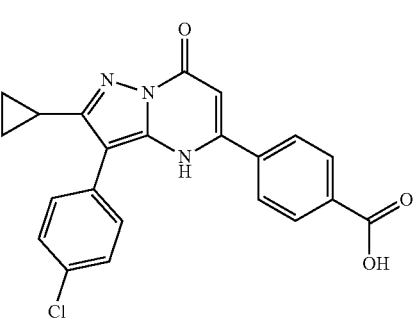

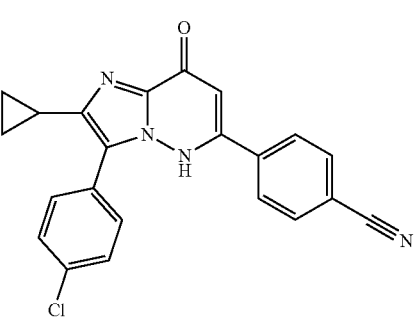

112
-continued

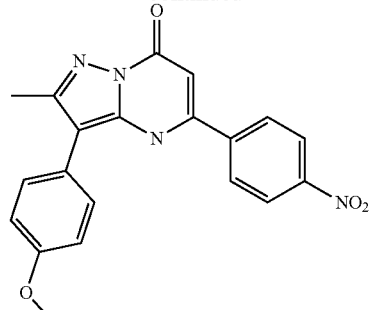

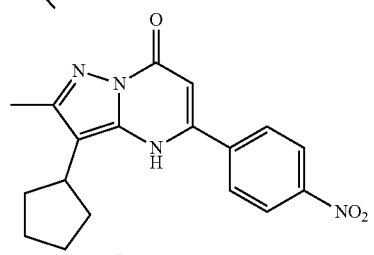

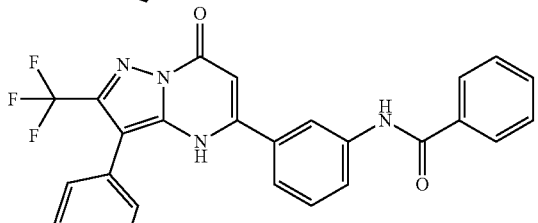

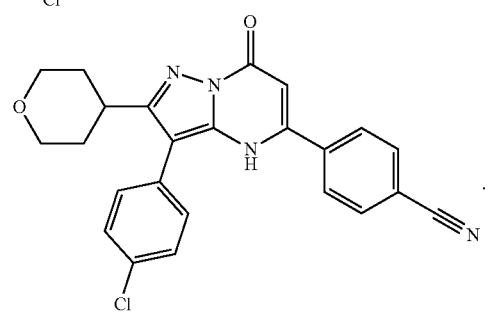

8. The method of claim 7, wherein the patient having vascular leak has acute respiratory distress.

9. A method for treating a patient having acute respiratory distress, the method comprising:
   administering to the patient an effective amount of a pharmaceutical composition comprising:
   an Arf6 inhibitor comprising a compound of Formula I, Formula I

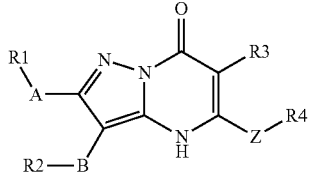

wherein R1 is selected from at least one of hydrogen, methyl, trifluoromethyl, hydroxyl, pyridyl, cyclopropyl, morpholino, tert-butyl, and phenyl optionally substituted with one or more alkyl, alkoxy, alkylthio, or halo groups;

R2 is a phenyl optionally substituted with one or two substituents selected from the group consisting of hydrogen, chloro, fluoro, methoxy, trifluoromethyl, methyl, and phenyl;

R3 is selected from the group consisting of hydrogen and chloro;

R4 is selected from the group consisting of hydrogen, pyridyl, cycloalkyl, and a phenyl optionally substituted with one or more alkyl, alkoxy, aryloxy, halo, nitro, cyano, carboxy, amido, sulfonyl, sulfonamido, amino, or pyridyl, groups; and A, B, and Z are each independently a bond or optionally substituted methylene;

or a pharmaceutically acceptable salt thereof inhibitor; and a pharmaceutically acceptable carrier;

to reduce a pathological effect or symptom of having acute respiratory distress.

10. The method of claim 9, further comprising identifying a patient having a disorder relating to acute respiratory distress, wherein the patient has enhanced Arf6 activity.

11. The method of claim 9, wherein R1 selected from the group consisting of benzyl, 4-methoxybenzyl, 3-chlorophenyl, 4-chlorophenyl, cyclopropyl, and trifluoromethyl.

12. The method of claim 9, wherein R4 is selected from the group consisting of benzyl, phenyl, and 4-nitrophenyl.

* * * * *